(12) United States Patent
Hosono

(10) Patent No.: US 10,307,286 B2
(45) Date of Patent: Jun. 4, 2019

(54) ACCOMMODATION BAG FOR STOMA APPARATUS AND STOMA APPARATUS

(71) Applicant: Tsutomu Hosono, Tokyo (JP)

(72) Inventor: Tsutomu Hosono, Tokyo (JP)

( * ) Notice: Subject to any disclaimer, the term of this patent is extended or adjusted under 35 U.S.C. 154(b) by 200 days.

(21) Appl. No.: 15/272,063

(22) Filed: Sep. 21, 2016

(65) Prior Publication Data

US 2017/0112658 A1   Apr. 27, 2017

Related U.S. Application Data

(63) Continuation of application No. PCT/JP2015/062395, filed on Apr. 23, 2015.

(30) Foreign Application Priority Data

Jul. 3, 2014 (JP) .................................. 2014-137756
Oct. 8, 2014 (JP) .................................. 2014-206852

(51) Int. Cl.
*A61F 5/445* (2006.01)
*A61F 5/448* (2006.01)

(52) U.S. Cl.
CPC .............. *A61F 5/448* (2013.01); *A61F 5/445* (2013.01)

(58) Field of Classification Search
CPC .................................. A61F 5/445; A61F 5/448
See application file for complete search history.

(56) References Cited

U.S. PATENT DOCUMENTS

| 5,203,806 A | * | 4/1993 | Broida | A61F 5/445 604/332 |
| 5,346,482 A | * | 9/1994 | Metz | A61F 5/448 604/332 |
| 5,423,782 A | * | 6/1995 | Wolrich | A61F 5/445 604/339 |

(Continued)

FOREIGN PATENT DOCUMENTS

| JP | 3048439 | 5/1998 |
| JP | 2004-113793 | 4/2004 |

(Continued)

OTHER PUBLICATIONS

International Search Report in corresponding WIPO application PCT/JP2015/062395, dated Jul. 14, 2015.

*Primary Examiner* — Susan S Su
(74) *Attorney, Agent, or Firm* — Ryan Alley IP

(57) ABSTRACT

Blowout means that the excrement enters an area between its faceplate and the one's skin, externally leaking out. In case of blowout, a clothing and a bedding are wasted and people around the ostomate gets annoyed, causing serious problems in preventing people from an advance into society. This invention is intended to prevent the excrement leaked out from externally spreading out. Adhesion unit (90) is provided so that a receiving hole (83) is arranged on the circumference of the faceplate (12). An auxiliary storage bag (31) is prepared to store the excrement leaking in case of blowout. The first opening (33) through the auxiliary storage bag is coupled to the adhesion unit. The second opening (35) through the auxiliary storage bag is coupled to the faceplate. The auxiliary storage bag envelops the receiving hole. The excrement as a result of blowout leaking from the receiving hole is captured in the auxiliary storage bag to prevent the spreadout.

13 Claims, 30 Drawing Sheets

(56) References Cited

U.S. PATENT DOCUMENTS

| | | | | |
|---|---|---|---|---|
| 5,591,144 A * | 1/1997 | Smith | ................... | A61F 5/445 |
| | | | | 604/327 |
| 5,785,695 A * | 7/1998 | Sato | ..................... | A61F 5/448 |
| | | | | 604/338 |
| 5,865,819 A | 2/1999 | Cisko, Jr. et al. | | |
| 5,938,647 A * | 8/1999 | Smith | ................... | A61F 5/445 |
| | | | | 128/DIG. 24 |
| 8,343,121 B2 * | 1/2013 | Cramer | ................. | A61F 5/445 |
| | | | | 604/334 |
| 2011/0054425 A1 * | 3/2011 | Smith | ................... | A61F 5/448 |
| | | | | 604/342 |
| 2016/0278969 A1 * | 9/2016 | De Weert | ............... | A61F 5/441 |
| 2017/0209295 A1 * | 7/2017 | Smith | ................... | A61F 5/445 |

FOREIGN PATENT DOCUMENTS

| | | |
|---|---|---|
| JP | 2006-095321 | 4/2006 |
| JP | 2007-185425 | 7/2007 |
| JP | 2008-000316 | 1/2008 |
| JP | 2009-254719 | 3/2009 |

\* cited by examiner

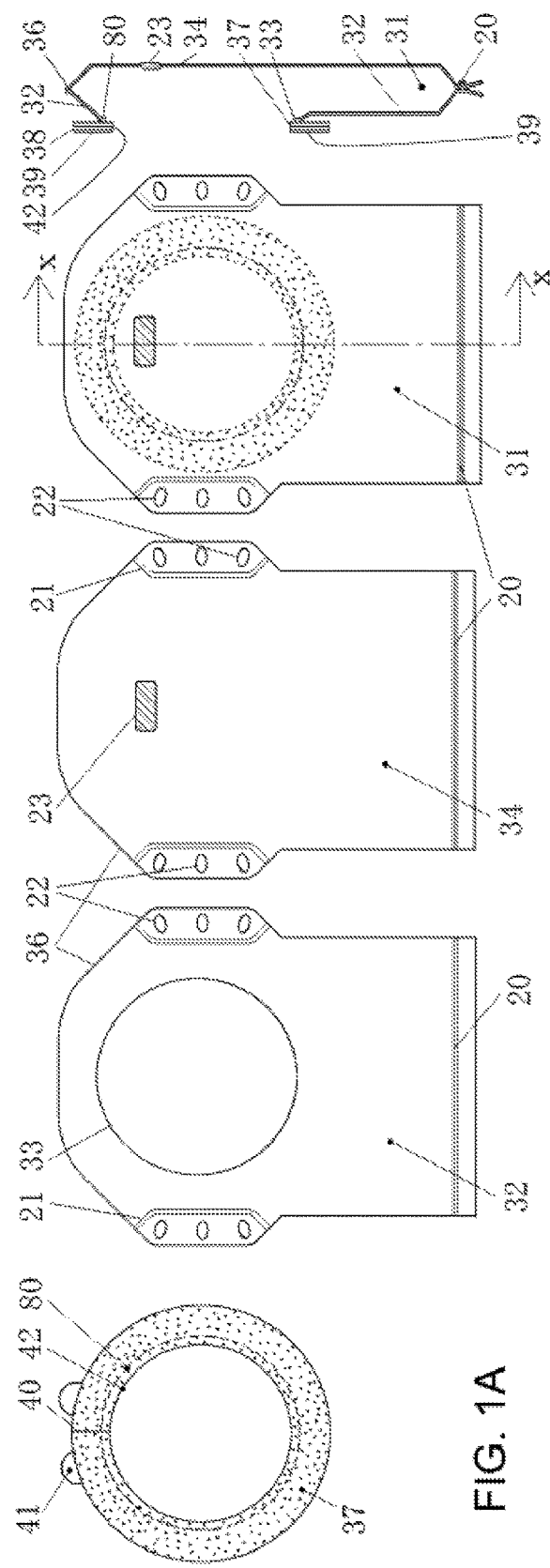

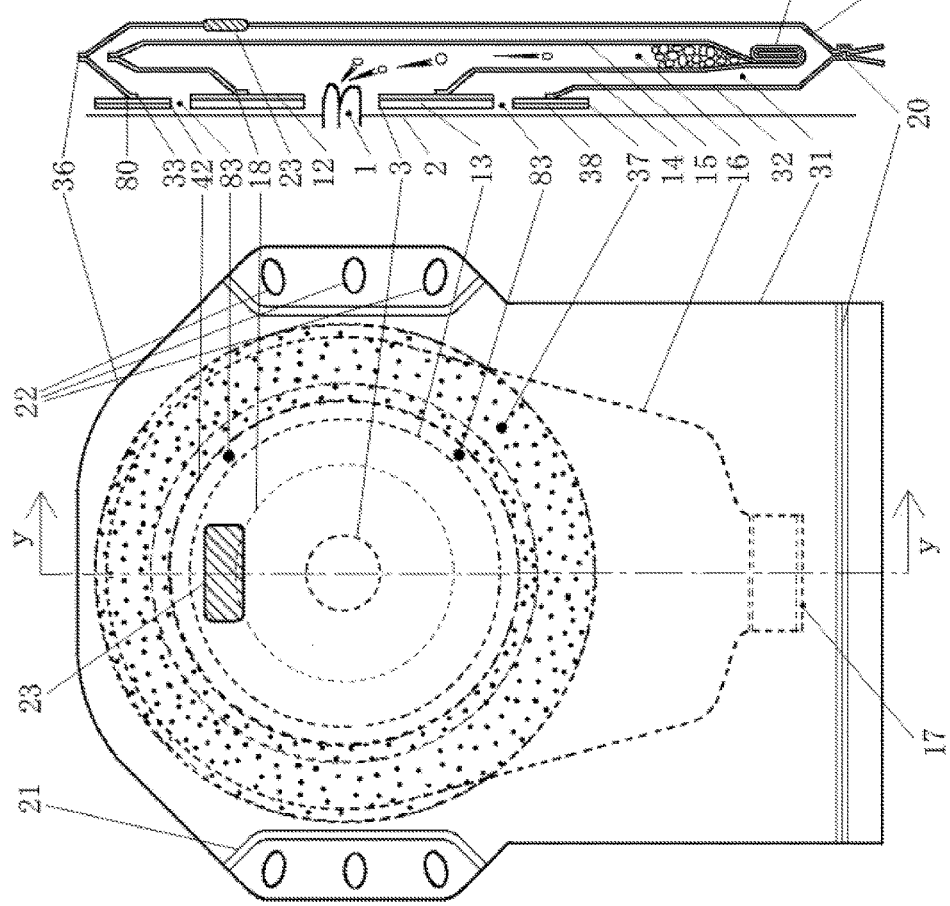

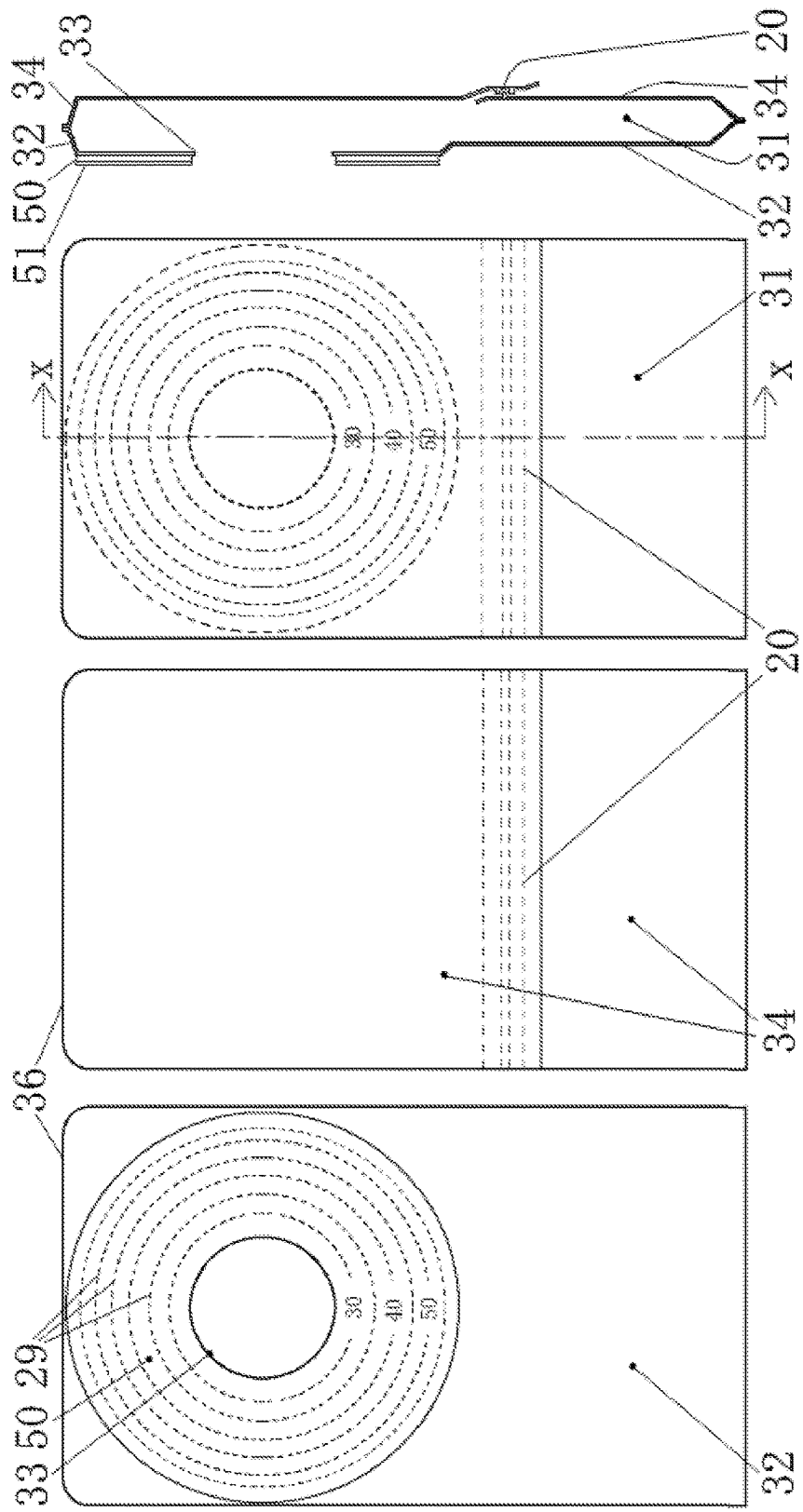

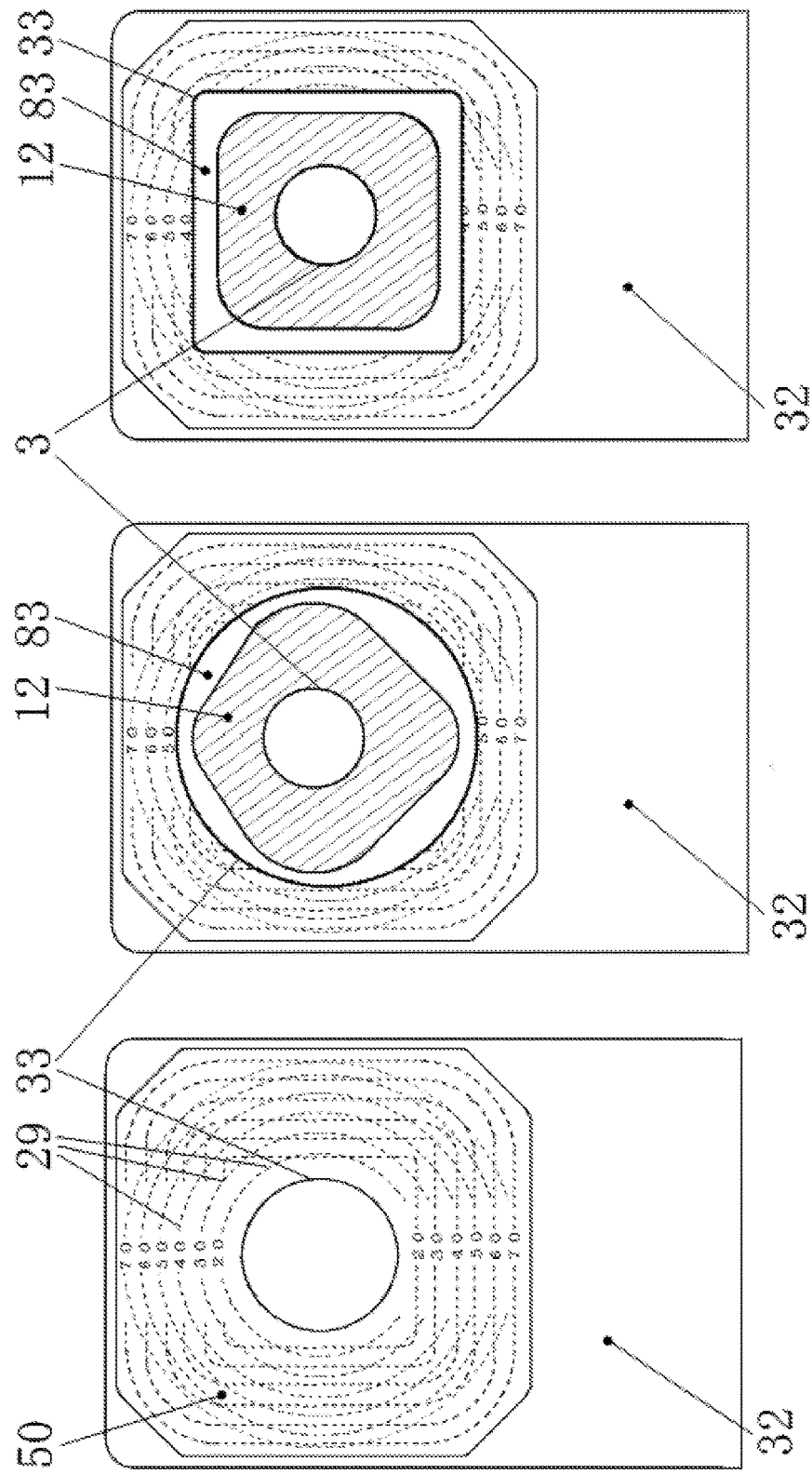

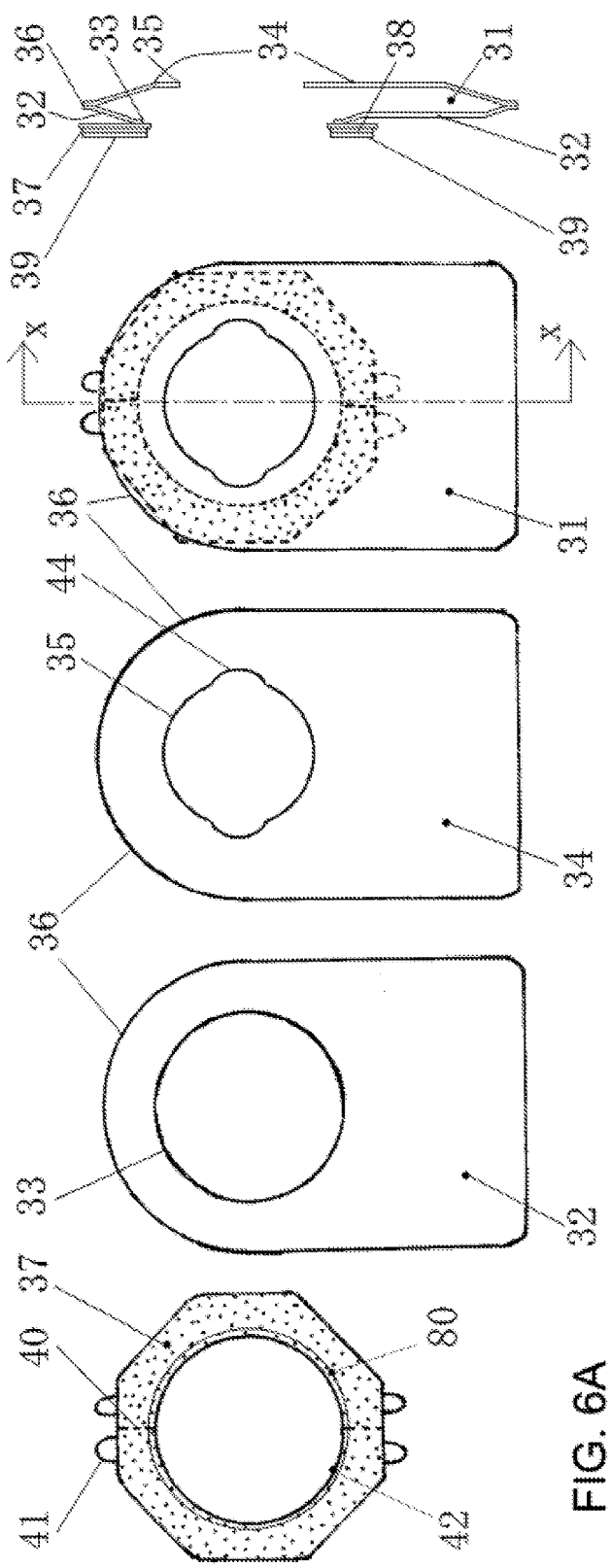

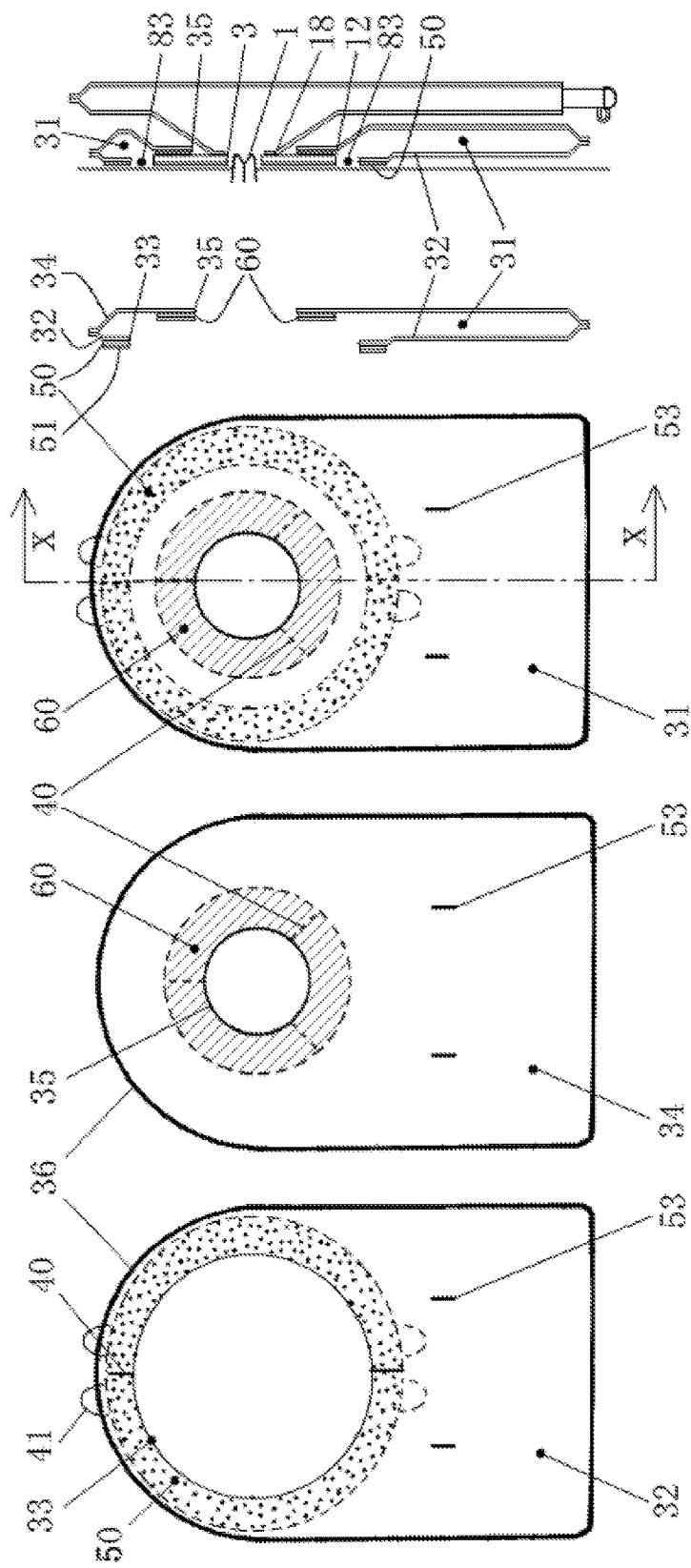

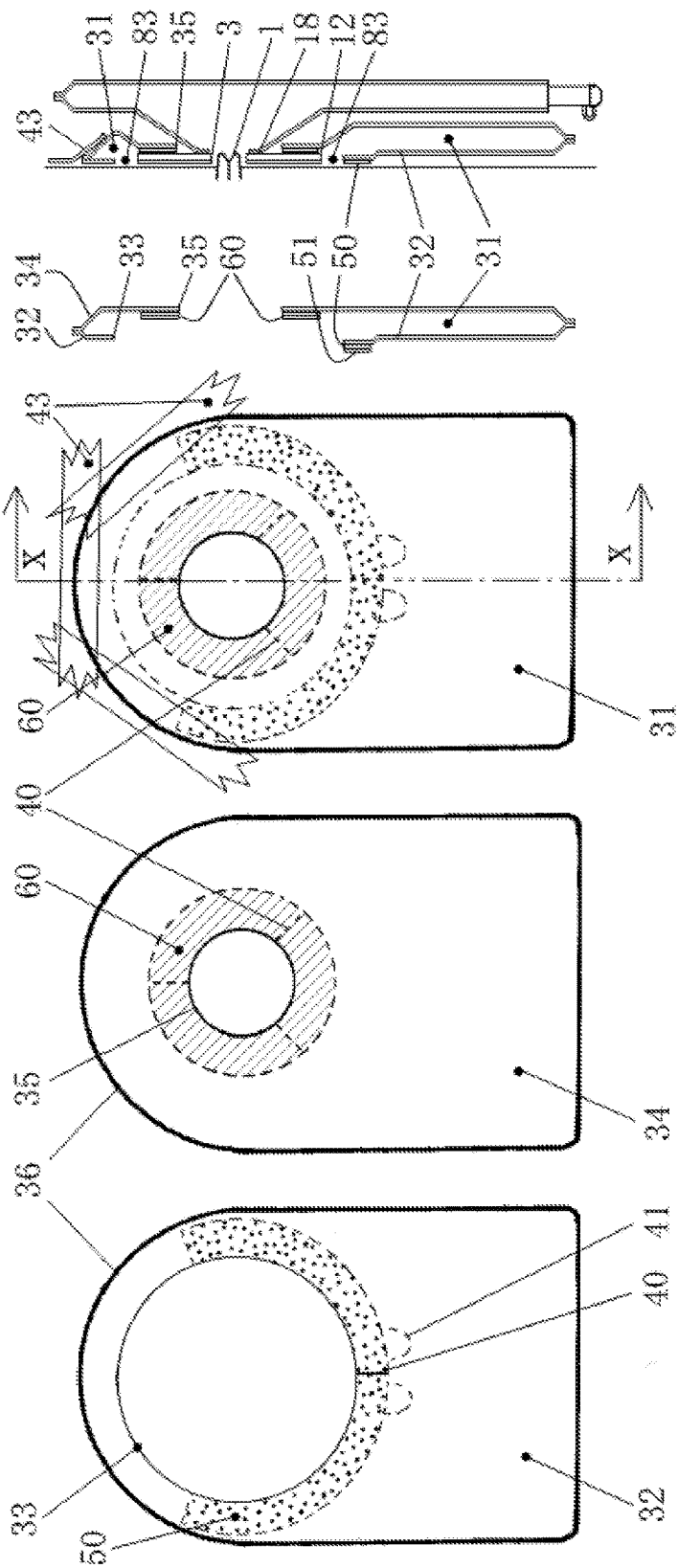

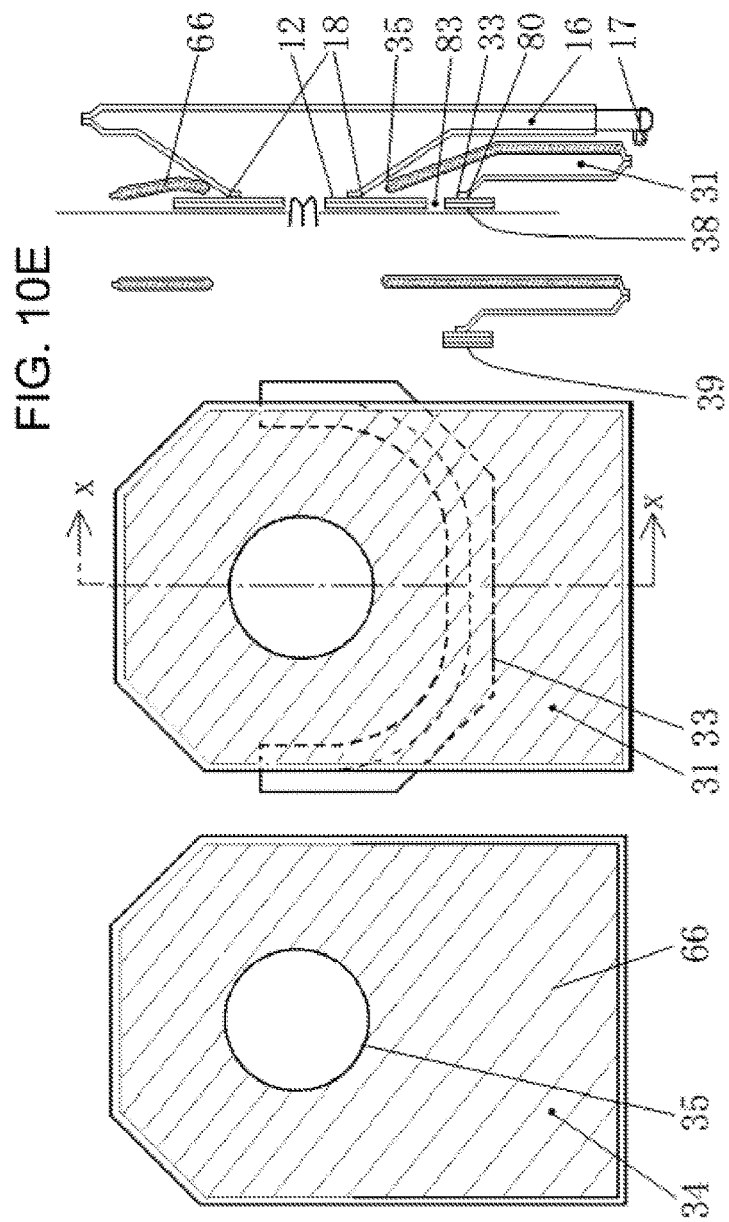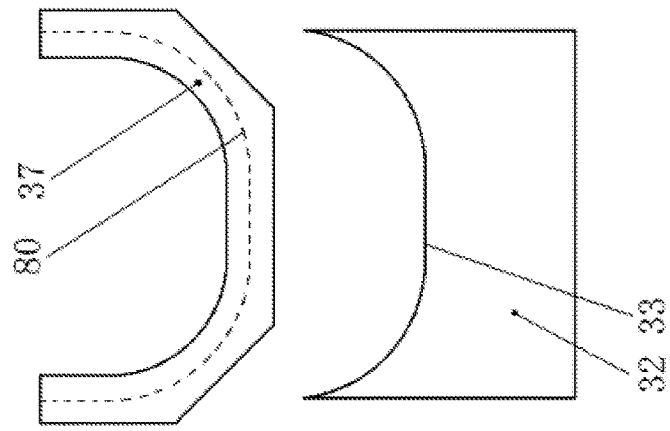

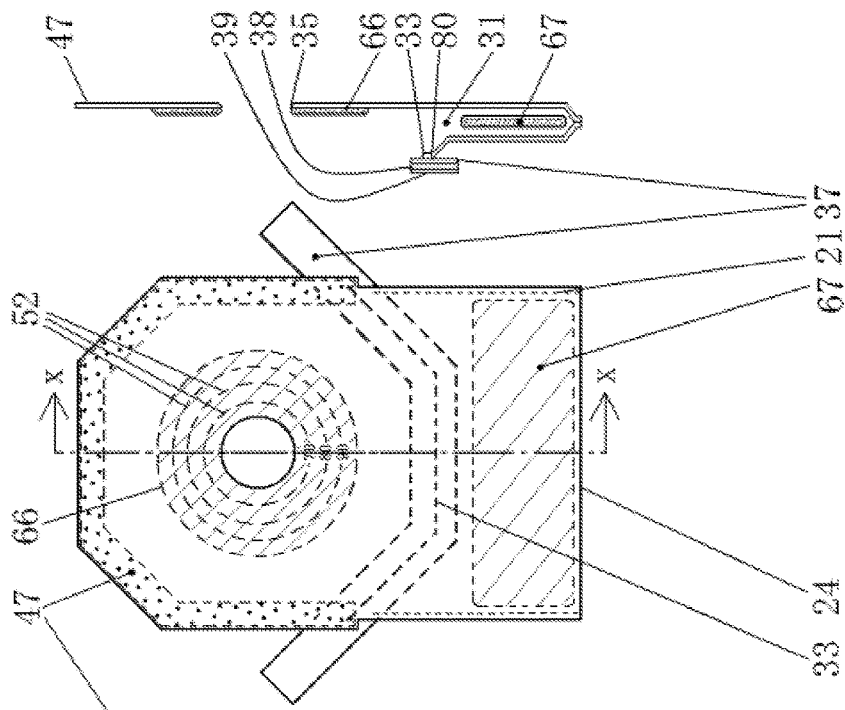
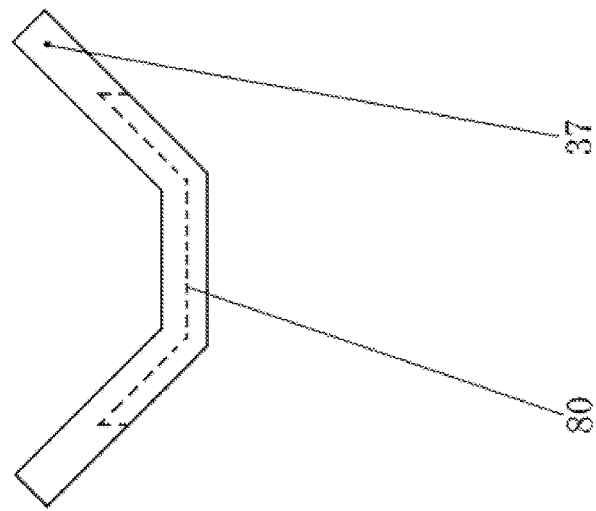

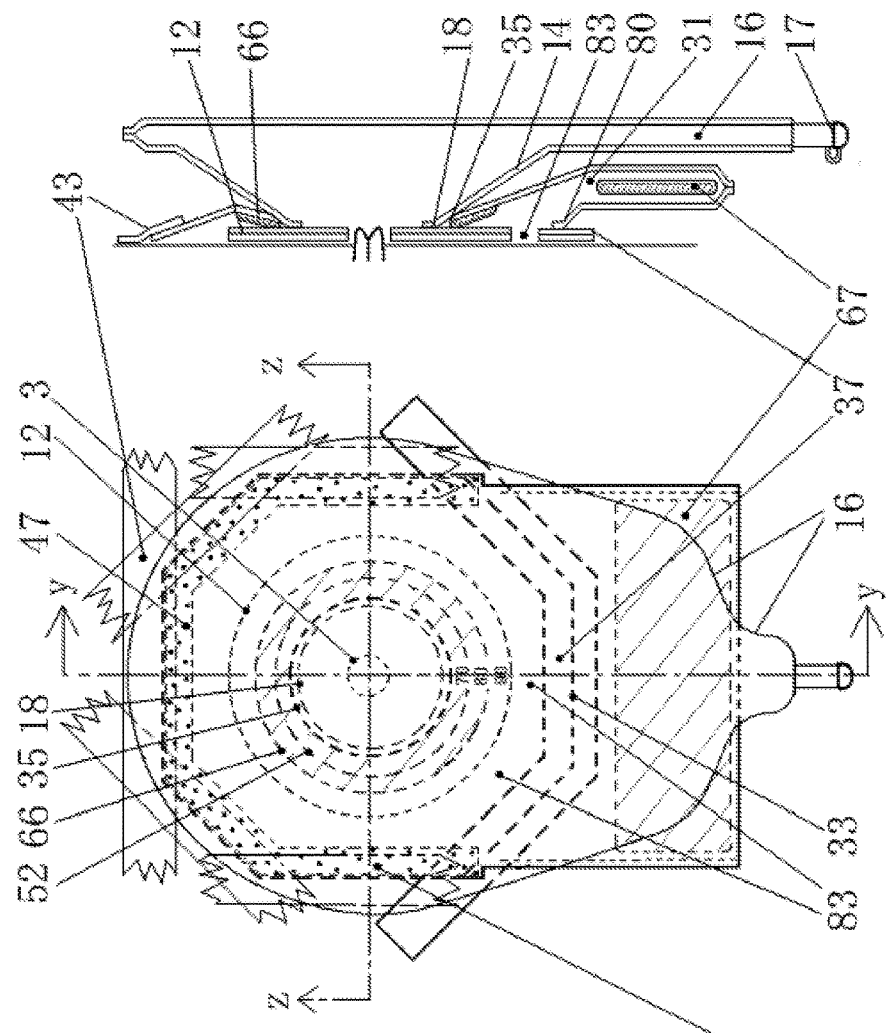
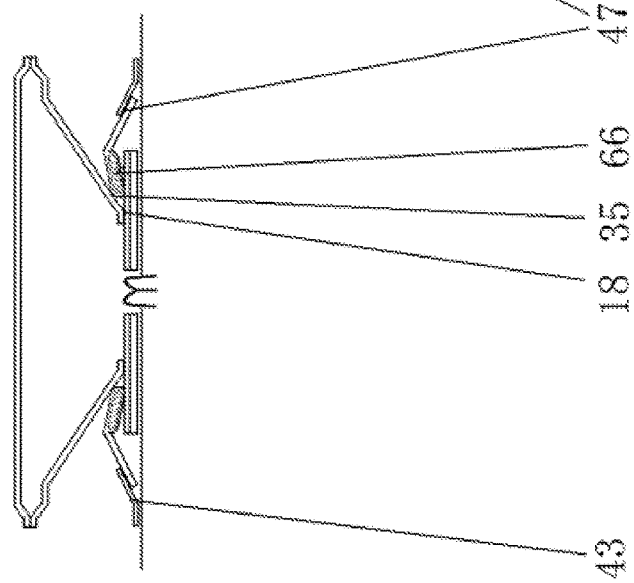
FIG. 12A  FIG. 12B  FIG. 12C

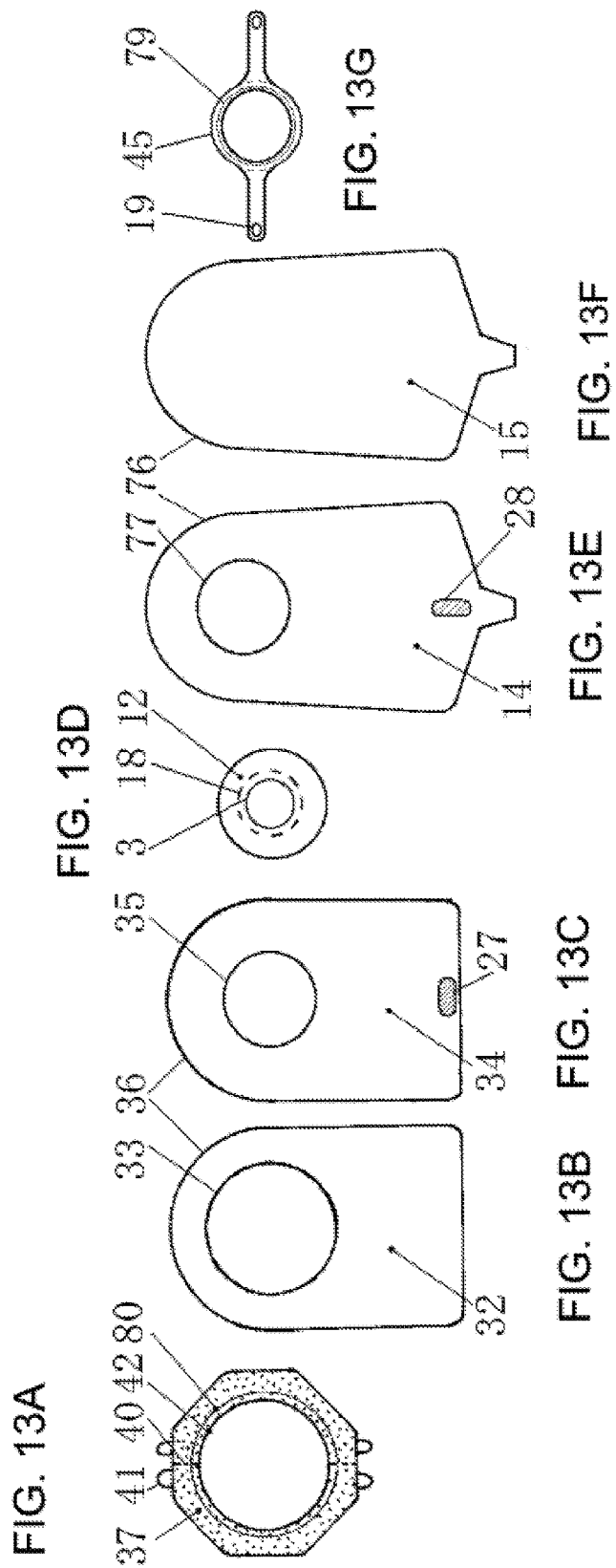

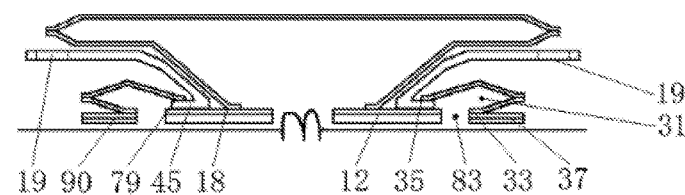
FIG. 14C
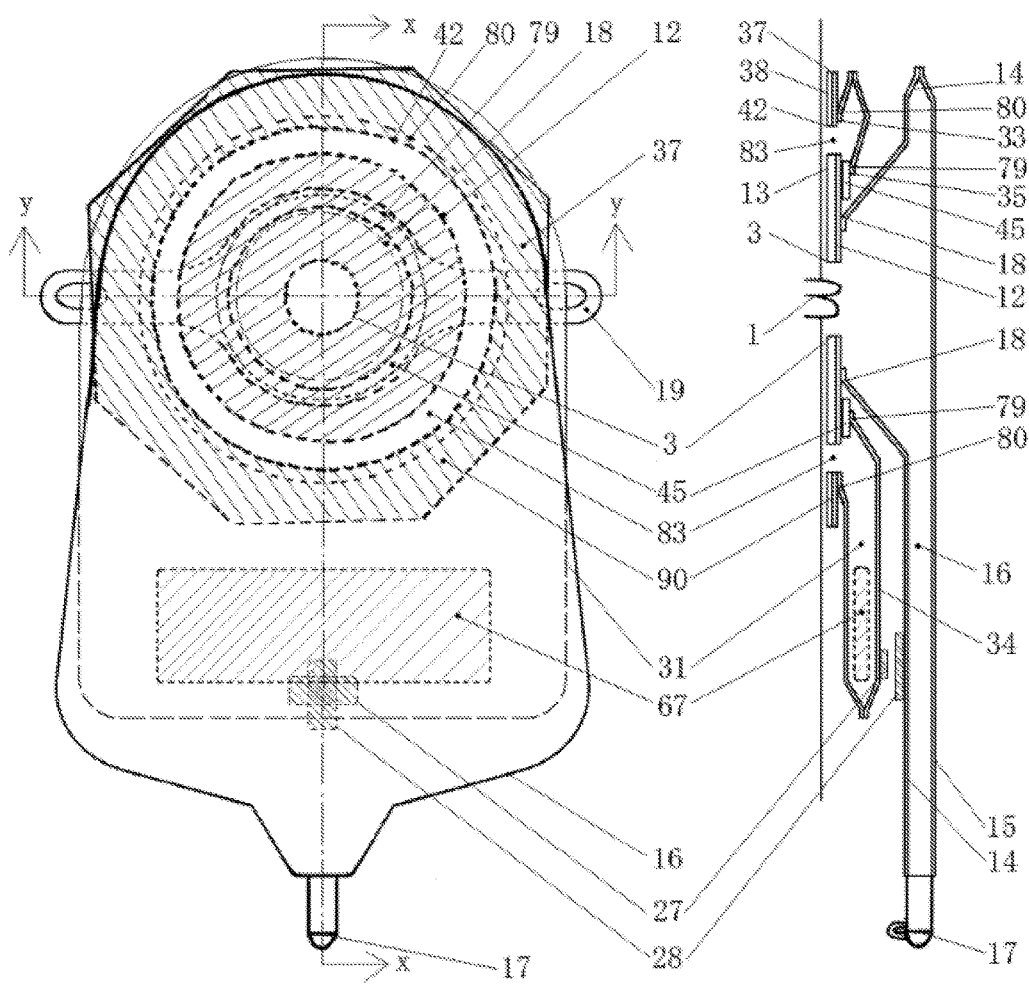
FIG. 14A
FIG. 14B

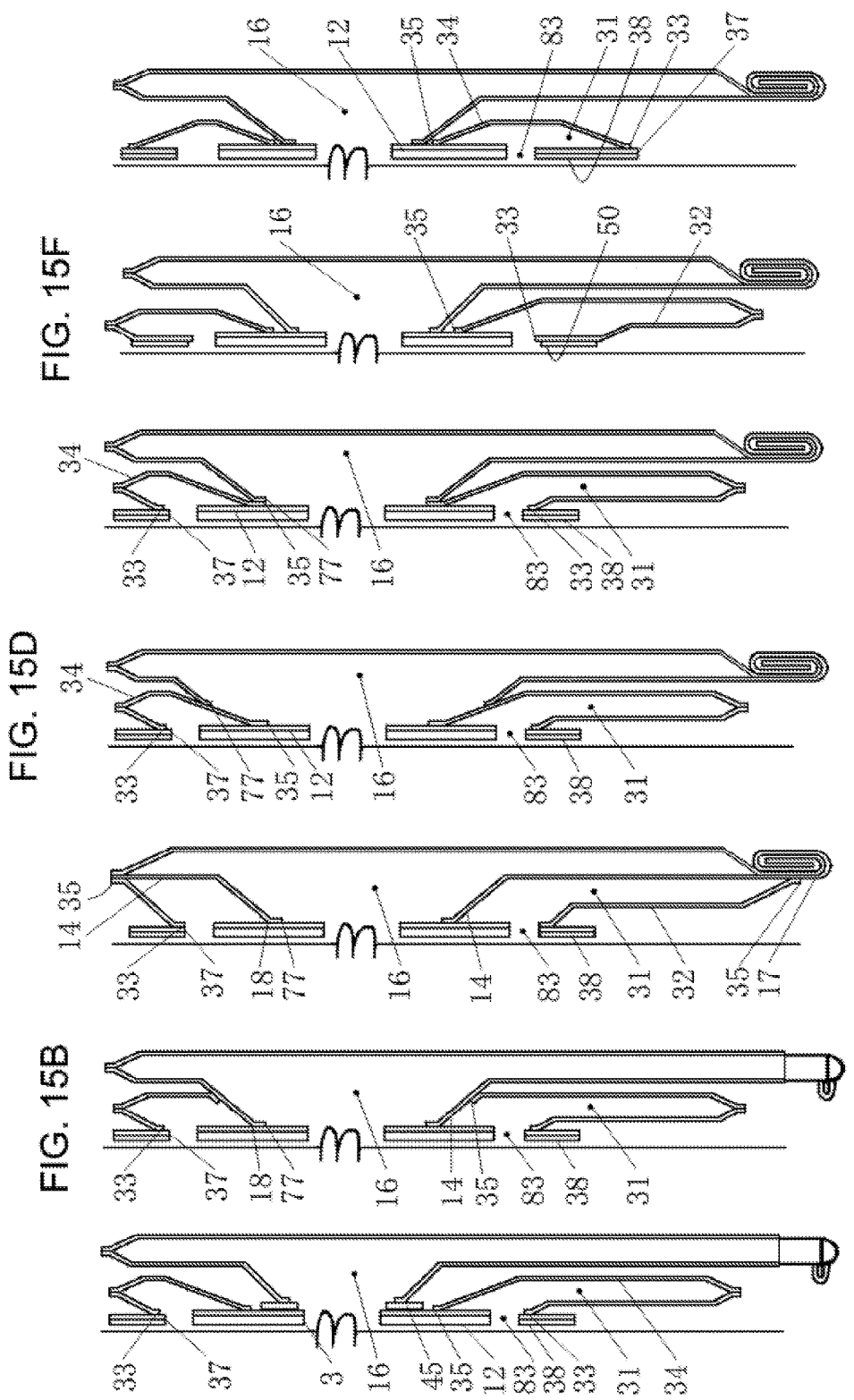

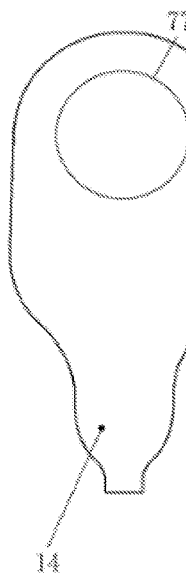
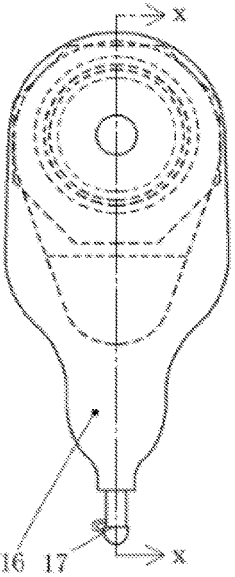
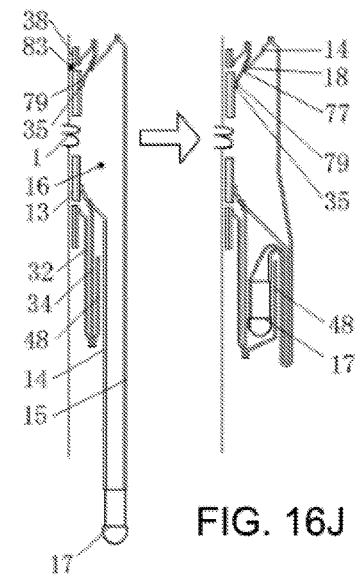
FIG. 16F   FIG. 16G   FIG. 16H   FIG. 16I
FIG. 16J

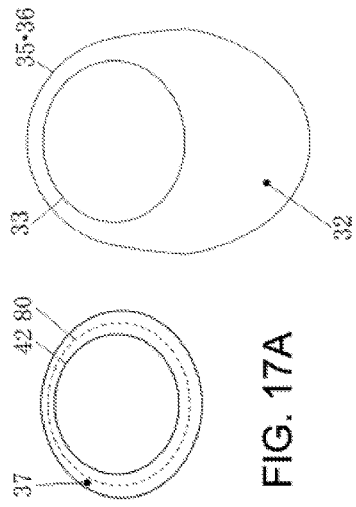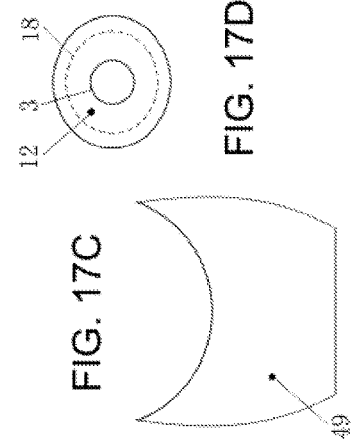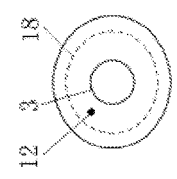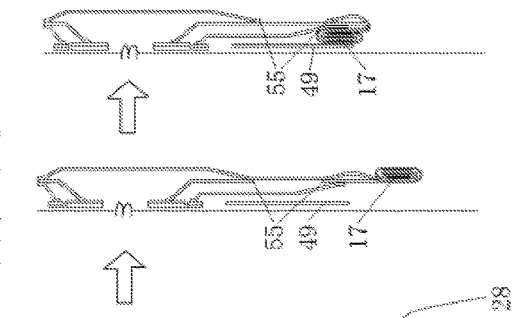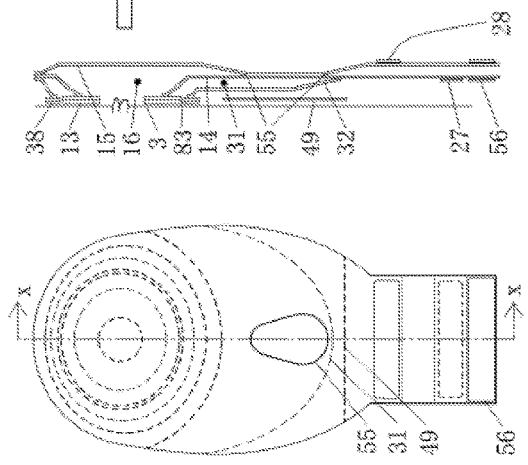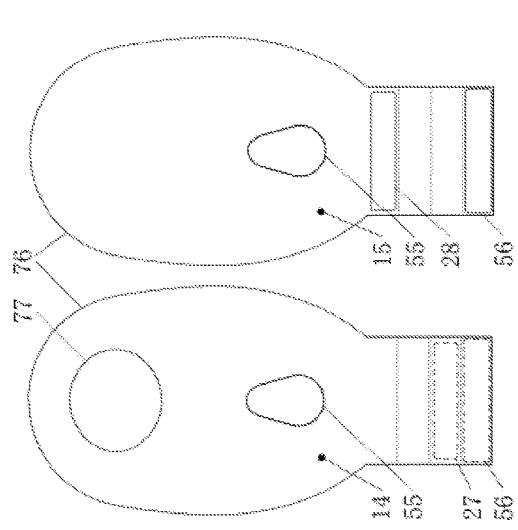

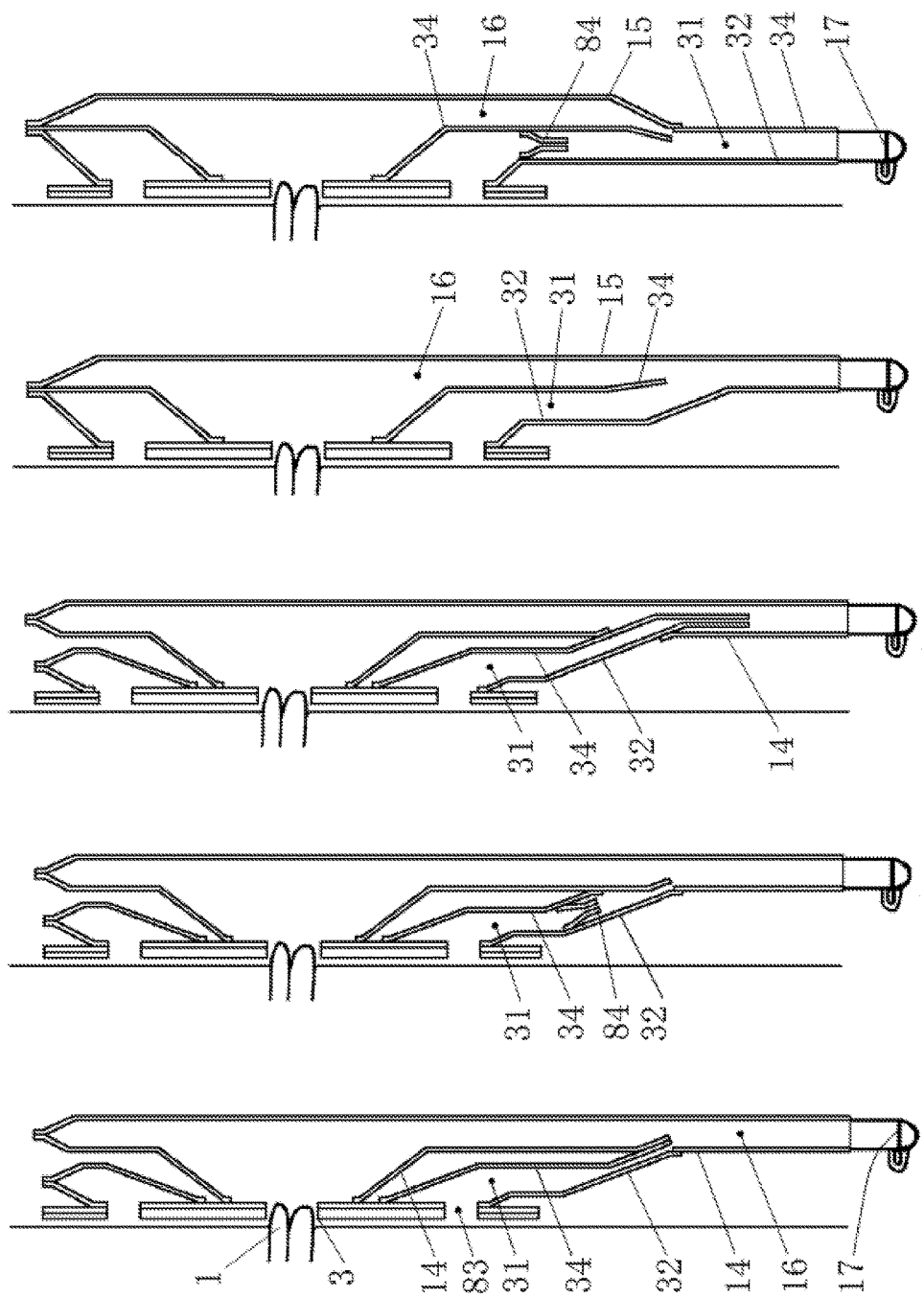

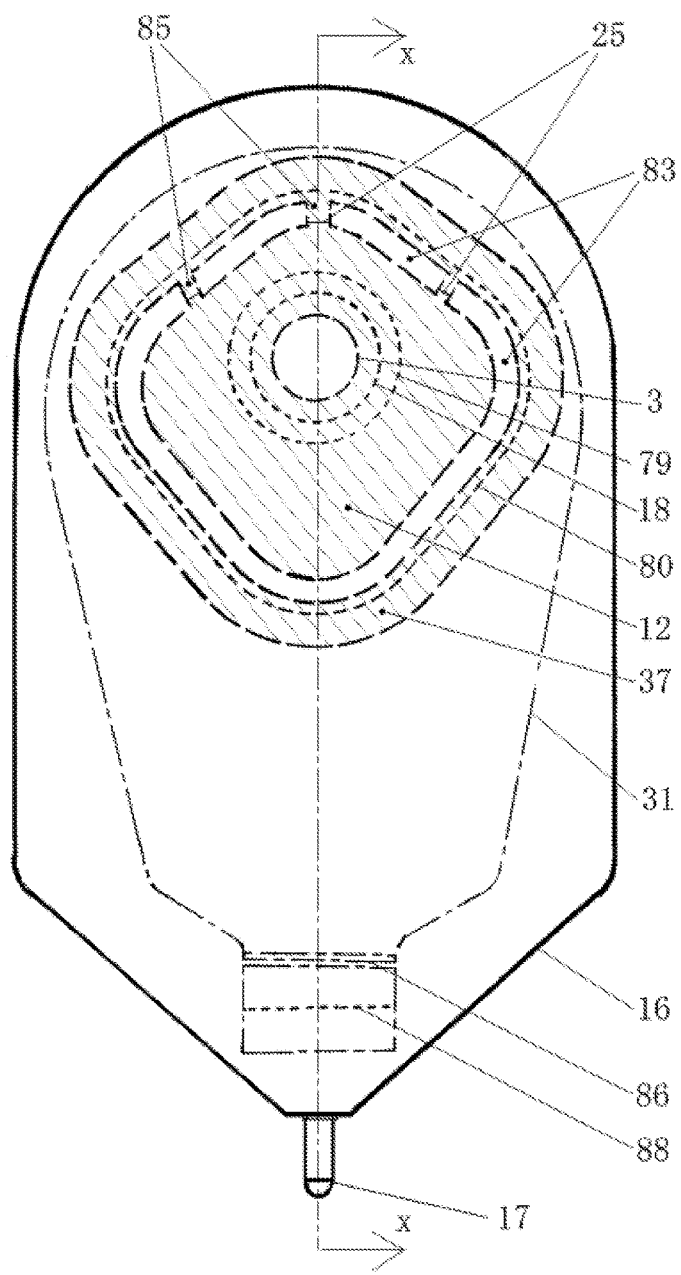
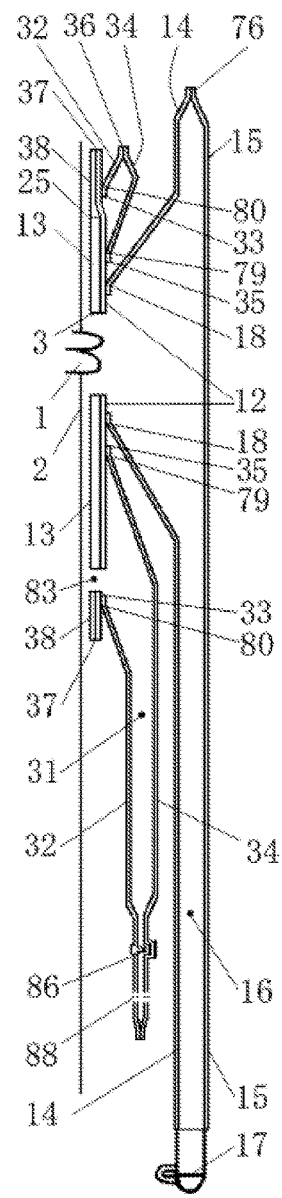
FIG. 19A
FIG. 19B

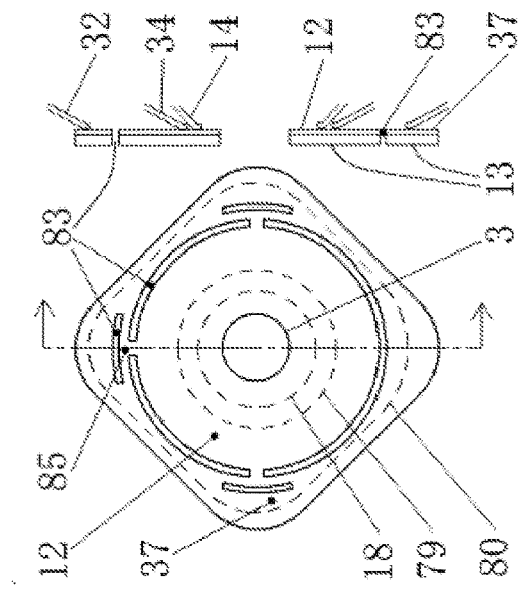
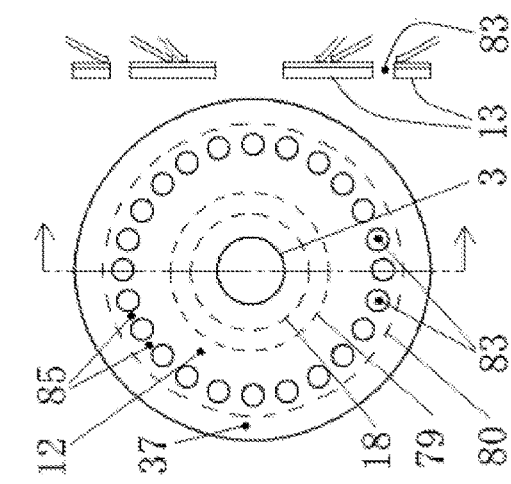
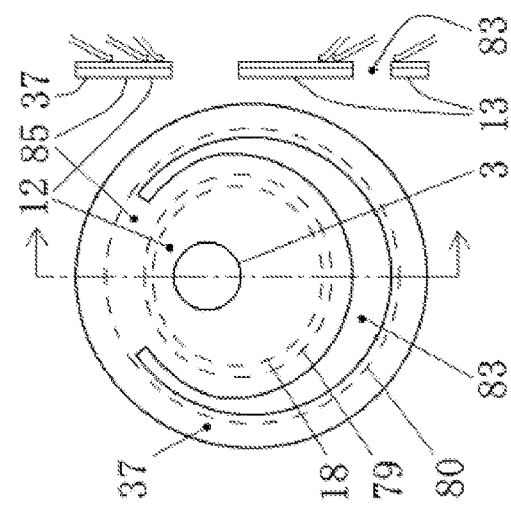

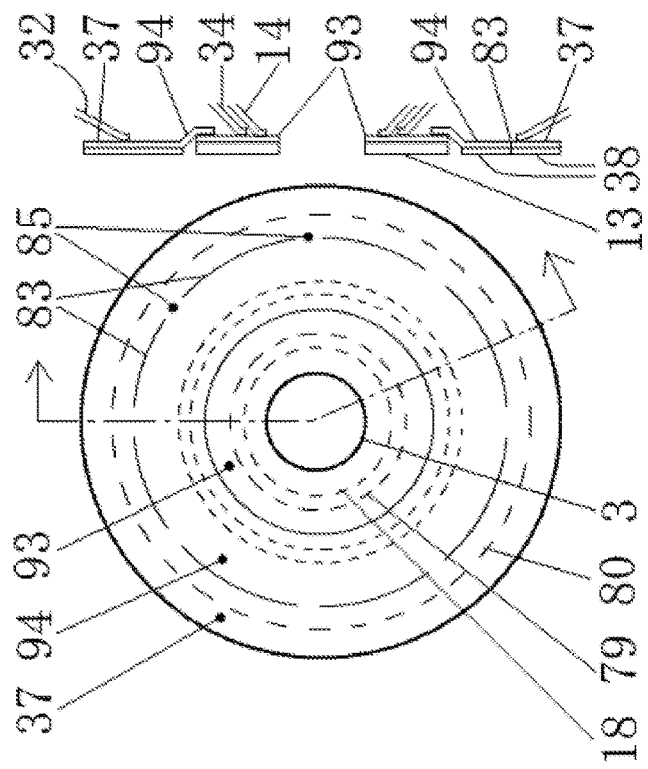
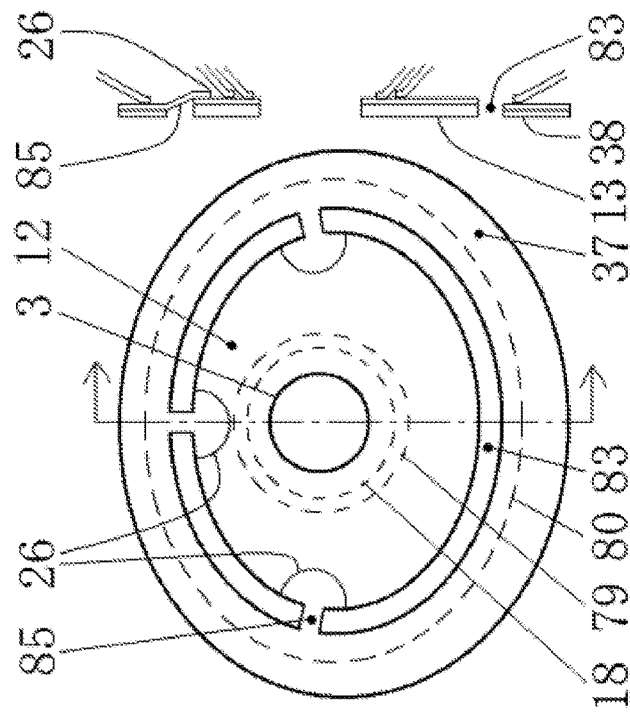

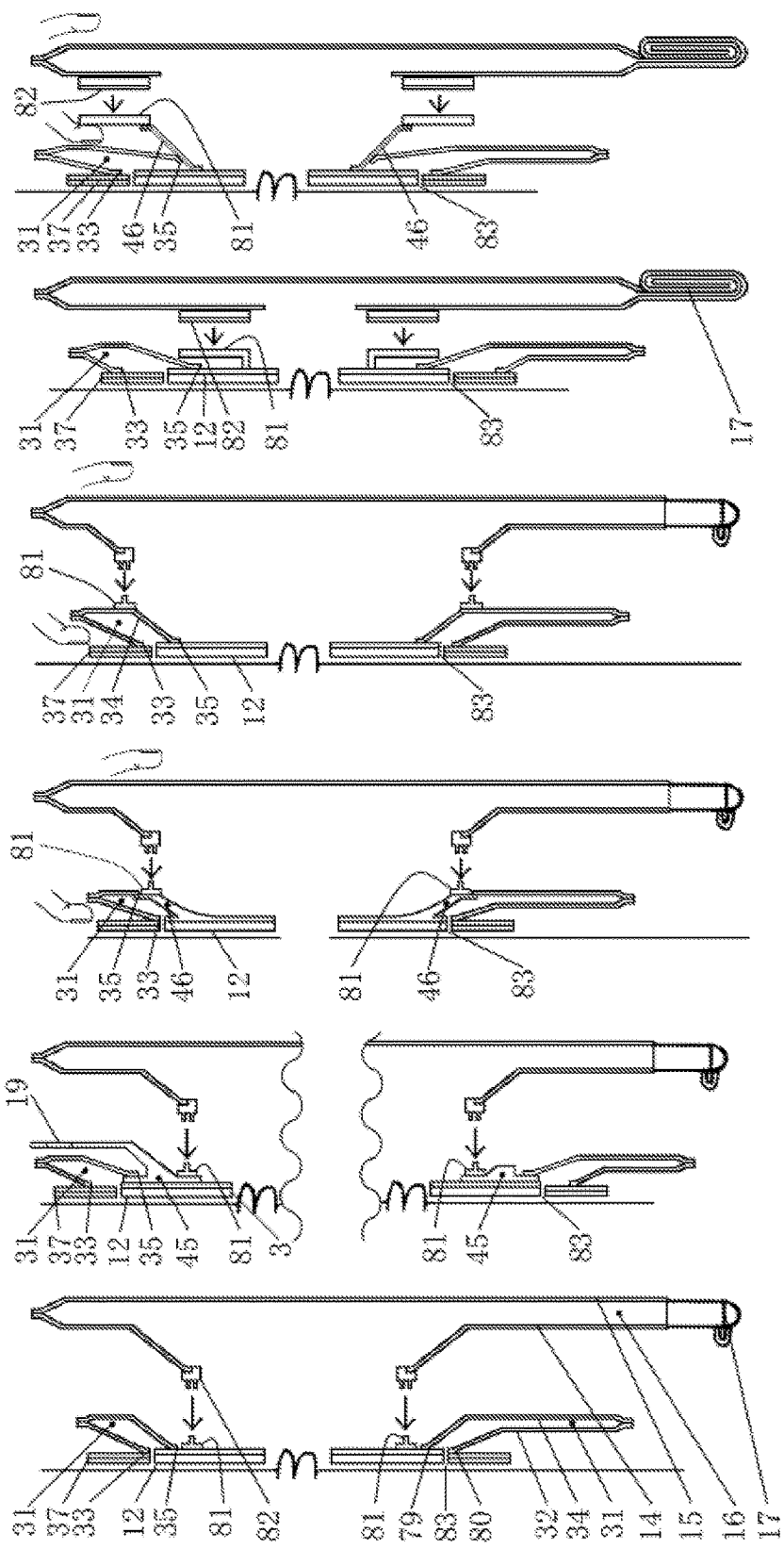

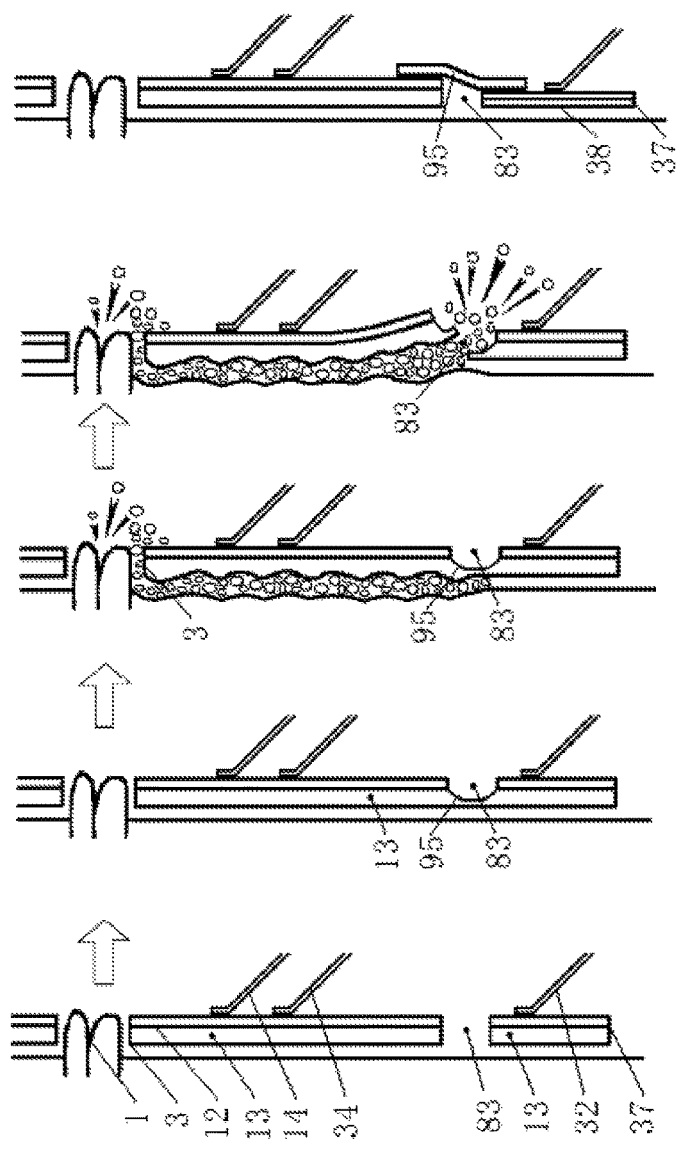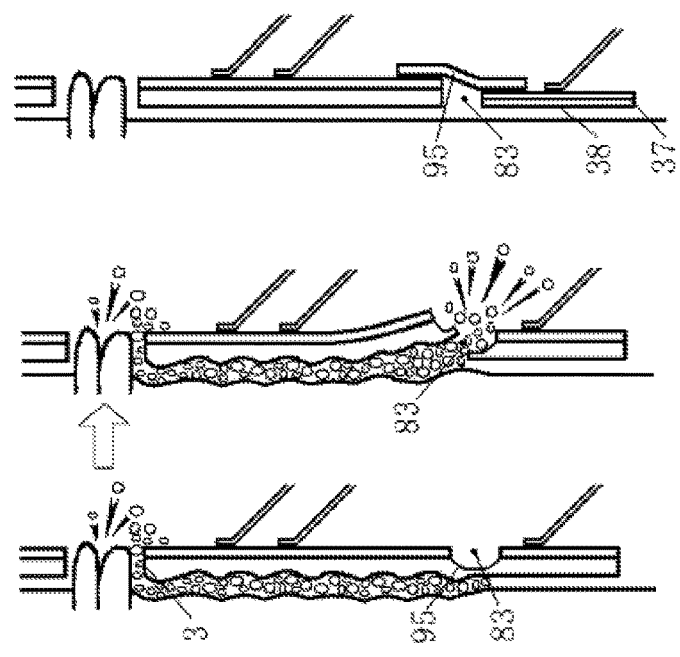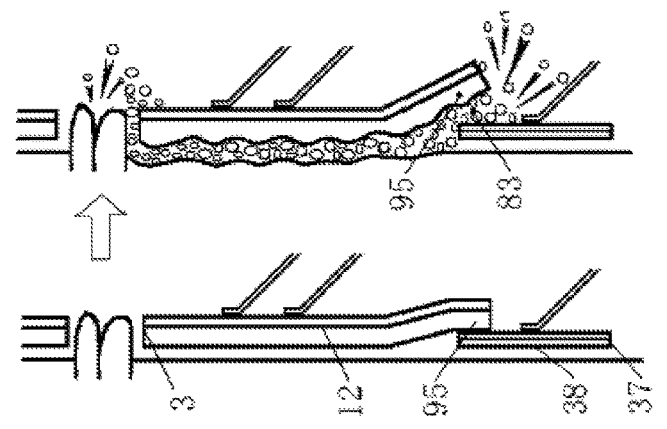

ACCOMMODATION BAG FOR STOMA APPARATUS AND STOMA APPARATUS

RELATED APPLICATIONS

This application claims priority under 35 U.S.C. § 120 to, and is a continuation of, co-pending International Application PCT/JP2015/062395, filed Apr. 23, 2015 and designating the US, which claims priority to Japanese Application 2014-137756 filed Jul. 3, 2014 and Japanese Application 2014-206852 filed Oct. 8, 2014. These Japanese and International Applications are incorporated by reference herein in its entirety.

BACKGROUND

An ostomate, whom a stoma is provided in abdomen as a result of diseases in gastrointestinal tract or urinary tract, wears an ostomy appliance in abdomen to put the one's excrement therein. Sometimes, the excrement penetrates an area between its faceplate and the one's skin, and leaks out. This phenomenon is referred to as blowout. In case of blowout, a clothing and a bedding are wasted as well as the one's skin is exposed to the excrement, causing a skin disorder to diffuse. Thus, it often results in being caught in a vicious circle of repeatedly blowing out. Further, if it blows out, people around the ostomate gets annoyed, causing serious problems in preventing young people from an advance into society and accelerating aging of old people who holds back going out. Since various reasons causes blowout, no ostomy appliance is developed that allows prediction or prevention of the blowout. Further, no ostomy appliance is developed that surely prevents the excrement leaked out from externally spreading out.

This phenomenon is described further in Japanese Unexamined Application Publication No. 2006-095321 published Apr. 13, 2006; Japanese Unexamined Application Publication No. 2004-113793 published Apr. 15, 2004; and Japanese Unexamined Application Publication No. 2009-254719 published Nov. 5, 2009, all of which are hereby incorporated by reference in their entireties.

SUMMARY

Example embodiments include ostomy appliances including a faceplate with an opening for capturing human waste from a stoma and storing the same in a storage bag. An adhesion unit forms a hole along a circumference of the faceplate, and an auxiliary storage bag then stores excrement leaking between the faceplate and skin of an ostomate. The auxiliary storage bag can be coupled to the adhesion unit so as to envelop the receiving hole. Example embodiments may allow the excrement to enter the auxiliary storage bag through an entrance hole when the excrement under the faceplate reaches near its circumference or reaches the circumference of the faceplate to blowout, preventing the excrement from externally spreading out. This permits visual confirmation of the excrement held in the auxiliary storage bag to easily realize the fact of blowout. External spreading of the excrement due to blowout is prevented, and thus contamination of clothing and bedding is avoided. Example embodiments may be mass-produced with no special production technology because the structure is relatively simple and inexpensive.

BRIEF DESCRIPTIONS OF THE DRAWINGS

Example embodiments will become more apparent by describing, in detail, the attached drawings, wherein like elements are represented by like reference numerals, which are given by way of illustration only and thus do not limit the example embodiments herein.

FIG. 1A shows a view of an auxiliary storage bag for an ostomy appliance according to a first example embodiment.

FIG. 1B shows another view of an auxiliary storage bag for an ostomy appliance according to a first example embodiment.

FIG. 1C shows another view of an auxiliary storage bag for an ostomy appliance according to a first example embodiment.

FIG. 1D shows another view of an auxiliary storage bag for an ostomy appliance according to a first example embodiment.

FIG. 1E shows another view of an auxiliary storage bag for an ostomy appliance according to a first example embodiment.

FIG. 2A shows a view of a wearing state of an auxiliary storage bag for an ostomy appliance installed to the ostomy appliance according to the first example embodiment.

FIG. 2B shows another view of a wearing state of an auxiliary storage bag for an ostomy appliance installed to the ostomy appliance according to the first example embodiment.

FIG. 2C shows another view of a wearing state of an auxiliary storage bag for an ostomy appliance installed to the ostomy appliance according to the first example embodiment.

FIG. 2D shows another view of a wearing state of an auxiliary storage bag for an ostomy appliance installed to the ostomy appliance according to the first example embodiment.

FIG. 3A shows a view of an auxiliary storage bag for an ostomy appliance according to a second example embodiment.

FIG. 3B shows another view of an auxiliary storage bag for an ostomy appliance according to a second example embodiment.

FIG. 3C shows another view of an auxiliary storage bag for an ostomy appliance according to a second example embodiment.

FIG. 3D shows another view of an auxiliary storage bag for an ostomy appliance according to a second example embodiment.

FIG. 5A shows a view of development of an inner film of the auxiliary storage bag according to the second example embodiment.

FIG. 5B shows another view of development of an inner film of the auxiliary storage bag according to the second example embodiment.

FIG. 5C shows another view of development of an inner film of the auxiliary storage bag according to the second example embodiment.

FIG. 6A shows a view of an auxiliary storage bag for an ostomy appliance according to a third example embodiment.

FIG. 6B shows another view of an auxiliary storage bag for an ostomy appliance according to the third example embodiment.

FIG. 6C shows another view of an auxiliary storage bag for an ostomy appliance according to the third example embodiment.

FIG. 6D shows another view of an auxiliary storage bag for an ostomy appliance according to the third example embodiment.

FIG. 6E shows another view of an auxiliary storage bag for an ostomy appliance according to a third example embodiment.

FIG. 8A shows a view of an auxiliary storage bag for an ostomy appliance according to a fourth example embodiment.

FIG. 8B shows another view of an auxiliary storage bag for an ostomy appliance according to the fourth example embodiment.

FIG. 8C shows another view of an auxiliary storage bag for an ostomy appliance according to the fourth example embodiment.

FIG. 8D shows another view of an auxiliary storage bag for an ostomy appliance according to the fourth example embodiment.

FIG. 8E shows another view of an auxiliary storage bag for an ostomy appliance according to the fourth example embodiment.

FIG. 9A shows a view of an auxiliary storage bag for an ostomy appliance according to a fifth example embodiment.

FIG. 9B shows another view of an auxiliary storage bag for an ostomy appliance according to the fifth example embodiment.

FIG. 9C shows another view of an auxiliary storage bag for an ostomy appliance according to the fifth example embodiment.

FIG. 9D shows another view of an auxiliary storage bag for an ostomy appliance according to the fifth example embodiment.

FIG. 9E shows another view of an auxiliary storage bag for an ostomy appliance according to the fifth example embodiment.

FIG. 10A shows a view of an auxiliary storage bag for an ostomy appliance according to a sixth example embodiment.

FIG. 10B shows another view of an auxiliary storage bag for an ostomy appliance according to the sixth example embodiment.

FIG. 10C shows another view of an auxiliary storage bag for an ostomy appliance according to the sixth example embodiment.

FIG. 10D shows another view of an auxiliary storage bag for an ostomy appliance according to the sixth example embodiment.

FIG. 10E shows another view of an auxiliary storage bag for an ostomy appliance according to the sixth example embodiment.

FIG. 10F shows another view of an auxiliary storage bag for an ostomy appliance according to the sixth example embodiment.

FIG. 11A shows a view of an auxiliary storage bag for an ostomy appliance according to a seventh example embodiment.

FIG. 11B shows another view of an auxiliary storage bag for an ostomy appliance according to the seventh example embodiment.

FIG. 11C shows another view of an auxiliary storage bag for an ostomy appliance according to the seventh example embodiment.

FIG. 11D shows another view of an auxiliary storage bag for an ostomy appliance according to the seventh example embodiment.

FIG. 12A shows a view of wearing an auxiliary storage bag for an ostomy appliance according to the seventh example embodiment.

FIG. 12B shows another view of wearing an auxiliary storage bag for an ostomy appliance according to the seventh example embodiment.

FIG. 12C shows another view of wearing an auxiliary storage bag for an ostomy appliance according to the seventh example embodiment.

FIG. 13A shows a view of an ostomy appliance integrating an auxiliary storage bag according to an eighth example embodiment.

FIG. 13B shows another view of an ostomy appliance integrating an auxiliary storage bag according to the eighth example embodiment.

FIG. 13C shows another view of an ostomy appliance integrating an auxiliary storage bag according to the eighth example embodiment.

FIG. 13D shows another view of an ostomy appliance integrating an auxiliary storage bag according to the eighth example embodiment.

FIG. 13E shows another view of an ostomy appliance integrating an auxiliary storage bag according to the eighth example embodiment.

FIG. 13F shows another view of an ostomy appliance integrating an auxiliary storage bag according to the eighth example embodiment.

FIG. 13G shows another view of an ostomy appliance integrating an auxiliary storage bag according to the eighth example embodiment.

FIG. 14A shows a view of a wearing state of an ostomy appliance integrating an auxiliary storage bag according to the eighth example embodiment.

FIG. 14B shows another view of a wearing state of an ostomy appliance integrating an auxiliary storage bag according to the eighth example embodiment.

FIG. 14C shows another view of a wearing state of an ostomy appliance integrating an auxiliary storage bag according to the eighth example embodiment.

FIG. 15A shows a view of a development of an ostomy appliance integrating an auxiliary storage bag according to the eighth example embodiment.

FIG. 15B shows another view of a development of an ostomy appliance integrating an auxiliary storage bag according to the eighth example embodiment.

FIG. 15C shows another view of a development of an ostomy appliance integrating an auxiliary storage bag according to the eighth example embodiment.

FIG. 15D shows another view of a development of an ostomy appliance integrating an auxiliary storage bag according to the eighth example embodiment.

FIG. 15E shows another view of a development of an ostomy appliance integrating an auxiliary storage bag according to the eighth example embodiment.

FIG. 15F shows another view of a development of an ostomy appliance integrating an auxiliary storage bag according to the eighth example embodiment.

FIG. 15G shows another view of a development of an ostomy appliance integrating an auxiliary storage bag according to the eighth example embodiment.

FIG. 16F shows another view of providing a pocket with an integrated ostomy appliance according to the ninth example embodiment.

FIG. 16G shows another view of providing a pocket with an integrated ostomy appliance according to the ninth example embodiment.

FIG. 16H is shows another view of providing a pocket with an integrated ostomy appliance according to the ninth example embodiment.

FIG. 16I is shows another view of providing a pocket with an integrated ostomy appliance according to the ninth example embodiment.

FIG. 16J is shows another view of providing a pocket with an integrated ostomy appliance according to the ninth example embodiment.

FIG. 17A shows a view of providing an observation window pocket with an integrated ostomy appliance according to the ninth example embodiment.

FIG. 17B shows another view of providing an observation window pocket with an integrated ostomy appliance according to the ninth example embodiment.

FIG. 17C shows another view of providing an observation window pocket with an integrated ostomy appliance according to the ninth example embodiment.

FIG. 17D shows another view of providing an observation window pocket with an integrated ostomy appliance according to the ninth example embodiment.

FIG. 17E shows another view of providing an observation window pocket with an integrated ostomy appliance according to the ninth example embodiment.

FIG. 17F shows another view of providing an observation window pocket with an integrated ostomy appliance according to the ninth example embodiment.

FIG. 17G shows another view of providing an observation window pocket with an integrated ostomy appliance according to the ninth example embodiment.

FIG. 17H shows another view of providing an observation window pocket with an integrated ostomy appliance according to the ninth example embodiment.

FIG. 17I shows another view of providing an observation window pocket with an integrated ostomy appliance according to the ninth example embodiment.

FIG. 17J shows another view of providing an observation window pocket with an integrated ostomy appliance according to the ninth example embodiment.

FIG. 18A shows a view of a development example of an ostomy appliance that penetrate a bag and an auxiliary storage bag according to a tenth example embodiment.

FIG. 18B shows another view of a development example of an ostomy appliance that penetrate a bag and an auxiliary storage bag according to the tenth example embodiment.

FIG. 18C shows another view of a development example of an ostomy appliance that penetrate a bag and an auxiliary storage bag according to the tenth example embodiment.

FIG. 18D shows another view of a development example of an ostomy appliance that penetrate a bag and an auxiliary storage bag according to the tenth example embodiment.

FIG. 18E shows another view of a development example of an ostomy appliance that penetrate a bag and an auxiliary storage bag according to the tenth example embodiment.

FIG. 19A is a view of coupling an adhesion unit with a faceplate of the ostomy appliance according to an eleventh example embodiment.

FIG. 19B is another view of coupling an adhesion unit with a faceplate of the ostomy appliance according to the eleventh example embodiment.

FIG. 20A is a view of partially coupling an adhesion unit with a faceplate according to the eleventh example embodiment.

FIG. 20B is another view of partially coupling an adhesion unit with a faceplate according to the eleventh example embodiment.

FIG. 20C is another view of partially coupling an adhesion unit with a faceplate according to the eleventh example embodiment.

FIG. 20D is another view of partially coupling an adhesion unit with a faceplate according to the eleventh example embodiment.

FIG. 20E is another view of partially coupling an adhesion unit with a faceplate according to the eleventh example embodiment.

FIG. 20F is another view of partially coupling an adhesion unit with a faceplate according to the eleventh example embodiment.

FIG. 21A is a view of partially coupling an adhesion unit with a faceplate according to the eleventh example embodiment.

FIG. 21B is another view of partially coupling an adhesion unit with a faceplate according to the eleventh example embodiment.

FIG. 21C is another view of partially coupling an adhesion unit with a faceplate according to the eleventh example embodiment.

FIG. 21D is another view of partially coupling an adhesion unit with a faceplate according to the eleventh example embodiment.

FIG. 24A shows a view of a development example of a two-piece ostomy system having an auxiliary storage bag according to the thirteenth example embodiment.

FIG. 24B shows another view of a development example of a two-piece ostomy system having an auxiliary storage bag according to the thirteenth example embodiment.

FIG. 24C shows another view of a development example of a two-piece ostomy system having an auxiliary storage bag according to the thirteenth example embodiment.

FIG. 24D shows another view of a development example of a two-piece ostomy system having an auxiliary storage bag according to the thirteenth example embodiment.

FIG. 24E shows another view of a development example of a two-piece ostomy system having an auxiliary storage bag according to the thirteenth example embodiment.

FIG. 24F shows another view of a development example of a two-piece ostomy system having an auxiliary storage bag according to the thirteenth example embodiment.

FIG. 27A is a view of an ostomy appliance on which a member for fixing positions according to a fifteenth example embodiment.

FIG. 27B is another view of an ostomy appliance on which a member for fixing positions according to the fifteenth example embodiment.

FIG. 27C is another view of an ostomy appliance on which a member for fixing positions according to the fifteenth example embodiment.

FIG. 27D is another view of an ostomy appliance on which a member for fixing positions according to the fifteenth example embodiment.

FIG. 27E is another view of an ostomy appliance on which a member for fixing positions according to the fifteenth example embodiment.

FIG. 27F is another view of an ostomy appliance on which a member for fixing positions according to the fifteenth example embodiment.

FIG. 27G is another view of an ostomy appliance on which a member for fixing positions according to the fifteenth example embodiment.

DETAILED DESCRIPTION

Figure 4A:
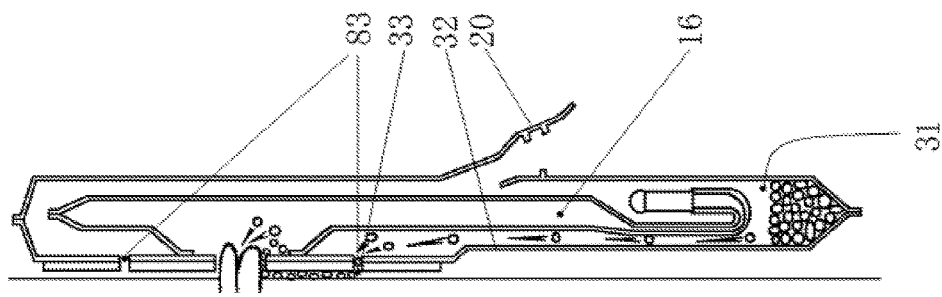
FIG. 4A shows a view of functioning of attachment to existing ostomy appliance according to the second example embodiment.

Because this is a patent document, general broad rules of construction should be applied when reading it. Everything described and shown in this document is an example of subject matter falling within the scope of the claims, appended below. Any specific structural and functional details disclosed herein are merely for purposes of describing how to make and use example embodiments. Several different embodiments not specifically disclosed herein may fall within the claim scope; as such, the claims may be embodied in many alternate forms and should not be construed as limited to only example embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, "and" and "or" are equivalent to the term "and/or," which includes any and all combinations of one or more of the associated listed items.

It will be understood that when an element is referred to as being "connected," "coupled," "mated," "attached," or "fixed" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.). Similarly, a term such as "communicatively connected" includes all variations of information exchange routes between two devices, including intermediary devices, networks, etc., connected wirelessly or not.

As used herein, the singular forms "a", "an" and "the" and the plural form "indicia" are intended to include both the singular and plural forms, unless the language explicitly indicates otherwise. It will be further understood that the terms "comprises," "comprising," "includes," and/or "including," when used herein, specify the presence of stated features, integers, steps, operations, elements, and/or components, but do not themselves preclude the presence or addition of one or more other features, integers, steps, operations, elements, components, and/or groups thereof.

It should also be noted that the structures and operations discussed below may occur out of the order described and/or noted in the figures. For example, two operations and/or figures shown in succession may in fact be executed concurrently or may sometimes be executed in the reverse order, depending upon the functionality/acts involved. Similarly, individual operations within example methods described below may be executed repetitively, individually or sequentially, so as to provide looping or other series of operations aside from the single operations described below. It should be presumed that any embodiment having features and functionality described below, in any workable combination, falls within the scope of example embodiments.

The inventor has recognized that the ostomy appliance generally blows out. In view of the blowout, an auxiliary storage bag is provided to put the excrement of blowout in the auxiliary storage bag, preventing the excrement from externally spreading out. In other words, when the excrement enters under the faceplate and reaches near its circumference or reaches the circumference of the faceplate to blowout, it is possible to allow the excrement to enter the auxiliary storage bag through an entrance hole. As a result, leakage of the excrement is prevented and the blowout decreases a pressure caused by the excrement, so that a further advancement in a lateral direction is inhibited.

Further, the Inventor has recognized that entry of the excrement in the auxiliary storage bag is a signal of occurrence of blowout. In other words, the auxiliary storage bag works as a device notifying a limitation of using the ostomy appliance, allowing the ostomate to know the blowout in order to renew the ostomy appliance. In less time, the skin becomes exposed by the excrement, allowing the skin problem to be avoided from spreading. If the skin disorder is improved, a virtuous cycle is expected that a skin protection agent layer becomes easier to adhere to the skin and harder to blow out.

Many ostomates wish development of an ostomy appliance hard to blow out that prevents the excrement from spreading in case of blowout like this and that allows timely exchange of ostomy appliances so that the healthy skin is maintained. The following patent documents depicts drawings of two storage bags, but the structure and the purpose are different.

The first problem to be solved is to prevent the excrement from spreading in case of blowout as the excrement under the faceplate reaches near its circumference of the faceplate or reaches the circumference of the faceplate.

It is intended to solve the problem of external spreading of the excrement due to blowout which is a big concern for a long time. It is intended to provide a comfortable and reassuring lives with ostomates.

To solve the above problems, an ostomy appliance according to one example embodiment comprises: a faceplate having a faceplate opening that captures excrement from a stoma into a storage bag; an adhesion unit configured to form a receiving hole against a circumference of the faceplate; and an auxiliary storage bag configured to store the excrement leaking between the faceplate and skin of an ostomate, wherein at least an edge of the auxiliary storage bag is coupled to the adhesion unit, and the auxiliary storage bag envelops the receiving hole. Further, the auxiliary storage bag for the ostomy appliance in example embodiments is the auxiliary storage bag used for the ostomy appliance. It should be notes that coupling is referred to as contacting each member to form one by, for example, methods such as thermal adhesion or solvent adhesion.

Further, an ostomy appliance according to one example embodiment comprises: a faceplate having a faceplate opening that captures excrement from a stoma into a storage bag; an adhesion unit configured to form a receiving hole against a circumference of the faceplate; and an auxiliary storage bag configured to store the excrement leaking between the faceplate and skin of an ostomate, wherein the auxiliary storage bag is provided with a first opening and a second opening, the first opening is coupled to the adhesion unit, the second opening is coupled to the faceplate, the storage bag and/or a member installed to the faceplate, and the auxiliary storage bag envelops the receiving hole.

It should be noted that the member installed to the faceplate may be a member directly installed to the faceplate e.g. a base 45 of a knob for hooking a belt or a supporter 46 of the coupling unit. Further, the outlet 17 is also included in the member installed to the faceplate. In other words, since the storage bag 16 is installed to the faceplate and the outlet is installed to the storage bag, the outlet is substantially installed to the faceplate.

Further, according to the ostomy appliance with regard to one example embodiment, the adhesion unit is at least arranged on an upper side of the faceplate, and the adhesion unit is not at least arranged on a lower side of the faceplate. This feature allows the auxiliary storage bag to be fixed to skin by the minimal adhesion unit, reducing the burden on skin.

Further, according to the ostomy appliance with regard to one example embodiment, the faceplate is partially coupled with the adhesion unit. Due to this feature, the positional relation between the faceplate and the adhesion unit becomes accurate enough to be easily and accurately installed. The portions of coupling may be one or more, and the positional fixation member 95 may be used as the coupling method. It should be noted that the shape of the receiving hole formed between the faceplate and the adhesion unit may be a slit that is the gap diameter of 0.

Further, according to the ostomy appliance with regard to one example embodiment, a positional fixation member is installed at least partially across the receiving hole, the positional fixation member being weakened in strength, melt down or released by contacting the excrement leaking between the faceplate and the skin of the ostomate. This feature prevents deformation of the receiving hole so that the ostomy appliance is easily and accurately installed.

Further, according to the ostomy appliance with regard to one example embodiment, the auxiliary storage bag is provided with a first opening and a second opening, the first opening is coupled to the adhesion unit, the second opening is coupled to the faceplate and/or a member installed to the faceplate, the auxiliary storage bag envelops the receiving hole, and a coupling member configured to detach the storage bag is coupled to the faceplate, the auxiliary storage bag and/or the member installed to the faceplate. The coupling unit may be any engagement unit having concave and convex portions, or a combination of circular flange and a disc having an adhesive layer. Alternatively, any other coupling members or coupling methods may be used.

Further, according to the ostomy appliance with regard to one example embodiment, the auxiliary storage bag is provided with a first opening and a second opening, the first opening is coupled to the adhesion unit, the second opening is coupled to the faceplate, the storage bag and/or a member installed to the faceplate, the auxiliary storage bag envelops the receiving hole, the storage bag is coupled to the faceplate, the auxiliary storage bag and/or the member installed to the faceplate, and the storage bag envelops the opening of the faceplate.

Further, the ostomy appliance with regard to one example embodiment, further comprises a leakage alarming device that comprises: a sensor having at least more than two electrodes; an analysis circuit that analyzes an electric signal from the sensor so as to detect the excrement; a driver activated by a analysis signal output from the analysis circuit; a transmission unit activated by the driver; a power source that activates the sensor, the analysis circuit, the driver and the transmission unit, wherein the sensor is enclosed in the auxiliary storage bag.

The leakage alarming device alarms that the excrement are captured in the auxiliary storage bag. Thus, the sensor should be arranged in the auxiliary storage bag. As a first aspect of the sensor, it is possible to form a sensor inside the member constituting the auxiliary storage bag and connect the sensor to the analysis circuit outside the auxiliary storage bag. As a second feature, it is possible to put a sensor supported by an insulator into the auxiliary storage bag and connect the sensor to the analysis circuit outside the auxiliary storage bag. As a third feature, it is possible to put the leakage alarming device in a package and arrange the sensor outside the package in an exposed feature. Then, it is used by putting the package in the auxiliary storage bag. It should be notes that the transmission unit may be a vibration member such as a vibration motor; light emission element; piezo-electric speaker; a buzzer; a transmitter emitting radio wave, any of which is activated.

Further, the auxiliary storage bag for the ostomy appliance with regard to one example embodiment, comprises: a faceplate having a faceplate opening that captures excrement from a stoma; and a storage bag that surrounds the faceplate opening and being capable of mounting or detaching, the auxiliary storage bag comprising: an adhesion unit configured to form a receiving hole against a circumference of the faceplate; and an auxiliary storage bag configured to store the excrement leaking between the faceplate and skin of an ostomate, wherein at least an edge of the auxiliary storage bag is coupled to the adhesion unit, and the auxiliary storage bag envelops the receiving hole.

Further, according to the auxiliary storage bag for the ostomy appliance with regard to one example embodiment, the auxiliary storage bag is provided with a first opening and a second opening, and the first opening is coupled to the adhesion unit and the auxiliary storage bag envelops the ostomy appliance, so that an outlet installed in the storage bag is capable of detachable from the second opening.

Further, according to the auxiliary storage bag for the ostomy appliance with regard to one example embodiment, wherein the auxiliary storage bag is provided with a first opening and a second opening, the first opening is coupled to the adhesion unit, the second opening is sandwiched by the faceplate and the storage bag, and the auxiliary storage bag is attached to envelop the receiving hole. The state of being sandwiched by the faceplate and the storage bag is acceptable in any state as long as the second opening is positioned between both. For example, it may be the state that the second opening and/or the absorption body 66 installed in the second opening is sandwiched neighbor the coupling unit 18 of the storage bag inner film or the state of contacting the coupling unit 18.

Further, according to the auxiliary storage bag for the ostomy appliance with regard to one example embodiment, the auxiliary storage bag is provided with a first opening and a second opening, the first opening is coupled to the adhesion unit, a coupling unit is coupled to the second opening, and mounted to or detached from the faceplate, the storage bag and/or the member installed to the faceplate, the auxiliary storage bag is mounted to envelop the receiving hole. This enhances the airtightness of the auxiliary storage bag.

Further, according to the auxiliary storage bag for the ostomy appliance with regard to one example embodiment, the adhesion unit is at least arranged on a lower side of the faceplate, and the adhesion unit is not at least arranged on an upper side of the faceplate. This feature allows the auxiliary storage bag to be fixed to skin by the minimal adhesion unit, reducing the burden on skin.

Further, the auxiliary storage bag for the ostomy appliance with regard to another example embodiment, further comprises a leakage alarming device that comprises: a sensor having at least more than two electrodes; an analysis circuit that analyzes an electric signal from the sensor so as to detect the excrement; a driver activated by a analysis signal output from the analysis circuit; a transmission unit activated by the driver; a power source that activates the sensor, the analysis circuit, the driver and the transmission unit, wherein the sensor is enclosed in the auxiliary storage bag.

Further, according to the ostomy appliance with regard to one example embodiment, comprises: a faceplate having a faceplate opening that captures excrement from a stoma into a storage bag, wherein at least one receiving hole is arranged on the faceplate, so as to store in an auxiliary storage bag the excrement leaking between the faceplate and skin of an ostomate, the auxiliary storage bag is coupled to the faceplate; the storage bag and/or the member installed to the faceplate, so as to envelop the receiving hole, and the storage bag is coupled to the faceplate, the auxiliary storage bag and/or the member installed to the faceplate so as to envelop the faceplate opening. Alternatively, the auxiliary storage bag is coupled to the faceplate and/or the member installed to the faceplate, so as to envelop the receiving hole. Then, a coupling unit is installed to the faceplate, the storage bag and/or the member installed to the faceplate, so as to envelop the receiving hole, and mount or detach the storage bag.

This feature captures the excrement leaking under the faceplate into the auxiliary storage bag. For this purpose, the receiving hole is opened through the faceplate. It should be noted that a plurality of receiving holes may be opened and/or a plurality of auxiliary storage bags may be provided.

Further, according to the ostomy appliance with regard to one example embodiment, a positional fixation member is installed at least partially across the receiving hole, the positional fixation member being weakened in strength, melt down or released by contacting the excrement leaking between the faceplate and the skin of the ostomate.

Further, according to the ostomy appliance with regard to one example embodiment, the auxiliary storage bag is coupled to the faceplate, the storage bag, the member installed to the faceplate and/or the adhesion unit, so as to envelop the receiving hole formed against the adhesion unit arranged on the circumference of the faceplate and/or the receiving hole formed through the faceplate.

The first feature of the receiving hole is formed between the faceplate and the adhesion unit by arranging the adhesion unit along the circumference of the faceplate. This receiving hole is intended to capture the excrement leaking under the faceplate and out of the circumference of the faceplate. The second feature of the receiving hole is opened through the faceplate. This receiving hole is intended to capture the excrement leaking under the faceplate and out of the circumference of the faceplate. The auxiliary storage bag is installed to envelop these receiving holes to envelop the excrement leaked out of the receiving hole. The auxiliary storage bag is coupled to the faceplate, the storage bag and/or the member installed to the faceplate. It should be noted that it is possible to provide each receiving hole with a bridging unit and/or a positional fixation member. In this case, it is possible to form the accurate receiving hole.

Example embodiments may allow the excrement to enter the auxiliary storage bag through an entrance hole when the excrement under the faceplate reaches near its circumference or reaches the circumference of the faceplate to blow-out, preventing the excrement from externally spreading out. At the same time, it is possible to visually confirm the excrement held in the auxiliary storage bag and to easily realize the fact of blowout. Therefore, the ostomate can easily exchange the ostomy appliance.

External spreading of the excrement due to blowout is prevented, and thus contamination of clothing and bedding is avoided. Thus, actions of ostomates and an advance into society are not restricted. Further, various excrement will be solved from hard stool through soft stool, water stool to urine. Mass-production is possible with no special production technology. Since the structure is simple, cheap supply is possible.

An auxiliary storage bag for an ostomy appliance is installed for use in the ostomy appliance the ostomate is accustomed to use. Its components and build-up are shown in FIGS. 1A-E.

The feature of FIG. 1C indicates an outer film 34 of the auxiliary storage bag. The feature of FIG. 1B indicates an inner film 32 of the auxiliary storage bag. These features are made of waterproofing and/or flexible films of synthetic resin as used for existing ostomy appliances. The auxiliary storage bag 31 are formed by coupling methods such as thermal adhesion or solvent adhesion with regard to respective pieces of an upper edge, a left edge, and a right edge of both films, the circumference of belt hook holes 22 and the coupling line 21. At the center of the inner film of the auxiliary storage bag, the first hole 33 is opened. The first hole is coupled to a skin contact 37 to receive the blow-out excrement in the auxiliary storage bag.

At the lower edge of both films, an engagement unit as a fastener 20 is formed. The fastener 20 is the second opening through which the outlet 17 exits from the auxiliary storage bag. The auxiliary storage bag depicted in this embodiment is installed to wrap the entire ostomy appliance. Thus, the outlet provided in the ostomy appliance is enveloped in the auxiliary storage bag. The second opening is a hole intended to draw the outlet to outside.

A plurality of belt hook holes 22 to hook the waist belt are provided on the right and left. The ostomy appliance is often tilt and worn not to be in the way, and thus prevents the ostomy appliance from twisting by being hooked on any one of holes. The coupling line 21 is provided to reinforce the hole 22. The auxiliary storage bag 31 is provided with the outlet filter 23 so that the gas confined in the auxiliary storage bag is exhausted outside.

The feature of FIG. 1A indicates the skin contact 37 installed to form a receiving hole 83 between the skin contact 37 and the circumference of the faceplate 12, working as an adhesion member. For the basic material of the skin contact 37, elastic, waterproofing and/or flexible films or thin films may be used. Alternatively, a nonwoven fabric or fabric which is used for an adhesive plaster may be used. The surface on the side of contacting the skin is provided with an adhesive layer 38 on which an adhesive material is applied or an adhesive sheet is sealed, and is protected by a release paper. The adhesive layer 38 may be a skin protection agent layer that mixes the adhesive material with the skin protection agent. Alternatively, the adhesive layer may be a skin protection agent layer entirely consisting of the skin protection agent. The release paper is provided with a cutting line 40 and/or tab 41 formed by extension of the release paper so that the release paper becomes easier to be released. The auxiliary storage bag for the ostomy appliance will be completed by coupling the first opening 33 with the coupling unit 80 of the first opening 33 on the opposite side of contacting skin. The feature of FIG. 1D depicts a front view of the auxiliary storage bag from the view on the opposite side of contacting skin. The feature of FIG. 1E depicts its cross section view along x-x.

FIGS. 2A-D depict a state in which an auxiliary storage bag for an ostomy appliance is installed to the ostomy appliance. Particularly, the feature of FIG. 2A depicts a front view from the view on the side of non-contacting skin. The feature of FIG. 2B depicts its cross section view along y-y. For the ostomy appliance, the storage bag 16 is configured by the storage inner film 14 and the storage outer film 15. The hole opened by the storage inner film 14 is coupled to the coupling unit 18 of the storage outer film 15 of the faceplate 12.

First, a skin protection agent layer 13 is sealed to abdomen 2 to mount the ostomy appliance. Next, the auxiliary storage bag is installed to envelop the whole of the ostomy appliance while it is necessary to install the auxiliary storage bag having an internal diameter 42 of a skin contact 37 which is larger than an outside diameter of the faceplate. This installation forms a gap between the skin contact 37 and the faceplate. This gap results in a receiving hole 83 to capture the excrement leaking between the faceplate and the skin.

The diameter of the receiving hole requires a large gap diameter when the excrement is a hard stool. If the stool is watery, the receiving hole may be smaller. If the stool is urine, the receiving hole may be slit, the size 0 of the diameter. In practice, the abdomen has a curved surface and thus there is a displacement as the skin contact 37 is distorted. Further, if the diameter is too narrow, an alignment takes a longer time. If the skin contact 37 is sealed to move onto the faceplate, there is a risk that the excrement which slip into the faceplate further slip into the skin contact 37 to spread externally. Thus, it is necessary to install the skin contact 37 that forms a sufficient allowance for the diameter. Of course, installation of the skin contact 37 which is too large increases a physical burden on skin and thus should be avoided. The problem for commercialization can be solved by preparing several sizes.

The outlet 17 and the storage bag 16 are withdrawn from the first opening 33 of the auxiliary storage bag enveloping the ostomy appliance, and stored in the auxiliary storage bag. Then, alignment is conducted so that the receiving hole 83 formed against the faceplate is uniformly formed upward/ downward and leftward/rightward. Then, the release paper is released and the skin contact 37 is sealed. The outlet is stored in the auxiliary storage bag 31 and the fastener 20 is closed. When the waist belt is worn, it is hooked at any one of a plurality of belt hook holes to avoid twisting of the ostomy appliance. As described, working for installing the auxiliary storage bag to the ostomy appliance completes.

The excrement exhausted from the stoma 1 is accumulated as shown in the feature of FIG. 2B. As shown in the feature of FIG. 2C, the fastener 20 is opened and the outlet 17 is withdrawn externally to dispose the excrement. As set forth, after installing the auxiliary storage bag, it is possible to put in and take out the outlet from the second opening and to repeatedly dispose the excrement. Thus, the function of the ostomy appliance will not be lost. The feature of FIG. 2D depicts the state of blowout after the excrement enter between the skin 2 and the skin protection agent layer 13. The receiving hole 83 is formed between the faceplate and the skin contact 37 and the auxiliary storage bag envelops the whole of the ostomy appliance. Thus, the excrement is captured in the auxiliary storage bag and spreadout is prevented.

In case of blowout, the warmth from the stored excrement is felt on the abdomen through the inner film of the auxiliary storage bag. As a result, the fact of the blowout is often found. Even if the blowout is not found this time, it is possible to find the blowout from the storage of the excrement in the auxiliary storage bag during the regular inspection of the ostomy appliance. In other words, the storage of the excrement in the auxiliary storage bag is recognized as signal of blowout occurrence. In other words, the auxiliary storage bag works as a device notifying of limitation of the ostomy appliance. Thus, by early exchange of the ostomy appliances, the time of exposing the skin to the excrement is reduced, preventing the spreadout of the skin disease.

FIGS. 2A-C depicts an example of installing the auxiliary storage bag to one-piece ostomy system having a storage bag for discharging type, while this example is also applicable to two-piece ostomy system. Alternatively, it is possible to install it to the closed-type ostomy appliance with no outlet. Since this closed-type does not discharge the excrement, it is not necessary to provide the second opening. In this case, the fastener 20 provided lower is not necessary and the auxiliary storage bag should be used in which the lower edges of the two pieces of film are thermally adhered, coupled and closed. In any cases, the excrement is stored in the auxiliary storage bag through the receiving hole in case of blowout occurrence, so that spreadout is prevented.

The auxiliary storage bag for the ostomy appliance can be installed without modification of the existing ostomy appliance. It is possible that the auxiliary storage bag is not installed in room while the auxiliary storage bag is installed during going out or taking bath. In case of blowout occurrence, spreadout of the excrement is prevented. The storage of the excrement in the auxiliary storage bag is recognized as signal of blowout occurrence. Further, the auxiliary storage bag shaped as a bag is installed so that the whole of the ostomy appliance is enveloped, and thus the effect of deodorization is also expected. Regardless of the state of the excrement, the structure is simple and easy to produce, and it is possible to commercialize cheaply.

In the embodiment 1, the fastener 20 as a second opening is provided at the lower edge of the auxiliary storage bag. However, the state of the fastener is hard to confirm and it is possible to forget to close the fastener and to use it while it is not completely closed due to lack of the finger power. In case of blowout in this state, the excrement flows out through the fastener. To improve this, the fastener is provided on the side of the auxiliary storage bag. The outer film 34 of the auxiliary storage bag depicted in the feature of FIG. 3B of FIG. 3 is divided longitudinally so that the upper film is located at the lower edge and the lower film is located at the upper edge to shape an engagement unit of the fastener 20.

The feature of FIG. 3A depicts the inner film 32 of the auxiliary storage bag and the first opening 33 is opened. On the skin contact side which is circumference, an adhesion layer 50 is provided by the application of an adhesion agent to shape the ring of the doughnut or sealing the adhesion sheet. The adhesion layer 50 is covered with the release paper 51 and thus protected. The adhesion layer forms the adhesion unit to fix the first opening at the abdomen and to form the receiving hole against the faceplate. To install the auxiliary storage bag to the ostomy appliance, the adhesion unit is attached to the circumference of the faceplate of the ostomy appliance. At this time, the gap formed between the outer circumference of the faceplate and the inner circumference of the adhesion layer becomes the receiving hole intended to capture the excrement into the auxiliary storage bag.

As another feature, it is possible to change the size of the first opening 33, so as to install one auxiliary storage bag to the faceplate of various sizes. In other words, the first opening is formed to fit the smallest faceplate at the beginning, and then is cut by scissor when attached to the larger faceplate. To increase workability and accuracy, a guideline for cutting 29 is drawn on either of: the inner film 32 of the auxiliary storage bag; the adhesion layer 50; or the release paper 51.

If the ostomy appliance for installment is restricted, it is preferable to draw a plurality of guidelines for cutting 29 and display them together with types and sizes. On the other hand, it is preferable to draw a plurality of guidelines for cutting 29 and display the size of the diameter with regard to many and unspecified ostomy appliances.

By coupling the circumference 36 of the inner film 32 of the auxiliary storage bag with that of the outer film 34 of the auxiliary storage bag, the auxiliary storage bag is formed. The feature of FIG. 3C depicts its front view and the feature of FIG. 3D depicts its longitudinal cross section view at the center. In this embodiment, since the adhesion layer 50 as the adhesion unit is provided on the skin contact side of the inner film 32 of the auxiliary storage bag, the number of components becomes fewer and its structure is simple.

The feature of FIG. 4A of FIGS. 4A-D depicts the longitudinal cross-section view in the state that the auxiliary storage bag is installed to the ostomy appliance. The outlet 17 is stored in the auxiliary storage bag 31 and the fastener 20 is closed. Since the fastener 20 is on the side and within the view, confirmation is easier and it is easier to prevent forgetting to close the fastener and failure of engagement.

Figure 4B:
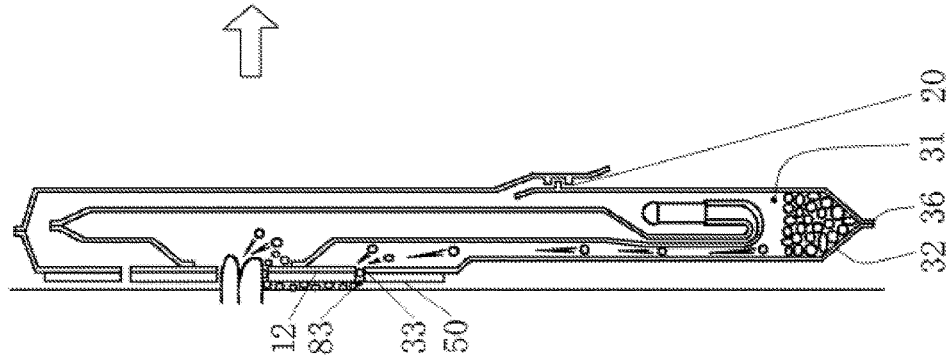
FIG. 4B shows another view of functioning of attachment to existing ostomy appliance according to the second example embodiment.
Figure 4C:
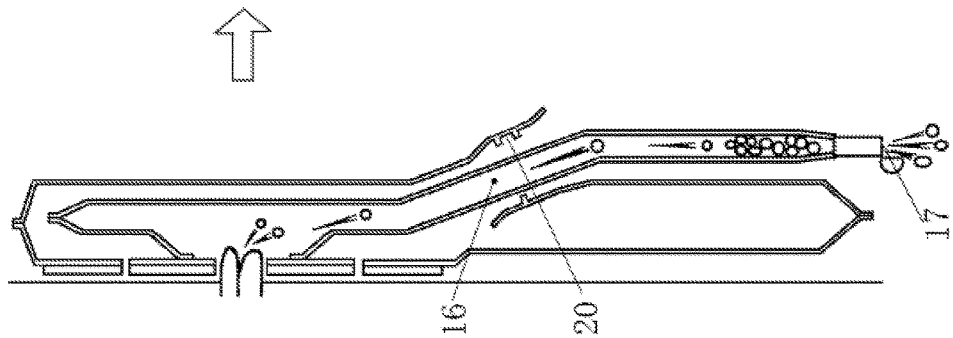
FIG. 4C shows another view of functioning of attachment to existing ostomy appliance according to the second example embodiment.

The feature of FIG. 4B depicts the state that the fastener is opened and the outlet is taken out externally. After the waste is disposed, it becomes reusable again by returning the outlet and closing the fastener. The feature of FIG. 4C depicts the state of blowout in a usual using state. The excrement of blowout will not leak out of the auxiliary storage bag which is airtight.

Figure 4D:
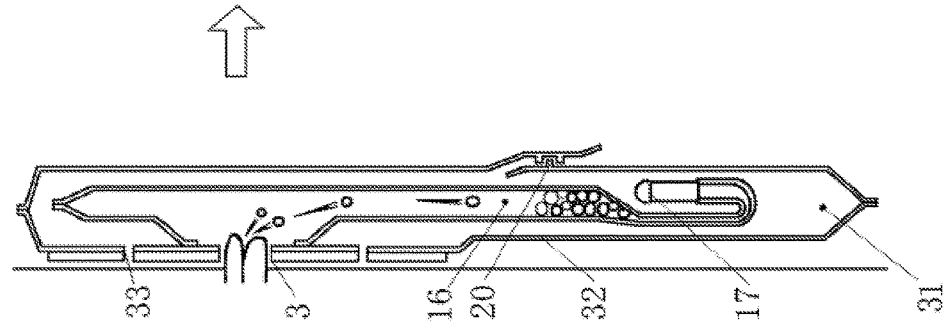
FIG. 4D shows another view of functioning of attachment to existing ostomy appliance according to the second example embodiment.

The feature of FIG. 4D depicts the state that the fastener is failed to close and the blowout happens. Since the fastener is on the side, the risk of the stored excrement flowing out is extremely low. The external leakage is difficult to expect as it happens during prone or handstand posture. As described, if the fastener is failed to close and the blowout happens, the external spreadout is prevented.

The feature of FIG. 5A of FIGS. 5A-C describes development of an inner film 32 of the auxiliary storage bag from a view of the skin contact. The first opening 33 is a small hole in accordance with the smallest faceplate among the ostomy appliances. A guideline for cutting 29 is drawn on either of: the inner film 32 of the auxiliary storage bag; the adhesion layer 50; or the release paper 51. On the guideline for cutting 29, a plurality of circles and squares are drawn, while the corresponding size is shown. Thus, it is possible to easily and accurately cut in accordance with shape of the faceplate of the ostomy appliance. The feature of FIG. 5B depicts the state that the faceplate 12 of a diamond shape is cut along a circular guideline for cutting. The feature of FIG. 5C depicts the state that the faceplate 12 of a square shape is cut along a square guideline for cutting. The first opening 33 is precisely cut and the receiving hole of the ideal shape is formed.

As set forth, the auxiliary storage bag of one kind is capable of being installed to faceplates of various shapes. Further, since the optimal receiving hole is formed, the external spreadout of the excrement is prevented. If the fastener is failed to close and the blowout happens, the risk of the external spreadout is reduced. Thus, even the aged people can use it at ease. The auxiliary storage bag can be installed to both one-piece ostomy system and two-piece ostomy system. The structure is simple, the commercialization is easy and the product can be cheaply supplied.

FIGS. 6A-E shows the third example of components of an auxiliary storage bag for an ostomy appliance and those build-up. The outer film 34 of the auxiliary storage bag is depicted in the feature of FIG. 6C and the second opening 35 is formed at its center. The second opening is characteristically provided in the position facing the faceplate. Further, the second opening is opened to be equal to or less than the outer diameter of the coupling unit 18 of the ostomy appliance for installment. When the auxiliary storage bag is installed to the ostomy appliance, the base of the knob for hooking the belt is in the way. Thus, the back clearance 44 for the knob for hooking the belt is provided on the second opening 35. The feature of FIG. 6B depicts the inner film 32 of the auxiliary storage bag and the first opening 33 is opened. The circumference of the inner film of the auxiliary storage bag is coupled with that of the outer film of the auxiliary storage bag, so as to form the auxiliary storage bag 31.

The feature of FIG. 6A depicts the skin contact 37 and works as the adhesion unit that fixes the first opening 33 to the abdomen and is installed to form the receiving hole against the faceplate. The base member of the skin contact is the flexible thin film and the adhesion unit 38 is provided on the side of contacting the skin. Further, the skin contact is protected by the release paper 39. The release paper is provided with a separation unit 40 and a tab 41. The ostomy appliance is provided with the skin contact having a diameter which is larger than the faceplate, so that the receiving hole 83 is formed between the faceplate and the skin contact.

Figure 7A:
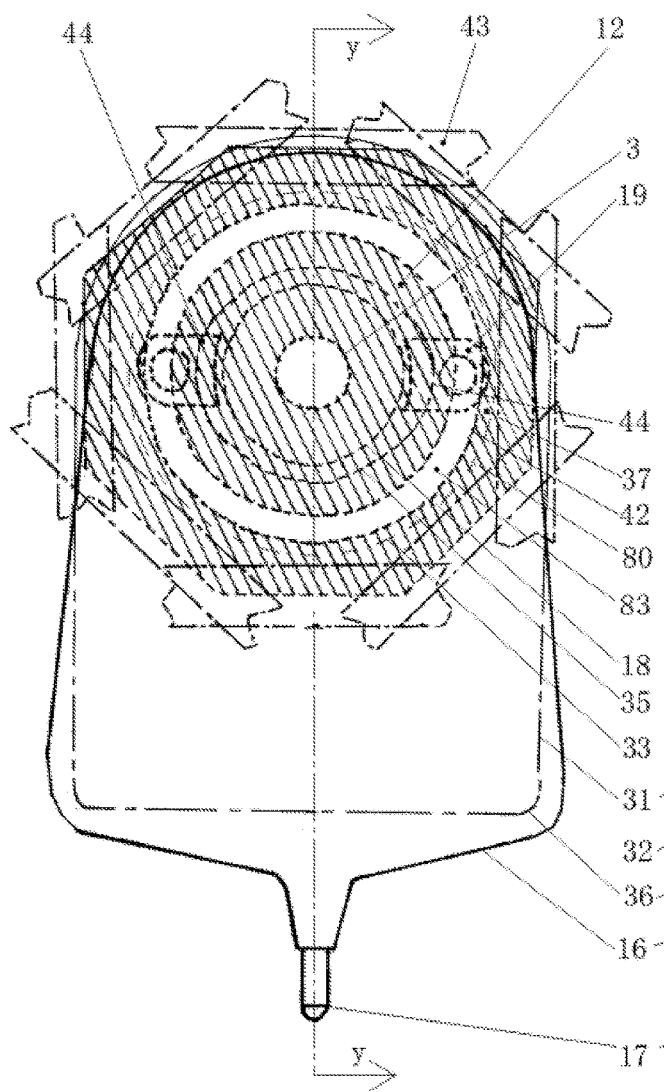
FIG. 7A shows a view of a wearing state of an auxiliary storage bag for an ostomy appliance attached to the ostomy appliance according to the third example embodiment.
Figure 7B:
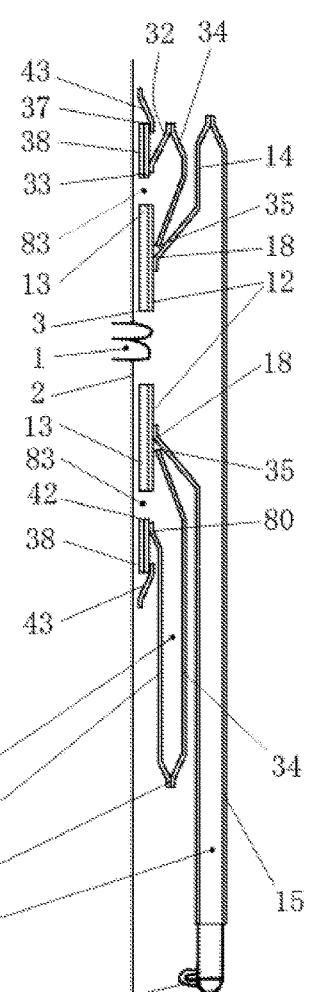
FIG. 7B shows another view of a wearing state of an auxiliary storage bag for an ostomy appliance attached to the ostomy appliance according to the third example embodiment.

The first opening is coupled with the coupling unit 80 on the non-contact side of the skin contact, so as to form the auxiliary storage bag for an ostomy appliance. The feature of FIG. 6D depicts a front view of the auxiliary storage bag. The feature of FIG. 6E depicts its cross section view along x-x. The state of installing the auxiliary storage bag for an ostomy appliance is depicted in FIG. 7. The feature of FIG. 6A depicts a front view from the side of non-contacting skin. The feature of FIG. 6B depicts the longitudinal cross section view along y-y. It is installed to the one-piece ostomy system while it may be similarly installed to the two-piece ostomy system or the ostomy appliance having the storage bag of closed type.

The auxiliary storage bag covers the ostomy appliance attached to the abdomen 2 from its top, and the outlet 17 and the storage bag 16 are withdrawn from the second opening 35 to outside. The second opening, equal to or a little smaller than the outer diameter of the coupling unit 18, is installed so that the second opening is sandwiched by the faceplate and the storage bag, so as to be closely contact the coupling unit 18. Thus, the excrement stored in the auxiliary storage bag does not leak out of the second opening to outside.

It should be noted that it is necessary to withdraw the knob for hooking the belt to the non-contact side of the outer film 34 of the auxiliary storage bag when installing to the ostomy appliance having the knob 19 for hooking the belt. In view of this, the back clearance of the knob for hooking the belt is provided in the second opening 35, allowing the smooth pulling out.

Since the second opening 35 is sandwiched between the faceplate and the storage bag, the positional relation between the ostomy appliance and the auxiliary storage bag is fixed and the skin contact is arranged at the circumference of the faceplate. Since the skin contact having an inner diameter larger than the outer diameter of the faceplate is installed, the receiving hole 83 is formed between both. By confirming that the receiving hole is formed equally to both upward/downward and leftward/rightward, the release paper is released and attached to the abdomen.

The characteristic of this embodiment is that the second opening is opened at the position facing the opposing side of contacting skin of the faceplate. This structure allows the outlet and the storage bag to be withdrawn outside and allows the second opening to be sandwiched between the faceplate and the storage bag. Since the outlet is always exposed after installment, it is advantageously easier to be maintained.

It is possible that the adhesion layer 38 provided on the skin contact 37 is dissolved during bathing or released due to sweating. Thus, the circumference of the skin contact is formed to allow an arbitrary reinforcing tape 43, water resistant or hard to irritate, to be sealed. Since the shape of the circumference of the skin contact is polygonal, it is possible to easily and efficiently seal the reinforcing tape 43. Since the ostomate provides a safety measure by oneself, the more comfortable feeling of safety will be obtained. If the waist belt is used, the waist belt is hooked on the knob 19 for hooking the belt during usage. As described, a series of works of installing the auxiliary storage bag for an ostomy appliance to the ostomy appliance as attachment is completed.

As described, the second opening formed in the auxiliary storage bag is sandwiched between the faceplate and the storage bag. Further, the first opening is fixed to the abdomen by the skin contact. Therefore, the auxiliary storage bag is formed as a shape of a bag and installed to envelop the receiving hole. This structure allows the excrement of blowout to enter the auxiliary storage bag through the receiving hole, preventing the stored excrement from externally spreading out.

The material of the thin film used for the inner film of the auxiliary storage bag and the outer film of the auxiliary storage bag is preferably water-resistant, deodorizing and flexible, as used for the existing ostomy appliance. Alternatively, a material for a thin film with a higher ratio of expansion, e.g. natural rubber, is used for the outer film of the auxiliary storage bag, and the second opening smaller than the outer diameter of the coupling unit 18, so as to enhance adhesion between the second opening and the coupling unit 18. This method is also recommended.

The auxiliary storage bag can be installed to both one-piece ostomy system and two-piece ostomy system. To the two-piece ostomy system, the second opening can be arranged at the circumference of the smallest outer diameter, e.g., the site on installing the coupling unit; or the base site of the supporter 46 where the coupling unit stands out from the faceplate. Thus, attachment is possible by narrowing the second opening between the faceplate and the storage bag.

The auxiliary storage bag for an ostomy appliance may be provided with a sufficient capacity of the storage even if the excrement of blowout is the watery stool or urine, sufficiently preventing spreadout to outside. Further, when the auxiliary storage bag for an ostomy appliance stores the excrement, it is possible to know the occurrence of blowout and to exchange the ostomy appliance in an early stage, preventing the skin disorder from diffusing. It may be installed to the existing ostomy appliance with no modification. The structure is simple and the product can be cheaply supplied.

The fourth example of the auxiliary storage bag for an ostomy appliance is depicted in FIGS. 8A-E. The outer film 34 of the auxiliary storage bag is depicted in the feature of FIG. 8B and the second opening 35 is formed at its center. The second opening is opened to be larger than the outer diameter of the coupling unit 18 of the ostomy appliance for installment, and smaller than the outer diameter of the faceplate 12.

Then, the adhesion agent layer is provided by applying the adhesion material is or sealing the adhesion sheet together in a ring shape, across all circumferences on the side of the skin contact of the second opening. Its surface is protected by several pieces of release paper divided by the separation unit 40. This adhesion agent layer works as the coupling unit intended to enhance airtightness of the auxiliary storage bag. The coupling unit is coupled to at least either the faceplate, the storage bag or the member installed to the faceplate.

The feature of FIG. 8A depicts the inner film 32 of the auxiliary storage bag and the first opening 33 is opened. The first opening is provided with a hole larger than the outer diameter of the faceplate of the ostomy appliance for installment. On the skin contact side which is circumference of the first opening, an adhesion layer 50 is provided by sealing the adhesion sheet or the application of an adhesion agent in the ring shape. The adhesion layer 50 is covered with the release paper 51 and thus protected. The adhesion layer 50 forms the adhesion unit to fix the first opening on the skin and to form the receiving hole against the faceplate. The adhesion unit is used by releasing the release paper using the separation unit 40 or the tab 41.

When the shape of the storage is twisted during attachment of the auxiliary storage bag to the abdomen, the shape of the receiving hole is not correctly formed. To improve this, an adhesion avoiding twist unit 53 is provided on the inner film 32 of the auxiliary storage bag and the outer film 34 of the auxiliary storage bag, for partially coupling both films. The films on the circumference 36 and the adhesion avoiding twist unit 53 are coupled to complete the auxiliary storage bag 31. The feature of FIG. 8C depicts a front view from the view on the opposite side of contacting skin. The feature of FIG. 8C depicts its cross section view along x-x. The feature of FIG. 8E depicts the state of installation to the one-piece ostomy system.

For installment, the auxiliary storage bag is integrated into the ostomy appliance at first, and then is sealed on the abdomen. The outlet 17 and the storage bag 16 are withdrawn from the second opening 35, which is sandwiched between the faceplate and the inner film 32 of the auxiliary storage bag. The first opening is opened to be larger than the outer diameter of the faceplate 12. The receiving hole 83 is formed between the adhesion layer 50 and the faceplate. Then, alignment is conducted so that the receiving hole 83 is uniformly formed upward/downward and leftward/rightward.

On the other hand, a small hole is opened, which is larger than the outer diameter of the coupling unit 18 and smaller than the outer diameter of the faceplate. The side of the skin contact is provided with the adhesion agent layer as the coupler 60. Since the adhesion agent layer is arranged opposing to the side of non-contacting skin of the faceplate, the release paper divided into several sheets are released and the adhesion agent layer is attached on the faceplate. As set forth, the auxiliary storage bag is integrated into the ostomy appliance.

Next, the faceplate is attached by facing the faceplate opening 3 to the stoma 1. After confirming that the receiving holes are equally formed, the adhesion layer 50 is attached on the abdomen. The auxiliary storage bag can be accurately attached as its shape is maintained by the adhesion avoiding twist unit 53.

As set forth, the airtightness is high due to the coupler 60 provided at the circumference of the second opening while coupling with the faceplate is conducted. Then, since the first opening is coupled with the skin contact, the auxiliary storage bag in the airtight state is capable of enveloping the receiving hole. Thus, even if the stored excrement is watery stool or urine, it is possible to avoid distillation and leakage completely. In this embodiment, installment to one-piece ostomy system is set forth, while it is possible to similarly install to the two-piece ostomy system.

It is possible that the coupler 60 is provided on the opposing side to the skin contact of the outer film of the auxiliary storage bag and is coupled with the skin contact side of the inner film of the auxiliary storage bag. Alternatively, it is possible that the coupler 60 is provided on both sides of the second opening or an edge of the second opening to closely contact with the coupling unit 18. Further, the coupler may be detached through engagement members, plane fasteners or suckers aside from adhesion methods using the adhesive agent layer. In this case, the one detaching member is provided on the faceplate, the storage bag or the member installed to the faceplate while the other one detaching member is provided on either site on the skin contact side or non-skin contact side of the second opening.

In this case, it is possible to install and/or remove the auxiliary storage bag. In any cases, the airtightness of the auxiliary storage bag is obtained and it is possible to prevent spreadout. Since the shape of the auxiliary storage bag is maintained by the adhesion avoiding twist unit, even aged people can easily and precisely install it. The auxiliary storage bag consists of only two film members and can be cheaply commercialized.

The fifth example of the auxiliary storage bag for an ostomy appliance is depicted in FIGS. 9A-E. The downward or horizontal orientations of the blowout are by far more than other orientations. The cases of the upward orientation are extremely few. This may be because the excrement flows downward in a daily posture and/or it wrinkles in a horizontal orientation on the abdomen. On the other hand, many ostomates suffer from irritation by tapes and thus hope sealing the adhesive tape on an area as small as possible and using the tape going together to the skin of the user.

It is irrational to provide the adhesion unit 90 on the upper direction on which the blowout hardly happens and the risk of the tape irritation will increase. Thus, the adhesion unit is provided on the lower direction on which the blowout often happens, and is not provided on the upper direction on which the blowout hardly happens. The adhesion unit 90 is referred to as the member arranged across the receiving hole against the circumference of the faceplate, so as to fix the first opening at the abdomen. Specifically, the adhesion unit 90 is the adhesive layer 50 provided on the side of the skin contact of the inner film 32 of the auxiliary storage bag depicted in the embodiment 4; the skin contact 37 of the embodiment 3; or the adhesive layer 38 provide on the skin contact.

The inner film 32 of the auxiliary storage bag is depicted in the feature of FIG. 9A in FIGS. 9A-E. The adhesive layer is different from FIG. 8A in that the adhesive layer 50 is provided on downward or horizontal orientations while is not provided on an upward orientation. As depicted in the completed auxiliary storage bag shown in the front view of FIG. 9C; the longitudinal cross section view of FIG. 9D; and the longitudinal cross section view of FIG. 9E in the state installed to the ostomy appliance, the adhesive layer and the release paper are not provided on the upper orientation. Since the other description is the same aside from this difference, the repeated description is omitted.

Even if the blowout happens in a lower orientation, horizontal orientations, or possibly the upper orientation, the outer film of the auxiliary storage bag fully envelops the faceplate. Thus, the excrement flows downward of the auxiliary storage bag in a posture in a standing state or a sitting state. The possible situation of spreadout is facedown or handstand state, which is unusual. In other words, it is possible to prevent the blowout in a usual daily life from spread out.

The possibility of the blowout upward and flowing of the excrement upward during sleeping is very rare. However, in case of anxiety, the upper edge, the left edge and the right edge of the outer film of the auxiliary storage bag may be sealed on the skin by the reinforce tape 43. Then, by using the reinforce tape going along with the skin of the user, the risk of the tape irritation can be reduced to the lowest. It is possible to release the reinforce tape during sleeping or bathing and thus the condition of the skin can be maintained.

As set forth, the excrement of blowout is surely stored in the auxiliary storage bag by providing the adhesion unit at least on the lower orientation while the adhesion unit is not provided on the upper orientation on which the external spreadout is not expected at all. As a result, the adhesion unit having the minimum area allows the auxiliary storage bag to be installed. The risk of the tape irritation is extremely reduced. Further, it is possible to seal the reinforce tape during sleeping or bathing. It should be noted that this structure is similarly applicable to the ostomy appliance having the auxiliary storage bag set forth in the embodiment 8 and following embodiments. Thus, it is possible to provide the kind and friendly auxiliary storage bag for the ostomy appliance to the ostomates who suffer from the tape irritation.

The sixth example of the auxiliary storage bag for an ostomy appliance is depicted in FIGS. 10A-F. The outer film 34 of the auxiliary storage bag is depicted in the feature of FIG. 10C. In this embodiment, the base material is the thin film as water-resistant and flexible as used in the outer side of the disposable diaper and pad for absorbing urine. Further, the absorption body 66 as a thin sheet is sealed on the middle plane of the auxiliary storage bag. The absorption body is formed in the state of a sheet by mixing the cotton fiber with the macromolecular absorption body used for the disposable diaper and pad for absorbing urine. Thus, the surface of the sheet is covered with the non-woven fabric which is coarse enough for water to pass through. In the middle, the second opening 35 is opened.

The inner film 32 of the auxiliary storage bag is depicted in the feature of FIG. 10B. The lower edge, the left edge and the right edge are coupled with the corresponding portions of the outer film of the auxiliary storage bag, forming the auxiliary storage bag. The portion of the upper edge is the first opening 33 coupled with the skin contact 37.

The feature of FIG. 10A depicts the skin contact 37 as the adhesion unit where the adhesion layer 38 is provided on the side of contacting the skin and the skin contact is protected by the release paper 39. The entire body shapes U-letter. The coupler 80 of the first opening is coupled with one portion on the left edge and one portion on the right edge of the outer film 32 of the auxiliary storage bag. The auxiliary storage bag after installment is shown in the front view of FIG. 10D; the longitudinal cross section view along x-x of FIG. 10E; and the longitudinal cross section view of FIG. 10F in the state installed to the existing ostomy appliance.

The auxiliary storage bag is installed over the ostomy appliance attached to the abdomen. The outlet 17 and the storage bag 16 are withdrawn from the second opening 35, and sandwiched between the faceplate and the inner film 32 of the auxiliary storage bag. The skin contact 37 is arranged in a U-shape across a lower orientation and a horizontal orientation of the faceplate 12. The receiving hole 83 is formed against the faceplate. This is visually confirmed, the release paper 39 is released and the skin contact is sealed on the abdomen.

Regardless of the orientation of the blowout, the excrement flows downward of the auxiliary storage bag in a posture in a standing state or a sitting state. Although the possibility is very rare, the anxiety is possible about the blowout upward and flowing of the excrement upward during sleeping. In this case, the upper edge of the outer film of the auxiliary storage bag may be sealed by the reinforce tape 43.

Further, if the stored excrement is watery stool or urine, the water is absorbed into the absorption body 66 and loses its liquidity. Thus, the risk of polluting the surrounding due to careless handling during disposing the auxiliary storage bag is reduced. Thus, it is possible to provide the kind and friendly auxiliary storage bag in a low price for the ostomy appliance to the ostomates who suffer from the tape irritation.

The seventh example of the auxiliary storage bag for an ostomy appliance is depicted in FIGS. 11A-D and 12A-C. The feature of FIG. 11B in FIGS. 11A-D depicts a film composing the auxiliary storage bag which is folded along the folding line 24 to the side of the skin contact and coupled with the coupling line 21 of the left and right edges, forming the auxiliary storage bag.

The lower edge of the film is the first opening 33. The second opening 35 is formed on the upper portion of the film. The absorption body 66 is installed to surround the circumference. The absorption body 66 is manufactured by thin compression of cotton fiber with a high water absorption ratio and cutting in the form of doughnuts-type disc. It is possible to mix the granule of the macromolecular absorption body. The absorption body may be installed to the skin contact side, the side opposing to the skin contact, or both.

Regardless of the outer diameter of the coupling unit 18 of the ostomy appliance, the size of the second opening can be easily and precisely manufactured to be covered by one auxiliary storage bag. A small hole is opened through the second opening 35 before usage to correspond to the coupling unit 18 having the smallest outer diameter. Then, a guideline for cutting 52 is displayed on either of: the surface on the skin contact side; the surface on the side opposed to the skin contact; or the film surface of the second opening. If the installed ostomy appliance is restricted, the guideline for cutting adapted to each product number is drawn and displayed together. Alternatively, if installed to many and unspecified ostomy appliances, a plurality of guidelines for cutting are drawn, each of which is a circle having the same center, and the size is displayed together.

The sealing portion 47 is provided on the upper edge, the left edge and the right edge of the film. The surface processing is applied on this sealing portion for the reinforce tape 43. The mark for sealing the reinforce tape 43 may be displayed. The feature of FIG. 11A indicates the skin contact 37 working as the adhesion unit on the lower orientation of the faceplate. The base member of the skin contact is the flexible thin film and the adhesion unit 38 is provided on the side of contacting the skin. Further, the skin contact is protected by the release paper 39. The coupler 80 of the first opening is provided on the side opposed to the skin contact and is coupled with the first opening 33.

The feature of FIG. 11C depicts a front view of the installed auxiliary storage bag from the view on the opposite side of contacting skin. The feature of FIG. 11D depicts its longitudinal cross section view along x-x. The absorption pad 67 is stored in the auxiliary storage bag. The absorption pad 67 is manufactured by: enveloping the granule of the macromolecular absorption body through cotton fiber and/or wood pulp; forming in the rectangle shape of the thin pad; and enveloping using the coarse non-woven fabric.

FIGS. 12A-C depicts the auxiliary storage bag installed to the existing ostomy appliance. The feature of FIG. 12B depicts a front view. The feature of FIG. 12C depicts its cross horizontal section view along y-y. The feature of FIG. 12A depicts its longitudinal cross section view along z-z. The auxiliary storage bag for the ostomy appliance is installed after the ostomy appliance is attached on the ostomy appliance. On the guideline for cutting, the product number of the ostomy appliance or the size of the hole is drawn. By selecting the guideline for cutting, the film and the absorption body 66 is cut by a scissor. When installing to the ostomy appliance having the knob for hooking the belt 19, it is preferable to modify the cutout for releasing the knob for hooking the belt 19 by using the scissor.

Next, the outlet 17 and the storage bag 16 are withdrawn from the second opening 35, which is fixed by being sandwiched between the faceplate and the storage bag. By confirming that the receiving hole 83 is formed on the lower orientation of the faceplate, the release paper is released. The skin contact is arranged only on the lower orientation and the auxiliary storage bag is installed through the minimum adhesion layer 38. It is the kind structure for ostomates who suffer from the tape irritation.

Regardless of the orientation of the blowout, the excrement flows downward of the auxiliary storage bag in a posture in a standing state or a sitting state. During sleeping, it is possible to seal and fix the reinforce tape 43 on the sealing portion 47 as depicted in the feature of FIG. 12B. The reinforce tape going along with the skin of the user may be used and the risk of the tape irritation can be reduced.

On the other hand, the risk remains that the adhesion layer 38 provided on the skin contact 37 arranged lower causes the tape irritation. In this case, the whole auxiliary storage bag tilts rightward or leftward by several tens degrees with regard to the stoma 3. The arrangement is possible that moves the position of attachment and relieve the skin in turn.

The second opening is sandwiched between the faceplate 12 and the inner film of the storage bag in a closely contacting state. However, a leakage is possible of if the excrement is the watery stool or urine. In this embodiment, the absorption body 66 is provided on the circumference of the second opening to absorb the water content of the excrement about to leak out. The absorption body swells to closely contact the film, increasing effects of the preventing the leakage.

On the other hand, the absorption pad 67 is stored in the auxiliary storage bag and absorbs the stored watery stool and urine. Since the liquidity of the excrement is lost, the risk of wasting the surrounding caused by careless handling during disposing the auxiliary storage bag can be reduced.

Further, the absorption pad 67 or the absorption body 66 may include the chemical material that forms color by contacting the water contents or secretions included in the excrement from inside of the body. For example, the method may be mixing the cotton fiber with food pigment like Brilliant Blue FCF, or water-soluble pigment like pigment and dye. Alternatively, the cotton fiber may include the chemical reaction substance that forms color or discolors by chemical reaction of the water content and the secretion of the excrement. Further, it is possible to mix the chemical substance dissolved by the water content in the excrement with the reaction substance that forms color by reacting the chemical substance.

Further, the method is also effective to apply the above chemical substance on the middle-side face of the member constituting the auxiliary storage bag. Alternatively, the method is also effective to put the granular, encapsulated, or jelly-like adhesive chemical substance into the auxiliary storage bag. The excrement which has been stored forms color and can show the clear signal to the aged people with poor eyesight.

The absorption pad 67 or the absorption body 66 may include the component of deodorant or fragrance so that it is expected to weaken or disable the smell from the excrement. Alternatively, the absorption pad 67 may include the exothermic agent that reacts with the water content. Further, the material of the absorption pad that absorbs the water content may be replaced with the exothermic agent. The exothermic agent may be produced by mixing the calcium oxide as the main material with the aluminum powder having a drop of reaction agent. When the excrement is stored in the auxiliary storage bag, the exothermic agent reacts and the heat is emitted. The ostomate feels the heat and immediately recognizes the blowout.

The fact that the excrement is stored in the auxiliary storage bag indicates occurrence of the blowout, and can be visually and easily recognized. Thus, the ostomy appliance is exchanged in an early stage and it is possible to reduce the risk of the skin disorder diffusing. Even in case of blowout, it is possible to prevent the excrement from the external spreadout and to provide the friendly auxiliary storage bag for the ostomy appliance for the ostomate who suffers from the serious tape irritation.

Another embodiment of the auxiliary storage bag for the ostomy appliance will be set forth, which is the ostomy appliance integrating the faceplate, the storage bag and the auxiliary storage bag. Those components are depicted in FIGS. 13A-G. The feature of FIG. 13D depicts the faceplate 12. On its center, the faceplate opening 3 is opened for capturing the excrement from the stoma into the storage bag. The skin contact side is provided with the skin protection agent layer 13 and the release paper. The non-contact side of skin is provided with the coupling unit 18 of the inner film of the storage bag.

The knob 19 for hooking the belt that intends to hook the waist belt should be provided between the coupling unit 18 of the inner film of the storage bag and the coupling unit 79 of the second opening. The knob 19 for hooking the belt may be integrated with the faceplate. Alternatively, as depicted in the feature of FIG. 13G, it is also recommended to install to the faceplate the member integrating the knob 19 with the top of the base 45 of the knob for hooking the belt.

The feature of FIG. 14C of the FIGS. 14A-C depicts the horizontal cross section view that indicates the base of the knob for hooking the belt is installed to the faceplate using the adhesive agent. From the thick base of the knob for hooking the belt in a ring shape, the knob 19 stands out to the directions of three and nine o'clock of a clock. The knob standing out secures the inner space of the auxiliary storage bag so that the excrement smoothly falls down. Further, the non-skin contact side of the base is provided with the coupling unit 79 of the second opening.

The feature of FIG. 13E depicts the inner film 14 of the storage bag and the hole 77 is formed in the middle of the inner film of the storage bag to be coupled with the coupling unit 18 of the inner film of the storage bag provided on the faceplate. The feature of FIG. 13F depicts the outer film 15 of the storage bag coupled with the outer circumference 76 of the inner film of the storage bag to form the storage bag 16, and the outlet 17 is installed at the lower edge. The feature of FIG. 13A depicts the skin contact 37 sealed on the skin to form the receiving hole 83 against the faceplate 12 that works as the adhesive unit. The base material of the skin contact may be made of the flexible this film. The skin contact is provided with the adhesive layer 38 and is protected by the release paper.

On the side of non-skin contact, the coupler 80 of the first opening is provided. At the center of the skin contact, a hole 42 larger than the circumference of the faceplate is opened. When attached to the abdomen, a gap is formed between the faceplate and the skin contact. This gap works as the receiving hole 83 intended to capture the excrement of blowout into the auxiliary storage bag. The size of the receiving hole supposes that the excrement is hard or soft stool. Thus, the size should consider the error caused by installment. Further, if the shape outline of the faceplate is ellipse or polygonal, the shape of the inner circumference 42 of the skin contact should be desirably similar so that the receiving hole has the same size of the gap and surrounds the faceplate.

The feature of FIG. 13B indicates the inner film 32 of the auxiliary storage bag, on the center of which the first opening 33 is opened. The feature of FIG. 13C indicates the outer film 34 of the auxiliary storage bag, on the center of which the second opening 35 is opened. The outer circumferences 36 of both films are coupled to form the auxiliary storage bag. The first opening is coupled with the coupler 80 of the first opening provided on the skin contact. The second opening is coupled with the coupler 79 of the second opening provided on the base of the knob for hooking the belt. Each member is coupled through methods such as thermal adhesion or solvent adhesion. Thus, the ostomy appliance becomes complete that forms the storage bag and the auxiliary storage bag of airtight.

When the ostomy appliance is attached, the auxiliary storage bag may be sandwiched in the underwear or wrinkled and ridden up. To prevent this ridden-up situation, the plane fastener convex 27 is provided on the lower edge of the outer film 34 of the auxiliary storage bag, and the plane fastener concave 28 is provided on the lower edge of the inner film 14 of the auxiliary storage bag. For attachment, they are in contact together and capable of preventing the ridden-up situation of the auxiliary storage bag due to their weight. When necessity like inspection, it is possible to release them.

As another way of preventing the ridden-up situation, the absorption pad 67 is recommended to be stored in the auxiliary storage bag. Due to the existence and the weight of the absorption pad, the ridden-up situation is prevented and the liquidity of the stored excrement is lost. Thus, when the ostomy appliance is disposed, the careless flow out of the excrement is also prevented.

The ostomy appliance attached to the abdomen is depicted in FIGS. 14A-C. The feature of FIG. 14A depicts a front view from the side of non-skin contact. The feature of FIG. 14B depicts its longitudinal cross section view along x-x. The feature of FIG. 14C depicts its cross horizontal section view along y-y. For installment, the release paper of the faceplate is released and sealed on the abdomen. Next, after confirming the receiving hole is equally formed upward/downward and leftward/rightward, the release paper of the skin contact is released and sealed on the abdomen. When using the waist belt, the waist belt is hooked on the knob 19 for hooking belt and the attachment of the ostomy appliance is completed.

Even if the blowout happens during attachment of the waist belt, the excrement flows out through the space secured by the knob standing out, being surely stored in the auxiliary storage bag. Since the outer circumference of the skin contact is polygonal, the easy and efficient sealing is possible during bathing. The skin contact may be reinforced by the reinforce tape, allowing further surer and safer feeling of usage. Since the auxiliary storage bag is integrated in the ostomy appliance, work efficiency and the preciseness of alignment of the attachment are enhanced. Further, the face fastener and the absorption pad prevent the auxiliary storage bag from being ridden up. Further, since the auxiliary storage bag forms the airtight bag to cover the receiving hole, the spreadout is surely prevented regardless of water stool or urine.

The development of the ostomy appliance having the auxiliary storage bag is depicted in FIGS. 15A-G. According to the features of FIGS. 15A-E, the first opening 33 provided in the auxiliary storage bag is coupled with the skin contact where the adhesion layer 38 is formed. According to the feature of FIG. 15F, the circumference of the first opening is provided with the adhesion layer 50. According to the feature of FIG. 15G, the circumference of the outer film 34 of the auxiliary storage bag is coupled with the skin contact. The feature of FIG. 15G depicts the structure that excludes the inner film 32 of the auxiliary storage bag. In this feature, the auxiliary storage bag in the state of the bag is constructed by the non-contact side of the skin contact, the outer film 34 of the auxiliary storage bag, and the non-contact side of the faceplate.

The auxiliary storage bag can be compactly configured and is effective to the hard stool of the small amount or the soft stool. Further, if the highly elastic film material is used for the outer film 34 of the auxiliary storage bag, the problem of the much watery stool or urine may be solved. The adhesive layer 38 or 50 works as the adhesive unit 90, which is arranged to form the receiving hole 83 against the circumference of the faceplate. The first opening is coupled with the adhesive unit.

Next, the second opening 35 is coupled with: the faceplate according to the features of FIG. 15A and of FIG. 15D to of FIG. 15G; the storage bag according to of FIG. 15B; and the inner film 14 of the auxiliary storage bag and the outlet 17 according to of FIG. 15C. FIGS. 14A-C depict an example of the second opening coupled with the base 45 of the knob for hooking the belt, which is the member installed to the faceplate. Further, the outlet is provided in the storage bag installed to the faceplate, and thus is substantially the member installed to the faceplate.

As set forth, the second opening is coupled with at least one of the faceplate; the storage bag and the member installed to the faceplate. Further, the second opening may be coupled across a plurality of members as depicted in the feature of FIG. 14C. As set forth, the storage of airtight having a sufficient storage volume is formed in the auxiliary storage bag, enveloping the receiving hole 83. Thus, the blowout occurs in this storage bag and the external spreadout is also prevented.

On the other hand, the storage bag is coupled with: the base 45 of the knob for hooking the belt installed to the faceplate according to the feature of FIG. 15A; the faceplate according to the features of FIG. 15B, of FIG. 15C, of FIG. 15F and of FIG. 15G; and the auxiliary storage bag according to the features of FIG. 15D and of FIG. 15E. In other words, the storage bag is coupled with at least one of: the faceplate; the auxiliary storage bag; and the member installed to the faceplate. In any example of development, the structure of the storage bag envelops the faceplate opening. Thus, the excrement from the stoma can be stored in the storage bag.

Next, the structure of sharing the film configuring the auxiliary storage bag and a portion of the film configuring the storage bag is depicted. The first structure as depicted in the feature of FIG. 15B is the structure forming the auxiliary storage bag 31 using the film of the storage bag 16 formed on the faceplate. First, the storage bag is installed to the faceplate or the member installed to the faceplate, so as to envelop the faceplate opening 3. Then, the inner film 14 of the auxiliary storage bag is coupled with the second opening 35 to share the film.

According to the feature of FIG. 15C, the second opening is coupled from the inner film 14 of the auxiliary storage bag to the outlet 17, sharing the film. In any cases, the first opening is coupled with the adhesion unit to form the auxiliary storage bag, which envelops the receiving hole. Further, the second opening may be coupled with at least one of the faceplate or the member installed to the faceplate aside from the storage bag.

Second, as depicted in the feature of FIG. 15D, one partial film of the formed auxiliary storage bag is shared to form the storage bag. At beginning, the first opening is coupled with the adhesive unit and the second opening is coupled with the faceplate or the member installed to the faceplate to form the auxiliary storage bag, which envelops the receiving hole. Then, the storage bag is coupled with outer film 34 of the auxiliary storage bag. The film is shared to envelop the faceplate opening. Further, the storage bag may be coupled with at least one of the faceplate or the member installed to the faceplate aside from the storage bag. As set forth, there are several ways of forming the storage bag and the auxiliary storage bag. In any ways, no special technology is required and it is possible to be cheaply commercialized.

Further, the faceplate and the adhesion unit depicted in each example of development may be selected from combinations of: both skin protection agent layers; both adhesive layers; the faceplate and the adhesive unit each having the skin protection agent layer and the adhesive layer with different natures. Further, the recommended structure for avoiding the tape irritation may be that the adhesive unit may be provided in the lower of the faceplate while not provided in the upper.

Due to the integration, the auxiliary storage bag of the complete airtight is constructed so that the spreadout is completely avoided even though the excrement of blowout is watery stool or urine. Thus, working of attachment becomes easier and preciseness of installment will be improved.

Figure 16A:
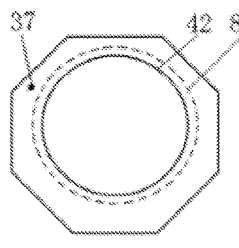
FIG. 16A is shows a view of providing a pocket with an integrated ostomy appliance according to a ninth example embodiment.

The development depicted in the feature of FIG. 15D of FIGS. 15A-G is specifically embodied in FIGS. 16A-J. The feature of FIG. 16A depicts the skin contact 37. The base member of the skin contact is the flexible thin film and the adhesion unit 38 and the release paper are provided on the side of contacting the skin. The coupler 80 of the first opening is provided on the side opposed to the skin contact and works as the adhesion unit. To surely receive the excrement, the lower width is broad enough to enhance the ability of adhesion.

Figure 16B:
FIG. 16B is shows another view of providing a pocket with an integrated ostomy appliance according to the ninth example embodiment.
Figure 16C:
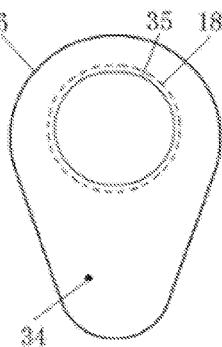
FIG. 16C is shows another view of providing a pocket with an integrated ostomy appliance according to the ninth example embodiment.
Figure 16E:
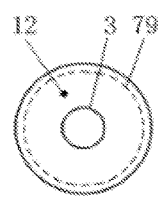
FIG. 16E is shows another view of providing a pocket with an integrated ostomy appliance according to the ninth example embodiment.
Figure 16D:
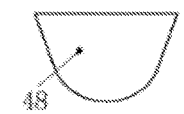
FIG. 16D is shows another view of providing a pocket with an integrated ostomy appliance according to the ninth example embodiment.

The feature of FIG. 16B indicates the inner film 32 of the auxiliary storage bag, on the center of which the first opening 33 is opened, and which is coupled with the coupler 80 of the first opening 33 of the skin contact. The feature of FIG. 16C indicates the outer film 34 of the auxiliary storage bag, on the center of which the second opening 35 is opened. The feature of FIG. 16D indicates the film for pocket 48 wide and deep enough to store the outlet 17 installed to the storage bag through the pocket opening on the top edge.

The three pieces of film, which are the inner film 32 of the auxiliary storage bag, the outer film 34 of the auxiliary storage bag and the film for pocket 48 are coupled along the circumference 36 of the auxiliary storage bag. The pocket is formed on the side of non-contacting skin of the outer film 34 of the auxiliary storage bag. On the surface of the skin contact side of the inner film 32 of the auxiliary storage bag, the non-woven fabric which does not stick to skin may be installed. By using transparent film for the outer film 34 of the auxiliary storage bag and the film for pocket 48, the content of the auxiliary storage bag becomes easier to confirm during inspection.

The feature of FIG. 16F indicates the inner film 14 of the storage bag. The hole 77 opened on the center of the outer film of the auxiliary storage bag is coupled with the coupling unit 18 provided on the outer film 34 of the auxiliary storage bag. The feature of FIG. 16E indicates the faceplate 12, on the center of which the faceplate opening 3 is formed. The skin contact side is provided with the skin protection agent layer 13 and the release paper. The coupler 79 of the second opening provided on the non-contacting skin is coupled with the second opening 35. The outer film 15 of the storage bag indicated by the feature of FIG. 16G is coupled with the outer circumference 76 of the inner film 14 of the storage bag to form the storage bag 16. The outlet 17 is installed in the storage bag. Thus, the ostomy appliance is complete, an integration of the auxiliary storage bag, the storage bag and the faceplate.

For attachment, the faceplate is attached to the abdomen at first. Next, by confirming that the receiving hole is formed equally between the faceplate and the skin contact, the skin contact is attached and the procedure of the attachment is complete. The feature of FIG. 16H depicts a front view of the attached ostomy appliance from the side of non-skin contact. The feature of FIG. 16I depicts its longitudinal cross section view along x-x. The feature of FIG. 16J depicts the longitudinal cross section view of outlet 17 stored in the pocket. The capacity of the auxiliary storage bag may be large enough to store the excrement of blowout. Thus, it is not large enough to be in the way. However, the storage bag and the outlet are large enough to be in the way, and thus the circumference of the outlet becomes easily unsanitary.

The outlet is stored in the pocket as depicted in the feature of FIG. 16J, becoming compact and sanitary. Even though the outlet is open-type and closed by being folded several times, the outlet may be stored in the pocket in the similar structure. By storing the outlet in the pocket, the weight of the outlet prevents the wrinkling.

The member constituting the ostomy appliance is coupled by methods such as the thermal adhesion or adhesion. Thus, even though the excrement is watery stool or urine, the external spreadout will be completely prevented. Since the outlet is compactly stored in the pocket, it does not irritate to the life, is sanitary and prevents wrinkling.

The development depicted in the feature of FIG. 15C of FIGS. 15A-G is specifically embodied in FIGS. 17A-J. The feature of FIG. 17A depicts the skin contact 37. The base member of the skin contact is the flexible thin film and the adhesion unit 38 and the release paper are provided on the side of contacting the skin. The coupler 80 of the first opening is provided on the side opposed to the skin contact. On the center, the ellipse hole 42 similar to the outline of the faceplate 12 is formed. The shape of the hole is large enough to form the receiving hole 83 optimized against the faceplate. On the upper orientation with a low risk of blowout, the width of the skin contact is narrow. The skin contact works as the adhesion unit.

The feature of FIG. 17B indicates the inner film 32 of the auxiliary storage bag, on the center of which the first opening 33 is opened and coupled with the coupler 80 of the first opening 33. In this embodiment, the auxiliary storage bag 31 is characteristically constructed by two sheets, which are the inner film 32 of the auxiliary storage bag and the outer film 14 of the storage bag. In other words, the outer film 14 of the auxiliary storage bag is omitted. The film of the auxiliary storage bag and the storage bag is commonly used. The circumference 36 of the inner film 32 of the auxiliary storage bag works as the second opening 35. The feature of FIG. 17C indicates the protection film 49 for softly feeling the auxiliary storage bag, for which the non-woven fabric is used, and works as the storage bag for the outlet.

The feature of FIG. 17E indicates the inner film 14 of the storage bag which is coupled with the circumference of the inner film 32 of the auxiliary storage bag to form the auxiliary storage bag. Further, the left and right edges are coupled. The feature of FIG. 17D indicates the faceplate 12, on the center of which the faceplate opening is formed. The skin contact side is provided with the skin protection agent layer 13 and the release paper. The coupler 18 of the inner film 14 of the storage bag is provided on the side of non-contacting skin and is coupled with the hole 77 of the inner film 14 of the storage bag. The outer film 15 of the storage bag indicated by the feature of FIG. 17F is coupled with the outer circumference 76 of the inner film 14 of the storage bag to form the storage bag 16.

The lower edges of both films are respectively installed to the folding-up plates 56 to form the outlet 17. Further, by providing the plane fastener convex 27 and the plane fastener concave 28 and folding up the folding-up plates 56 three times, they are configured to be closed through the plane fastener.

The storage bag is provided with the observation window for inspection inside the auxiliary storage bag. If both the inner film 14 and the outer film 15 of the storage bag are transparent film, the whole observation window is thermally adhered as depicted in the feature of FIG. 17H. If the inner film of the storage bag is not transparent, the portion of the observation film of the inner film of the storage bag is hollowed out and the circumference is thermally adhered as depicted in the feature of FIG. 17I. If the outer film of the storage bag is not transparent, the portion of the observation film of the outer film of the storage bag is hollowed out and the circumference is thermally adhered as depicted in the feature of FIG. 17J. Due to these methods, the inside of the observation film is constructed by the transparent film so that the state inside the auxiliary storage bag can be inspected from outside.

The feature of FIG. 17G depicts a front view of the ostomy appliance attached to the abdomen from the side of non-skin contact. The feature of FIG. 17H depicts its longitudinal cross section view along x-x. The capacity of the auxiliary storage bag may be large enough to store the excrement of blowout since the auxiliary storage bag forms the body of the bag. A portion of the storage bag is shared. Thus, the auxiliary storage bag will not be wrinkled and in the way. The feature of FIG. 17I depicts the state of folding up the folding-up plates three times and closing the outlet. The feature of FIG. 17J depicts the state of storing the outlet in the protection film 49.

Since the outlet is stored in the protection film, the outlet becomes invisible from outside and sanitary. A piece of film is shared between the auxiliary storage bag and the storage bag to be compact. Thus, it is not necessary to cautiously use the auxiliary storage bag. The volume of the components can be reduced and wrinkling of the auxiliary storage bag can be prevented. The auxiliary storage bag is completely closed and the capacity of the auxiliary storage bag is large. Thus, even though the stool is watery or urine, spreadout is effectively prevented. Further, since there is the observation window, the inside of the auxiliary storage bag can be easily observed. Confirmation of the excrement from the observation window is recognized as the signal of blowout occurrence. Then, the device allows the ostomate to know that the ostomy appliance exceeds the limitation of usage. Early exchange of the ostomy appliances prevents the skin disorder from diffusing.

Another embodiment of the ostomy appliance will be depicted in FIGS. 18A-E, which integrates the faceplate, the storage bag and the auxiliary storage bag to discharge the excrement flowing into the auxiliary storage bag. In case of blowout during travelling, it is possible that the ostomy appliance cannot be replaced for a while. If this situation remains untouched, the limitation of the volume capacity will be reached, which is serious. Thus, this embodiment intends to solve this.

According to the feature of FIG. 18A, the tip of the auxiliary storage bag is coupled with the hole formed through inner film of the storage bag. This hole is an elongated slit, or may be circular, ellipse or a plurality of holes according to the nature of the excrement. According to the feature of FIG. 18B, a backwater valve 84 formed by opposing two pieces of film together is provided in the auxiliary storage bag 31. According to the feature of FIG. 18C, the tip of the auxiliary storage bag is deeply inserted into the storage bag and works as the backwater valve.

According to the feature of FIG. 18D, a piece of film is shared between the auxiliary storage bag and at least one or more holes are formed to penetrate both. According to the feature of FIG. 18E, a backwater valve 84 is provided in the auxiliary storage bag 31.

As set forth in the above embodiment, the outlet is installed in at least one of: the film constituting the auxiliary storage bag; and the film constituting the storage bag. The auxiliary storage bag communicates with the storage bag through at least one or more holes or slits. This allows the excrement flowing into the auxiliary storage bag and the excrement flowing into the storage bag to be stored in one place and be discharged from one outlet. Since the auxiliary storage bag is arranged to direct from top to lower and the top of the auxiliary storage bag has no exit, the stored excrement will not flow backward to the receiving hole 83. Further, according to the features of FIG. 18B, of FIG. 18C and of FIG. 18E, the backwater valve is provided and increases certainty.

Due to the above structure, the excrement flowing from the stoma is stored in the bag and the disposal from the outlet 17 can be repeated. In case of blowout, the excrement of the blowout is also stored in the same bag. Even though the time and/or place for replacing the ostomy appliances is not reserved, the typical method of discharging from the outlet 17 allows the easy disposal in a short time. The volume capacity of the bag is large enough to have adequate time until the bag becomes full. When time allows, it is possible to exchange the ostomy appliances. Thus, the actions of the ostomate will not be restricted. Since the auxiliary storage bag communicates with the storage bag, wrinkling will be prevented.

According to FIGS. 19A-B, the feature of FIG. 19A depicts a front view of the ostomy appliance attached to the abdomen from the side of non-skin contact and the feature of FIG. 19B depicts its longitudinal cross section view along x-x.

On the center of the faceplate, the faceplate opening 3 is formed. To envelop the faceplate opening, the coupling unit 18 for the inner film of the storage bag, and the coupling unit 79 for the second opening on the outer side are provided. On the outer side, there is the outer circumference of the square faceplate. On the outer side of the faceplate, the skin contact 37 is arranged to be separated from the receiving hole 83. The shape of the skin contact is similar to the outer circumference of the faceplate. The non-skin contact side is provided with the coupler 80 of the first opening. The skin contact is the adhesion unit. Between the faceplate and the skin contact, the bridging unit 85 partially coupling both is provided.

The non-skin contact side of the faceplate, the skin contact and the bridging unit maintains its shape by formed synthetic resin. The faceplate has the skin protection agent layer 13 and the skin contact has the adhesion layer 38. The bridging unit is provided with the skin protection agent layer extending from the faceplate or the adhesive layer extending from the skin contact, forming the different layers partitioned by the partition line 25. The skin protection agent layer and the adhesive layer are protected by one sheet of the release paper cut in the same shape. The adhesive layer may be the skin protection agent layer having a different nature by mixing the adhesive agent with the skin protection agent.

The coupler 79 of the second opening and the coupler 80 of the first opening are respectively coupled with corresponding film to form the auxiliary storage bag, which envelops the receiving hole 83. On the other hand, the coupling unit 18 of the inner film of the storage bag is coupled with the inner film of the storage bag 14 to form the storage bag 16. On the lower portion, the outlet 17 is provided. The attachment method of this ostomy appliance is very easy in that the necessary thing is releasing and sealing one sheet of the release paper on the stoma 1. If the release paper is divided into several sheets, efficiency and the preciseness of sealing will be enhanced.

In this embodiment, since the faceplate is coupled with the skin contact on three bridging units 85, the positional relation will not displace and the irritation due to the alignment of the skin contact will be overcome. The excrement of blowout passes through the receiving hole 83 in the form of slit between the bridging units, so as to be stored in the auxiliary storage bag. Then, it is preferable to reduce the bridging units on the lower and to concentrate the bridging units on the upper not to prevent the excrement to pass through. Further, the area between the faceplate and the faceplate opening may be broader in the upper area than in the lower area so that the excrement entering in the lower orientation is easily protected by the skin agent protection agent layer.

In case of blowout during travelling, it is possible that the ostomy appliance cannot be replaced for a while. If this situation remains untouched, the limitation of the volume capacity will be reached, which is serious. Thus, the outlet 86 for the auxiliary storage bag is provided to dispose the excrement as the emergency measures. Since it is not necessary to use the outlet 86 again and again, the body is preferably easy and not bulky. In this embodiment, the fastener and the perforation for cutting the top edge out is provided on the lower of the auxiliary storage bag. The outlet with the top edge closed is also provided. Of course, the outlet as used for the existing storage bag may be used.

The top edge is cut into strips along the perforation and the fastener is opened so as to dispose the excrement. After disposal, the fastener is closed to form an easy outlet for any possible usage. Thus, the ostomate feels safe in that the replacement of the ostomy appliance may be postponed.

FIGS. 20A-F and 21A-D depict the development of the faceplate, the adhesion unit and the bridging unit, depicting the front view and the longitudinal cross section view from the non-skin contact side. The longitudinal cross section view partially depicts the coupled film. Description of the release paper for protection of skin contact surface is omitted.

Three development examples depicted in FIG. 20A-F describes usage of the skin protection agent layer 13 continuously across the faceplate 12, the skin contact 37 and the bridging unit 85. As depicted in the feature of FIG. 20A, the receiving hole 83 in a crescent shape is formed neighbor to the circumference of the faceplate. The skin contact 37 forms the outside of the receiving hole 83 and the faceplate 12 forms the inside of the receiving hole 83. The upper portion works as the bridging unit 85 that couples the skin contact with the faceplate. The number of the bridging unit is limited to one. However, since the bridging unit is wide, the positional relation between the faceplate and skin contact is maintained so that the shape of the receiving hole does not deform.

As depicted in the feature of FIG. 20B, a plurality of circular receiving holes are formed near the circumference of the faceplate. As depicted in the feature of FIG. 20C, a plurality of receiving holes in slit shapes are formed. In any case, the bridging unit is formed between the receiving holes so that the outer side is the skin contact and the inner side is the faceplate. The coupling unit in each film on the non-skin contact side is coupled with each film. Then, the formed auxiliary storage bag envelops the receiving hole, allowing the auxiliary storage bag to capture the excrement entering under the faceplate.

While the skin protection agent layer is provided on both the faceplate and the skin contact in these cases, the adhesive layer may be provided on both. Alternatively, the partitioned line may be provided in the bridging unit to provide the skin protection agent layer and the adhesive layer each having different nature.

The faceplate 12 depicted in the feature of FIG. 21A of FIGS. 21A-D forms an ellipse shape. The ellipse skin contact 37 is formed so that the receiving hole 83 is formed in the same width. The skin protection agent layer 13 is provided on the skin contact side of the faceplate. The base member of the skin contact is the flexible thin film and the adhesion unit 38 is provided on the side of contacting the skin. The bridging unit 85 extend from the inner circumference of the skin contact to the orientation of the inner side. The tip of the bridging unit is coupled with the faceplate through the tape border 26. Since the blowout often occurs in the lower orientation of the faceplate, the bridging unit is not provided in the lower orientation of the faceplate. Since three portions of the bridging unit fixes the positional relation of the faceplate and the skin contact, the alignment is not necessary.

The faceplate depicted in the feature of FIG. 21B is configured by the inner faceplate 93 and the outer faceplate tape 94. The inner faceplate is configured by a substrate for the formed faceplate and the skin protection agent layer 13. The outer faceplate tape 94 is a ring shaped concentric tape by using the thin film material as a base material and providing the adhesive layer 38 on the skin contact surface. The outer circumference of the inner faceplate is coupled with the inner circumference of the outer faceplate tape. This structure of the faceplate allows the adhesive layer of the outer faceplate tape to enhance the adhesive power of the inner faceplate.

The skin contact 37 is provided so that the receiving hole 83 is formed against the outer circumference of the faceplate. The skin contact is formed by the same material as the outer faceplate tape and shapes concentric rings. The outer circumference of the outer faceplate tape is partially coupled with the inner circumference of the skin contact through a plurality of bridging units 85. The formed receiving hole is a slit in an arch, a cut with a gap size of 0.

According to the practical manufacturing, the integration of the outer faceplate tape and the skin contact is cut out from the base material in the sheet shape. Namely, concentric rings with the inner size of the outer faceplate tape and the outer size of the skin contact are cut out. Then, the portion forming the receiving hole is cut into a slit by a scalpel. The inner circumference of the cutout component is coupled with the outer circumference of the inner faceplate. The non-skin contact side of the inner faceplate is provided with the coupling units 18 and 79 while the non-skin contact side of the skin contact is provided with the coupler 80, so that each film is coupled together. The surface of the skin contact side is protected by the release paper.

When attaching the ostomy appliance, the positional relation between the faceplate and the skin contact, or the positional relation between the faceplate and the adhesion unit, is maintained through the bridging unit. Thus, displacement is avoided and working is easy. The faceplate 12 of this ostomy appliance formed by the inner faceplate 93 and the outer faceplate tape 94. The excrement entering under the inner faceplate breaks through the outer circumference of the outer faceplate tape and the blowout occurs.

When the excrement reaches the receiving hole 83, the outer faceplate tape wrinkles and the receiving hole appears against the skin contact. As the blowout proceeds, the excrement is pushed out of the receiving hole. Even though the excrement reaches the bridging unit which is fixed to the skin, the excrement is stored in the auxiliary storage bag through the receiving hole. Even though the excrement is hard, soft or watery stool or urine, the receiving hole will flexibly expand according to the state of the stool and the excrement will be smoothly stored in the auxiliary storage bag.

As set forth, since the faceplate is partially coupled with the adhesion unit through at least one bridging unit, the displacement between the faceplate and the skin contact will be avoided. The structure is applicable to both the one-piece ostomy system and two-piece ostomy system. Attaching the ostomy appliance becomes free from the irritation due to the alignment of the skin contact so that even the aged people can easily and precisely attach the ostomy appliance. Regardless of the excrement of blowout, spreadout is prevented so that the ostomate enjoys the safe social life.

The example of the release paper will be set forth used for the ostomy appliance with the auxiliary storage bag. FIGS. 22A-D depict the front view of the faceplate 12 and the adhesion unit 90 from the side of the skin contact. When attaching the ostomy appliance on the abdomen, the positional relation between the faceplate and the adhesion unit displaces. Thus, there is the irritation of adjusting the formation of the proper receiving hole for visual confirmation, which will be solved by the release paper.

The feature depicts the faceplate 12, the adhesion unit 90 and the receiving hole 83. The skin contact side is provided with the release paper covering across the faceplate opening 3 and the circumference of the adhesion unit. The release paper is divided by the division unit 40 into three pieces, each of which is sealed across the faceplate and the adhesion unit. Namely, the hole as large as the faceplate opening 3 is formed on the central release paper which is sealed across the faceplate and the adhesion unit. The left side and right side of the release paper are also sealed across the faceplate and the adhesion unit. The tab 41 may be provided on the release paper so that the release paper is easily released. The feature of FIG. 22B depicts separation into four pieces by the division unit 40. The feature of FIG. 22C depicts separation into two pieces. Each piece of the release paper is sealed across the faceplate and the adhesion unit.

Figure 22D:
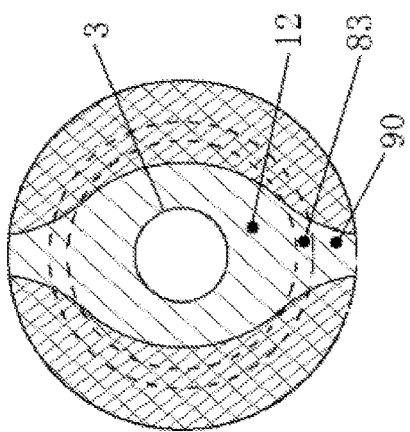
FIG. 22D is another view of a development example of sticker paper attached to an adhesion unit and a faceplate according to the twelfth example embodiment.
Figure 22C:
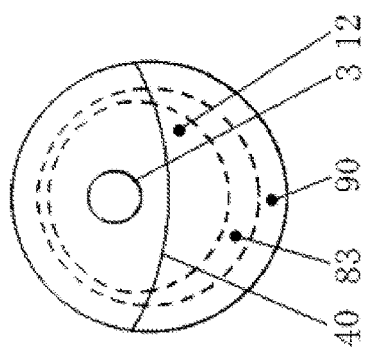
FIG. 22C is another view of a development example of sticker paper attached to an adhesion unit and a faceplate according to the twelfth example embodiment.
Figure 22B:
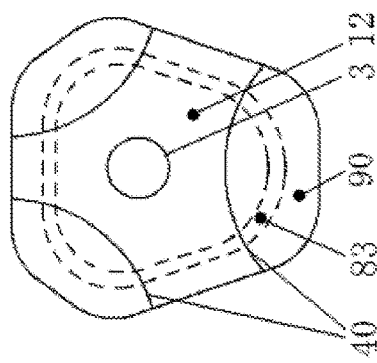
FIG. 22B is another view of a development example of sticker paper attached to an adhesion unit and a faceplate according to the twelfth example embodiment.
Figure 22A:
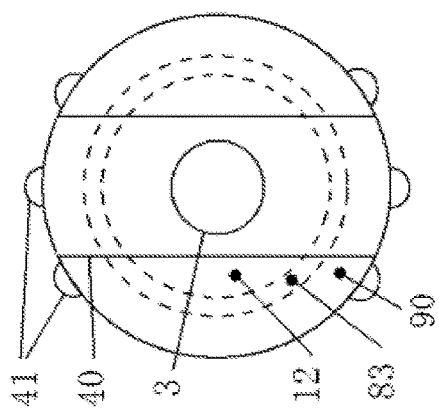
FIG. 22A is a view of a development example of sticker paper attached to an adhesion unit and a faceplate according to a twelfth example embodiment.

The feature of FIG. 22D diagonally depicts the release paper in a crescent shape on the right and the left sides, each of which is sealed across the faceplate and the adhesion unit. The third sheet of the release paper covers across the faceplate opening and the circumference of the adhesion unit and is sealed on a portion of the adhesion unit and the circumference of the faceplate opening. The portion overlapped with the first and second sheets of the release paper is in the air.

First, the release paper sealed on the surrounding of the faceplate opening 3 is released to attach the ostomy appliance on the abdomen. In this state, the remainder of the release paper maintains the positional relationship between the faceplate and the adhesion unit. After attachment to the abdomen, the portion sealed on the abdomen maintains the positional relationship between both. Finally, by the sequentially releasing and attaching the remainder of the release paper, the positional relationship between both will not be displaced, allowing the easy and precise attachment.

As set forth, at least two sheets among the plurality of the divided sheets of the release paper, are arranged across the faceplate and the adhesion unit. Thus, the positional relationship between the faceplate and the adhesion unit will not be displaced for attachment. Thus, the receiving hole 83 is formed as designed so as to surely store the excrement of blowout in the auxiliary storage bag. The irritation due to the alignment of the skin contact during attachment of the ostomy appliance will be overcome, allowing even the aged people to easily and precisely attach the ostomy appliance. The structure of the release paper is applicable to both the one-piece ostomy system and two-piece ostomy system.

FIGS. 23A-D depict the example of the ostomy appliance characterized in a plurality of auxiliary storage bags: the front view of the faceplate from the skin contact side and the longitudinal cross section view in a different scale.

Figure 23B:
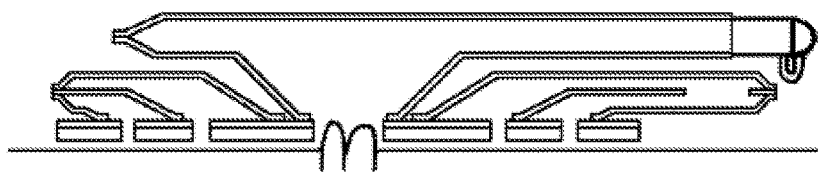
FIG. 23B is another view of a development example of an ostomy appliance having a plurality of auxiliary storage bags according to the thirteenth example embodiment.
Figure 23A:
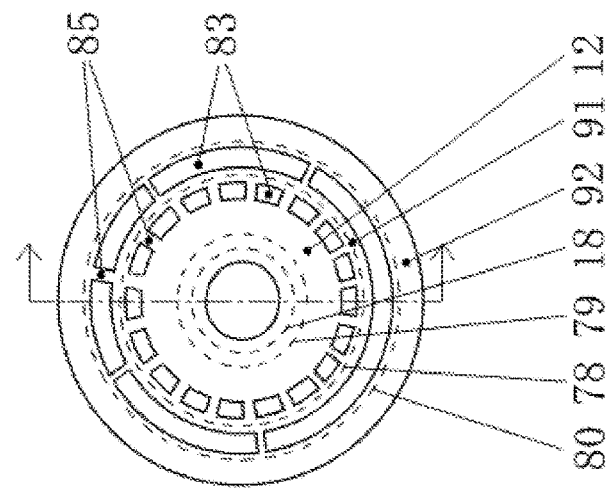
FIG. 23A is a view of a development example of an ostomy appliance having a plurality of auxiliary storage bags according to a thirteenth example embodiment.
Figure 23D:
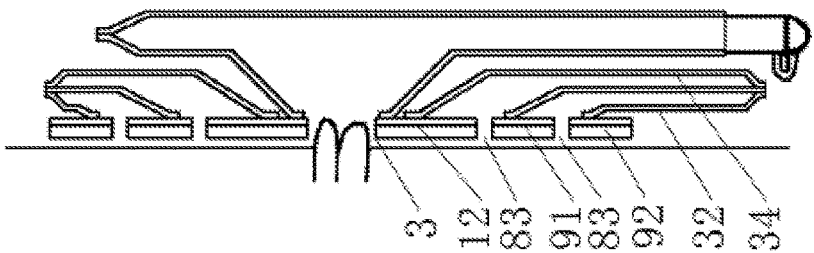
FIG. 23D is another view of a development example of an ostomy appliance having a plurality of auxiliary storage bags according to the thirteenth example embodiment.
Figure 23C:
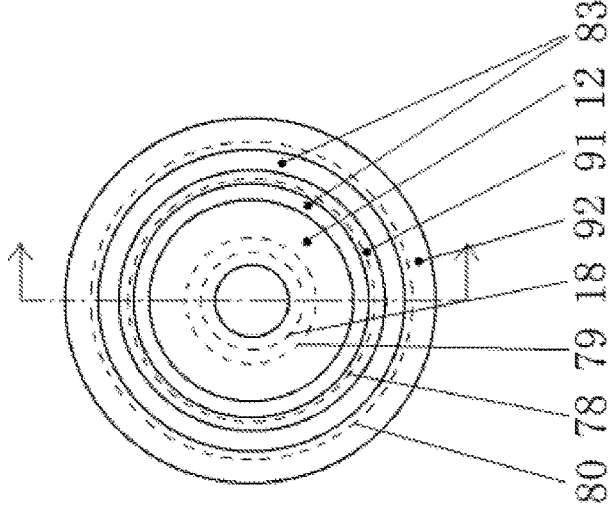
FIG. 23C is another view of a development example of an ostomy appliance having a plurality of auxiliary storage bags according to the thirteenth example embodiment.

According to the feature of FIG. 23A, the first skin contact 91 arranged surrounding the circumference of the faceplate 12 and the second skin contact 92 arranged surrounding the first skin contact 91. The receiving hole 83 is formed between them. The coupling unit 18 of the inner film of the storage bag and the coupler 79 of the second opening is provided. The coupler 78 of the intermediate film for the auxiliary storage bag is provided on the non-skin contact side of the first skin contact. The coupler 80 of the first opening is provided on the non-skin contact side of the second skin contact. The intermediate film for the auxiliary storage bag is provided between the inner film 32 for the auxiliary storage bag and the outer film 34 for the auxiliary storage bag. Each outer circumference is coupled together and each inner circumference is coupled with each coupling unit, forming the first auxiliary storage bag and the second auxiliary storage bag.

According to this ostomy appliance, the excrement of blowout is stored in the first auxiliary storage bag. In some reasons, the excrement of blowout may pass through between the first skin contact and the skin and then the excrement will be stored in the second auxiliary storage bag. In other words, the double safety measure is applied.

As depicted in the feature of FIG. 23B, a plurality of bridging units 85 partially couple between the faceplate, the first skin contact and the second skin contact. Urine or the watery stool is mainly captured through the relatively small receiving hole 83 formed between the faceplate and the first skin contact. Hard or soft stool is mainly captured through the relatively large receiving hole formed between the first skin contact and the second skin contact.

On the other hand, the first auxiliary storage bag communicates with the second auxiliary storage bag by shortening the lower edge length of the intermediate film of the auxiliary storage bag or by forming the hole on the lower. Urine or the watery stool is mainly captured in the first auxiliary storage bag. Hard or soft stool is mainly captured in the second auxiliary storage bag. Even though the volume of each stool is unevenly accumulated, each communication increases the volume of the capacity and prevents the capacity from becoming full. The bridging unit partially couples between the faceplate, the first skin contact and the second skin contact. Since the positional relationship each other does not displace, the work of attachment become easy and precise.

The faceplate, the first skin contact and the second skin contact may be entirely of the skin protection agent layer or of the adhesive layer. Alternatively, the skin protection agent layer and the adhesive layer may be mixed, each having different nature. The structure is applicable to both the one-piece ostomy system and two-piece ostomy system. Since the plurality of the auxiliary storage bags are multi-layered, the safety will be enhanced.

FIGS. 24A-F depict the example of the two-piece ostomy system installing the auxiliary storage bag. The two-piece ostomy system is attached/detached by providing the coupling member on the side of the faceplate and the side of the storage bag. The coupling may be methods of: engagement of the concave engagement member and the convex engagement member; sealing the storage bag having the adhesive layer on the flexible circular flange; and coupling through screws. Any methods and/or members may be acceptable for the coupling.

The convex engagement member is used for the coupling member 81 on the faceplate side according to the features of FIG. 24A to FIG. 24D while the concave engagement member is used for the coupling member 82 on the storage bag side. According to the feature of FIG. 24A, the first opening 33 is coupled with the skin contact 37 and the second opening 35 is coupled with the faceplate 12 so as to form the auxiliary storage bag 31 which envelops the receiving hole 83. The coupling member 81 on the faceplate is installed on the faceplate to be engaged with the coupling member 82 of the storage bag side.

The upper half of the feature of FIG. 24B depicts the half of the horizontal cross section view where the faceplate opening 3 is its center. The lower half of the feature of FIG. 24B depicts the lower side of the longitudinal cross section view. The base 45 of the knob for hooking the belt is installed on the faceplate to surround the faceplate opening. The knob 19 for hooking the belt stands out to the directions of three and nine o'clock of a clock. This shape secures the inner space of the auxiliary storage bag 31. The first opening 33 is coupled with the skin contact and the second opening 35 is coupled with the base 45 of the knob for hooking the belt so as to form the auxiliary storage bag 31 which envelops the receiving hole 83. The coupling member 81 is coupled with the base 45 of the knob for hooking the belt.

According to the features of FIG. 24A and of FIG. 24B, it is necessary to put the coupling member 82 of the storage bag side, on the coupling member 81 for engagement. Thus, the burden disadvantageously appears neighbor to the stoma. For improvement, the supporter 46 for the coupling member is provided consisting of the synthetic resin standing out from the faceplate to the outside of the non-skin contact side. On the tip, the coupling unit 81 and the second opening 35 are installed. Thus, by inserting the finger under the support 46 and putting another finger on the auxiliary storage bag 31 for sandwiching, the burden nearby the stoma is reduced and the engagement surely becomes possible.

According to the feature of FIG. 24D, the first opening 33 is coupled with the skin contact 37 and the second opening 35 is coupled with the faceplate 12 so as to form the auxiliary storage bag 31 which envelops the receiving hole 83. The coupling member 81 is installed to the outer film 34 for the auxiliary storage bag. In this case, it is easy to insert the finger under the coupling member, allowing the sure engagement.

The coupling member 81 used in the feature of FIG. 24E is a circular flexible flange standing out from the neighbor of the faceplate opening. Its surface is in the shape of the plate allowing the adhesive agent to be easily sealed. On the other hand, the coupling member 82 of the storage bag side shapes a flexible circular disc and is provided with the adhesive layer. The first opening 33 is coupled with the skin contact 37 and the second opening 35 is coupled with the faceplate 12 so as to form the auxiliary storage bag 31 which envelops the receiving hole 83.

According to the feature of FIG. 24F, the coupling member 81 shapes a flexible circular disc. The concentric film coupled to surround the faceplate opening is the supporter 46 for the coupling member which is installed to the outer circumference of the supporter 46. The elasticity of the film allows the coupling member to move and float against the faceplate.

According to the feature of FIG. 24D, the first opening 33 is coupled with the skin contact 37 and the second opening 35 is coupled with the faceplate 12 so as to form the auxiliary storage bag 31 which envelops the receiving hole 83. In this case, it is easy to insert the finger under the coupling member, enhancing the certainty and workability. According to the development examples of FIG. 24A to of FIG. 24F, the skin contact 37 having the adhesive layer 38 is used. Alternatively, the structure of the adhesive layer 50 provided in the inner film 32 for the auxiliary storage bag may be used as the adhesive unit.

As set forth above, when installing the auxiliary storage bag 31 on the faceplate of the two-piece ostomy system, the adhesive unit is arranged to form the receiving hole against the outer circumference of the faceplate and the first opening is coupled with the adhesive unit. The second opening is coupled with: the faceplate as depicted in the features of FIG. 24A, of FIG. 24D and of FIG. 24E; the base 45 of the knob for hooking the belt as depicted in the feature of FIG. 24B; or the supporter 46 for the coupling member as depicted in the features of FIG. 24C and of FIG. 24F. Alternatively, the second opening may be coupled with another member installed to the faceplate.

Of course, the second opening may be coupled across the above plurality of sites. In other words, the second opening is coupled with at least any one site among the faceplate and the member installed to the faceplate. Since the first coupling unit is coupled with the second coupling unit to form the auxiliary storage bag which envelops the receiving hole 83.

Next, the coupling member is coupled with: the faceplate as depicted in the features of FIG. 24A and of FIG. 24E; the base 45 of the knob for hooking the belt as depicted in the feature of FIG. 24B; or the supporter 46 for the coupling member as depicted in the features of FIG. 24C and of FIG. 24F. Alternatively, the second opening may be coupled with the auxiliary storage bag as depicted in the feature of FIG. 24D or another member installed to the faceplate. Of course, the coupling member may be coupled across the above plurality of sites. In other words, the coupling member is coupled with at least any one site among the faceplate, the auxiliary storage bag and the member installed to the faceplate.

As set forth above, by providing the auxiliary storage bag to the faceplate of the two-piece ostomy system, it is possible to prevent the excrement from the external spreadout even in case of blowout, allowing the ostomate to have a safe social life. Only by adding the simple member to the faceplate, easy commercialization is possible without a large modification on the traditional structure.

FIGS. 25A-D depict the example of the ostomy appliance integrating the faceplate, the storage bag and the auxiliary storage bag. In this embodiment, the auxiliary storage bag stores the excrement enters between the faceplate and the skin. In other words, this embodiment mainly focuses on the excrement entering between the faceplate and the skin, instead of the excrement leaked out from the outer circumference of the faceplate.

Figures 25A, 25B, 25C, 25D:
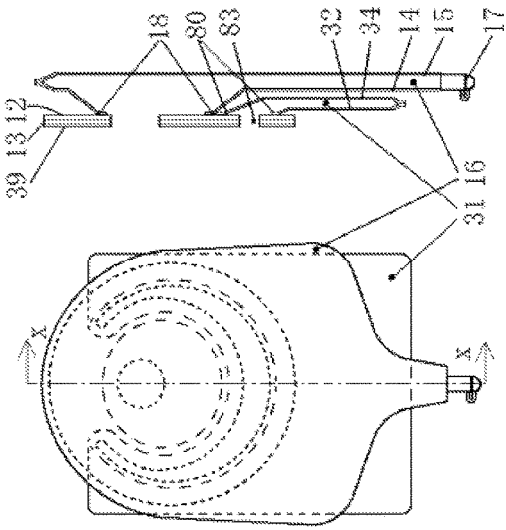
FIG. 25A shows a view of an ostomy appliance having an entry hole through the faceplate according to a fourteenth example embodiment.
FIG. 25B shows another view of an ostomy appliance having an entry hole through the faceplate according to the fourteenth example embodiment.
FIG. 25C shows another view of an ostomy appliance having an entry hole through the faceplate according to the fourteenth example embodiment.
FIG. 25D shows another view of an ostomy appliance having an entry hole through the faceplate according to the fourteenth example embodiment.

On the faceplate 12 depicted in the feature of FIG. 25A, the faceplate opening 3 and the capture hole 83 are formed. This receiving hole is intended to capture the excrement that entered from the faceplate opening to the orientation of the outer circumference of the faceplate, into the auxiliary storage bag. Thus, the receiving hole is not provided on the upper orientation with a low risk of blowout. The faceplate is provided with the skin protection agent layer 13 and is protected by the release paper 39.

The feature of FIG. 25B indicates an outer film 34 of the auxiliary storage bag. The feature of FIG. 25C indicates an inner film 32 of the auxiliary storage bag. The lower, left and right edges of the film and the outer circumference 36 on the upper straight portion of both films are coupled to form the auxiliary storage bag. The outer circumference 33 forming the curves of both films is the first opening, which is coupled along the curve of the coupler 80 of the first opening provided on the faceplate.

Figures 25F, 25G:
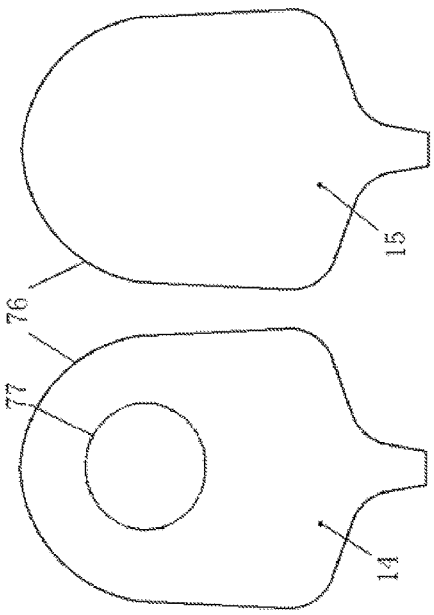
FIG. 25F shows another view of an ostomy appliance having an entry hole through the faceplate according to the fourteenth example embodiment.
FIG. 25G shows another view of an ostomy appliance having an entry hole through the faceplate according to the fourteenth example embodiment.
Figure 25E:
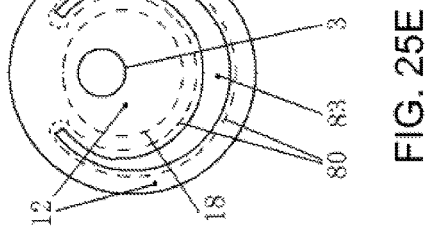
FIG. 25E shows another view of an ostomy appliance having an entry hole through the faceplate according to the fourteenth example embodiment.

The outer film 15 of the storage bag is indicated by the feature of FIG. 25G and the inner film 14 of the storage bag is indicated by the feature of FIG. 25F. The outer circumferences 76 of both films are coupled to form the storage bag. On the lower edge, the outlet 17 is provided. The hole 77 opened on the inner film 14 of the storage bag is coupled with the coupling unit and installed. The front view from the non-skin contact side is indicated by the feature of FIG. 25C. The longitudinal cross section view along x-x is indicated by the feature of FIG. 25D.

The second characteristic of this embodiment is that the faceplate opening 3 is not included inside the loop of the coupler 80 of the first opening. This means that the storage bag is not included in the auxiliary storage bag. Thus, this structure does not require the second opening that exposes the outlet provided in the storage bag from auxiliary storage bag.

Figure 26E:
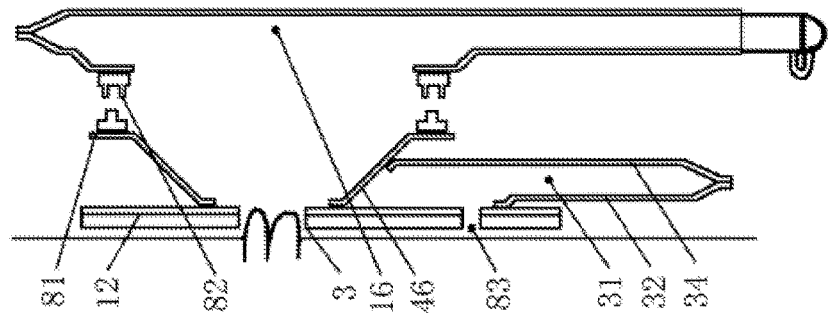
FIG. 26E is another view of an ostomy appliance having an entry hole through the faceplate according to the fourteen example embodiment.
Figure 26D:
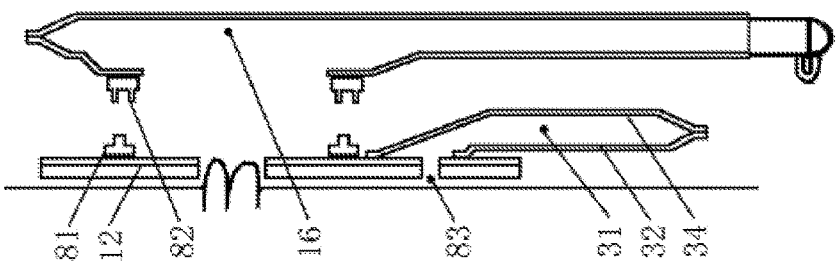
FIG. 26D is another view of an ostomy appliance having an entry hole through the faceplate according to the fourteen example embodiment.
Figure 26C:
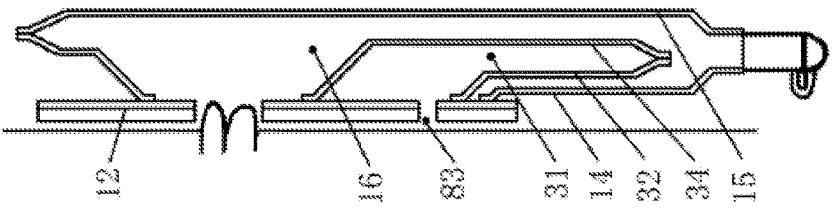
FIG. 26C is another view of an ostomy appliance having an entry hole through the faceplate according to the fourteen example embodiment.
Figure 26B:
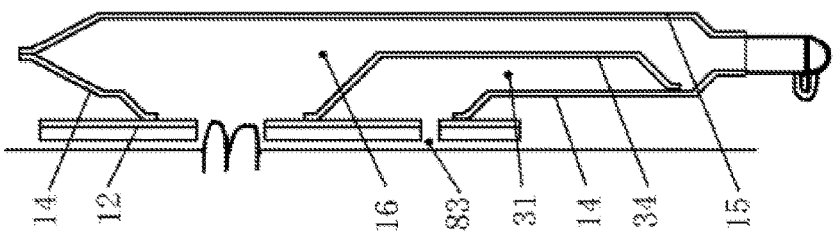
FIG. 26B is another view of an ostomy appliance having an entry hole through the faceplate according to the fourteen example embodiment.
Figure 26A:
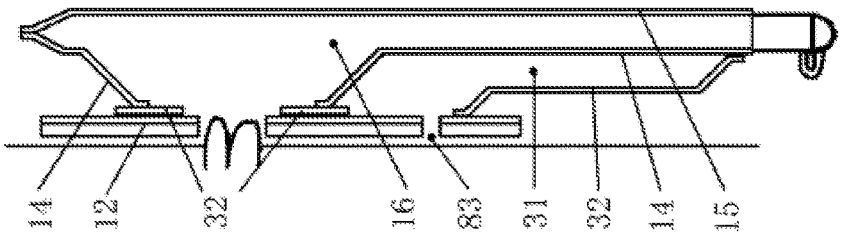
FIG. 26A is a view of an ostomy appliance having an entry hole through the faceplate according to the fourteen example embodiment.

FIGS. 26A-E depict the development of this structure. As depicted in the feature of FIG. 26A, the auxiliary storage bag consists of the inner film 32 of the auxiliary storage bag and inner film 14 of the storage bag. The storage bag 16 consists of the outer film 15 of the storage bag and the inner film 14 of the storage bag. The hole of the same size is opened through the portion where the receiving hole 83 overlaps the faceplate opening 3 on the inner film 32 of the auxiliary storage bag. The faceplate is coupled with the inner film 32 of the auxiliary storage bag through the circumference of the receiving hole and the circumference of the faceplate opening. Next, the inner film 14 of the storage bag is coupled with the circumference of the receiving hole and the outer circumference of the inner film 32 of the auxiliary storage bag, forming the auxiliary storage bag. Finally, the outer circumference of the inner film 14 of the storage bag is coupled with the outer circumference of the outer film 15 of the storage bag, forming the storage bag.

According to the feature of FIG. 26B, the inner film 14 of the storage bag is coupled with the faceplate 12. Next, the outer circumference of the outer film 34 of the auxiliary storage bag is coupled with the faceplate and the inner film 14 of the storage bag, so as to envelop the receiving hole to form the auxiliary storage bag. Finally, the outer circumference of the inner film 14 of the storage bag is coupled with the outer circumference of the outer film 15 of the storage bag, forming the storage bag. As depicted in the feature of FIG. 26C, the auxiliary storage bag 31 is formed to envelop the receiving hole. Then, the inner film 14 of the storage bag and the outer film 15 of the storage bag forms the storage bag 16. The faceplate may be provided with members such as the knob for hooking the belt and/or the base. If each film is coupled with the faceplate, coupling with the member installed to these faceplates is possible.

The features of FIG. 26A to of FIG. 26C depicts methods of forming the storage bag and the auxiliary storage bag on the one-piece ostomy system having the faceplate opening and the receiving hole. In other words, the auxiliary storage bag is coupled with at least one of the faceplate, the storage bag and the member installed to the faceplate, and formed to envelop the receiving hole. The storage bag is coupled with at least one of the faceplate, the auxiliary storage bag and the member installed to the faceplate, and formed to envelop the receiving hole. The storage bag is formed to envelop the faceplate opening.

Next, the method of forming the storage bag and the auxiliary storage bag to the two-piece ostomy system having the faceplate opening and the receiving hole. As depicted in the feature of FIG. 26D, the inner film 32 of the auxiliary storage bag is coupled with the outer film 34 of the auxiliary storage bag, so as to envelop the receiving hole 83 to form the auxiliary storage bag 31. The coupling member 81 is installed to the faceplate and engaged with the coupling member 82 of the storage bag side installed to the storage bag 16, so as to attach and/or detach the storage bag.

The feature of FIG. 26E depicts installing the supporter 46 of the coupling unit by surrounding the circumference of the faceplate opening 3. Since the supporter is the film in the shape of the donut type, the coupling unit 81 is coupled with the edge of the outer circumference. The inner film 32 of the auxiliary storage bag is coupled with the skin contact and the outer film 34 of the auxiliary storage bag is coupled with the supporter 46 of the coupling unit, so that the outer circumferences of both film are coupled to form the auxiliary storage bag. On the other hand, the coupling member 82 of the storage bag side installed to the storage bag 16 is engaged with the coupling member, so as to attach and/or detach the storage bag. Aside from the engagement member, the coupling unit may be: a circular flange having an adhesive layer; or the coupling method through the screw. Any coupling method is acceptable.

As depicted in the features of FIG. 26D and of FIG. 26E of the two-piece ostomy system, the auxiliary storage bag is coupled with at least one of the faceplate, and the member installed to the faceplate so that the auxiliary storage bag is at least formed to envelop the receiving hole. The coupling unit is coupled with at least one of the faceplate, the auxiliary storage bag and the member installed to the faceplate. The coupling member 82 of the storage bag side installed to the storage bag 16 is engaged with the coupling member, so as to attach and/or detach the storage bag.

The method of attaching the ostomy appliance is easy in that releasing the release paper and sealing the faceplate on the ostomy appliance are enough. Even though the entry of the excrement advances to the orientation of the outer circumference, the excrement is stored in the auxiliary storage bag through the receiving hole so that the external spreadout is prevented. The shape of the receiving hole may be a slit that is the gap diameter of 0. Alternatively, the bridging unit 85 may be provided not to deform the shape of the receiving hole. Further, the receiving holes may be provided with a plurality of auxiliary storage bags.

As set forth, when entry of the excrement advances to the orientation of the outer circumference, the excrement is stored in the auxiliary storage bag through the receiving hole in an early stage so that the external spreadout is prevented. Since the pressure due to the excrement entering under the faceplate decreases, the decrease prevents the faceplate from advancement of the entry into the horizontal orientation, so as to prevent the skin disorder from diffusing. The structure is simple, the commercialization is easy and it is possible to cheaply provide the products.

FIGS. 27A-G depict the example of using the positional fixation member 95 intended to enhance the workability and the accuracy when attaching the ostomy appliance. The feature of FIG. 27A depicts the longitudinal cross section view neighbor to the receiving hole 83. Each of the faceplate 12 and the skin contact is provided with the skin protection agent layer 13 and the receiving hole 83 is formed between both. Since the faceplate is completely separated from the skin contact, the positional relationship is displaced during attaching the ostomy appliance on the abdomen. Thus, the proper receiving hole is not formed.

For solution, providing the bridging unit 85 is recommended in the embodiment 12 and using the release paper is recommended in the embodiment 13. Next, this embodiment sets forth using the positional fixation member 95. The positional fixation member 95 is arranged across the receiving hole not to deform the shape of the receiving hole 83. The positional fixation member 95 contacts the excrement entering under the faceplate and the skin, so as to decrease the strength of, melting down or releasing the positional fixation member 95.

The feature of FIG. 27B depicts providing the skin protection agent layer 13 in a sequence across the faceplate and the skin contact so that the positional fixation member 95 is formed with a thin skin protection agent layer in a U-shape at the portion of the receiving hole 83. The skin protection agent layer of the positional fixation member is too mechanically strong to be destroyed by burdens of the typical usage. Depending on the positional fixation member, the faceplate is integrated in the skin contact and thus sealed in the correct positional relationship.

According to the feature of FIG. 27C, the excrement entering under the faceplate reached the receiving hole 83. When the excrement contacts the positional fixation member 95, the skin protection agent swells to decrease its mechanical strength. The feature of FIG. 27D depicts the state of melting down and breaking down of the skin protection agent. The faceplate is wrinkled and the receiving hole opens so that the excrement is pushed out.

According to the feature of FIG. 27E, the skin contact is provided with the adhesive layer 38 and the water-soluble sheet is sealed as the positional fixation member. The water soluble sheet may be oblate film made of drying gelatinized starch and the sheet in the shape of the ring. Since the excrement of entry contacts the water-soluble sheet and melts so that the receiving hole becomes open.

According to the feature of FIG. 27F, the faceplate is provided with the skin protection agent layer and the skin contact is provided with the adhesive layer 38. A portion of the faceplate overlaps the skin contact to form integration. A portion of the skin protection agent layer overlapping the skin contact works as the positional fixation member. According to the feature of FIG. 27G, the entered excrement swells the skin protection agent layer. The adhesive strength of the skin protection agent layer which is a portion of the positional fixation member decreases due to swelling to be released from the skin contact. Since the adhesive strength between the skin contact and the skin is too strong to be released, the excrement is stored in the auxiliary storage bag.

The positional fixation member 95 may be provided across the whole of the circumference of the receiving hole. Alternatively, it may be provided at the main portions of the receiving hole while the receiving hole of the other portions may be open. For example, it is recommended to use the positional fixation member on the bridging unit 85 depicted in the embodiment 12. Further, it is recommended to provide the positional fixation member partially or entirely on the receiving hole 83 provide on the faceplate depicted in the embodiment 16. The positional fixation member may be used for both the one-piece ostomy system and the two-piece ostomy system. As set forth, the receiving hole is precisely formed by the positional fixation member. Thus, the excrement due to the blowout is surely stored in the auxiliary storage bag. Even the aged people can sassily and precisely attach the ostomy appliance.

A leakage alarming device alarms the fact that the excrement is stored in the auxiliary storage bag through driving a conveying unit such as a vibrating motor. A mercury cell is used for the power of the device and it is possible to provide a switch that turns on and/or shut down the power. A sensor having at least a pair of bipolar electrodes is arranged in the auxiliary storage bag. The excrement includes water contents containing impurity and thus the electric resistance is low. By measuring the resistance value of the sensor by an analytic circuit, the inflow of the excrement is easily detected. The analytic circuit outputs the analytic signal to the driving unit, which drives the communication unit.

The communication unit should be compact and electricity-saving, e.g. the vibration generator such as the vibration motor; the light emission element such as light emitting diodes; and an alarming sound generator such as the piezoelectric buzzer, which is driven by the driving unit. The driving may last a constant time, continuous, and/or the combination thereof. The inflow of the excrement is known through the vibration, the light or the sound. The methods of using the vibration motor can give the vibration to the abdomen of the ostomate without being known by others.

Alternatively, the piezoelectric speaker may be driven for a constant time through the sound data stored as the voice-sound, music-box-sound or an alarming sound. Further, it is recommended to control a transmitter by the driving unit to transmit encrypted user description codes and codes expressing statuses through radio wave. In this case, the receiver provided in a hospital room or a bedroom receives the radio wave, allowing people in the nurse room or other rooms to know the status of the auxiliary storage bag. The driving unit drives at least one of the communication units.

Figures 28A, 28B:
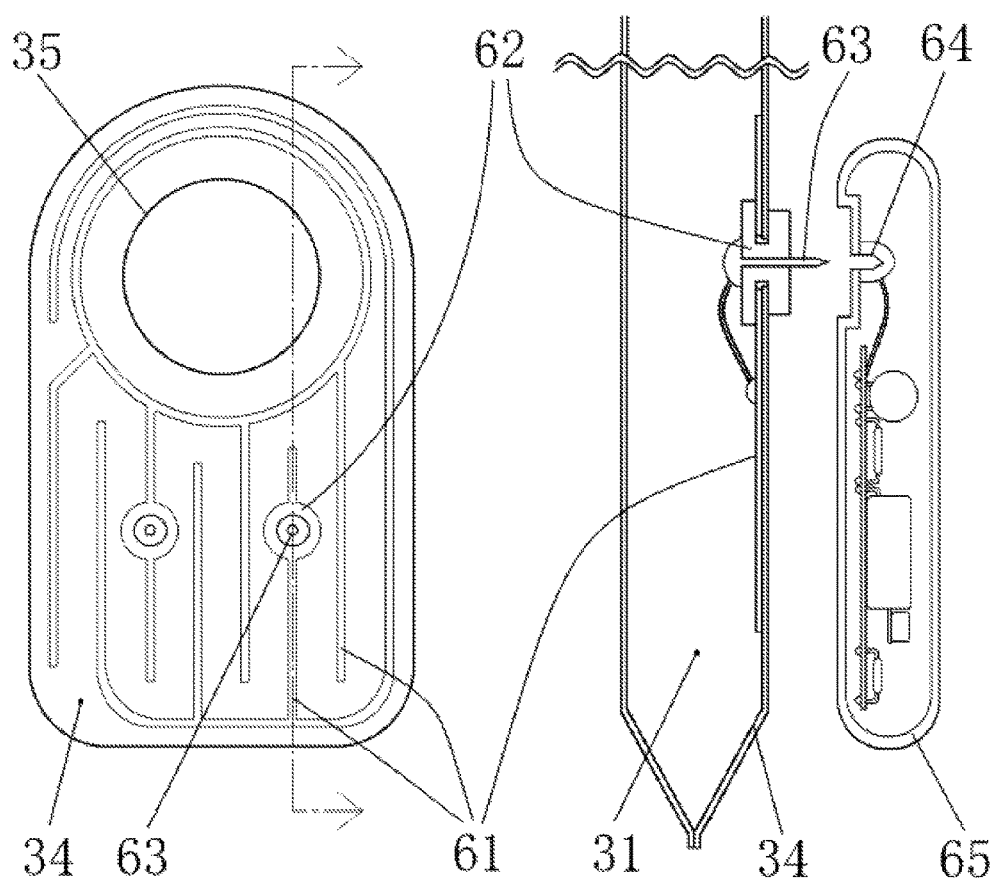
FIG. 28A is a view of an example of a device notifying leakage according to a sixteenth example embodiment.
FIG. 28B is another view of an example of a device notifying leakage according to the sixteenth example embodiment.

Next, FIGS. 28A-B depict the first state of the sensor arranged in the auxiliary storage bag. The representative shape of the outer film 34 of the auxiliary storage bag is depicted in the feature of FIG. 28A. At the center, the second opening 35 is formed. On the middle plane of the auxiliary storage bag, a pair of bipolar electrodes are vapored or the sensor 61 sealed on the metallic thin film is formed. The feature of FIG. 28B depicts the enlarged longitudinal cross section view focusing on the isolated supporter 62 provided on the outer film 34 of the auxiliary storage bag. The sensor is connected through the isolated supporter 62 to the pin 63 protruding to outside.

The package 65 stores the components of the leakage alarming device. The outside of the package 65 is provided with the socket 64. The pin is inserted into the socket to be connected with the analytic circuit and the package is installed on the side surface of the auxiliary storage bag. It should be noted that the socket may be connected to the lead line and the analytic circuit in a distant.

In this embodiment, the sensor is formed on the member configuring the auxiliary storage bag and is connected to the analytic circuit arranged on the outside. In this embodiment, the auxiliary storage bag must be regularly disposed every time while components except the sensor may be repeatedly used.

Figures 29A, 29B:
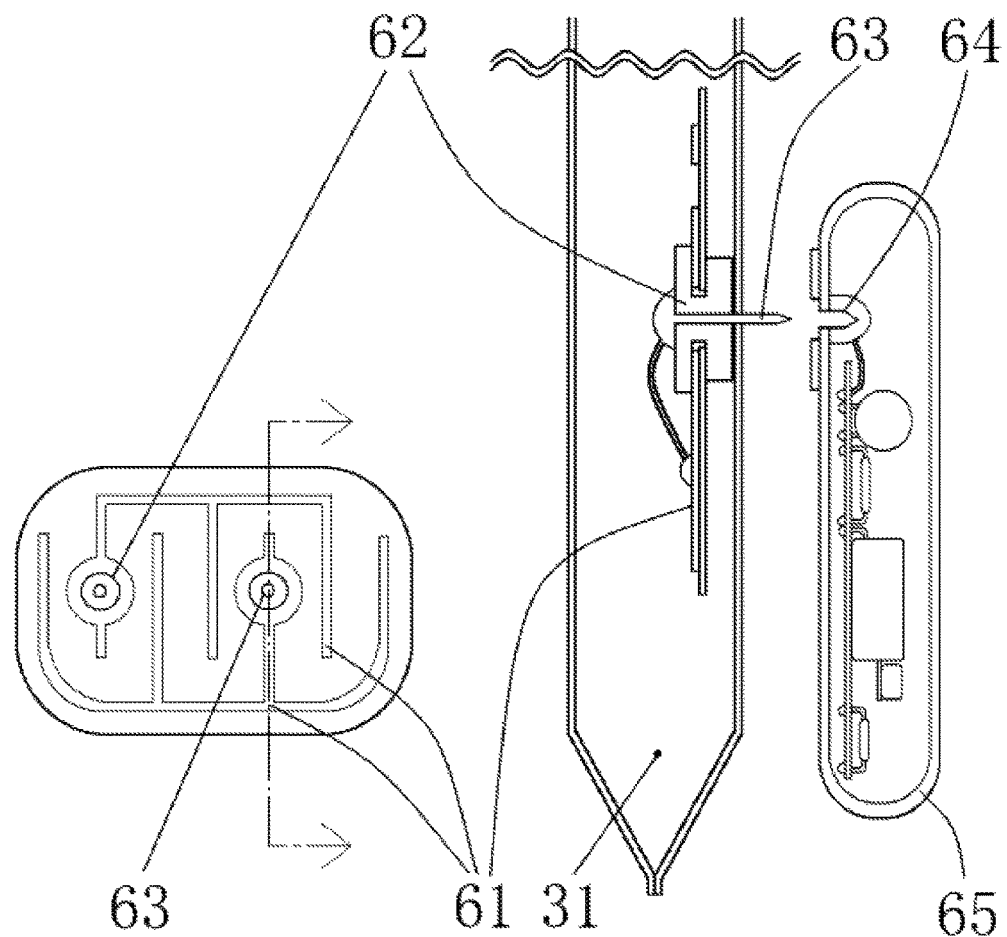
FIG. 29A is a view of a device notifying leakage according to the sixteenth example embodiment.
FIG. 29B is a view of a device notifying leakage according to the sixteenth example embodiment.

Next, FIG. 29A-B depicts the second state of the sensor 61. The sensor 61 as a pair of bipolar electrodes is formed on a surface of a small piece of film and is connected with the pin 63 supported by the isolated supporter 62. This small piece of film is stored in the auxiliary storage bag. As depicted in the feature of FIG. 29B, the pin is inserted from the inside to the outside so that the pin is inserted and engaged in the socket 64. The signal from the pin is connected to the analytic circuit of the electric circuit stored in the package 65. In this embodiment, as long as the sensor does not become dirty, repeated usage together with the components except the sensor is possible.

Figures 30A, 30B:
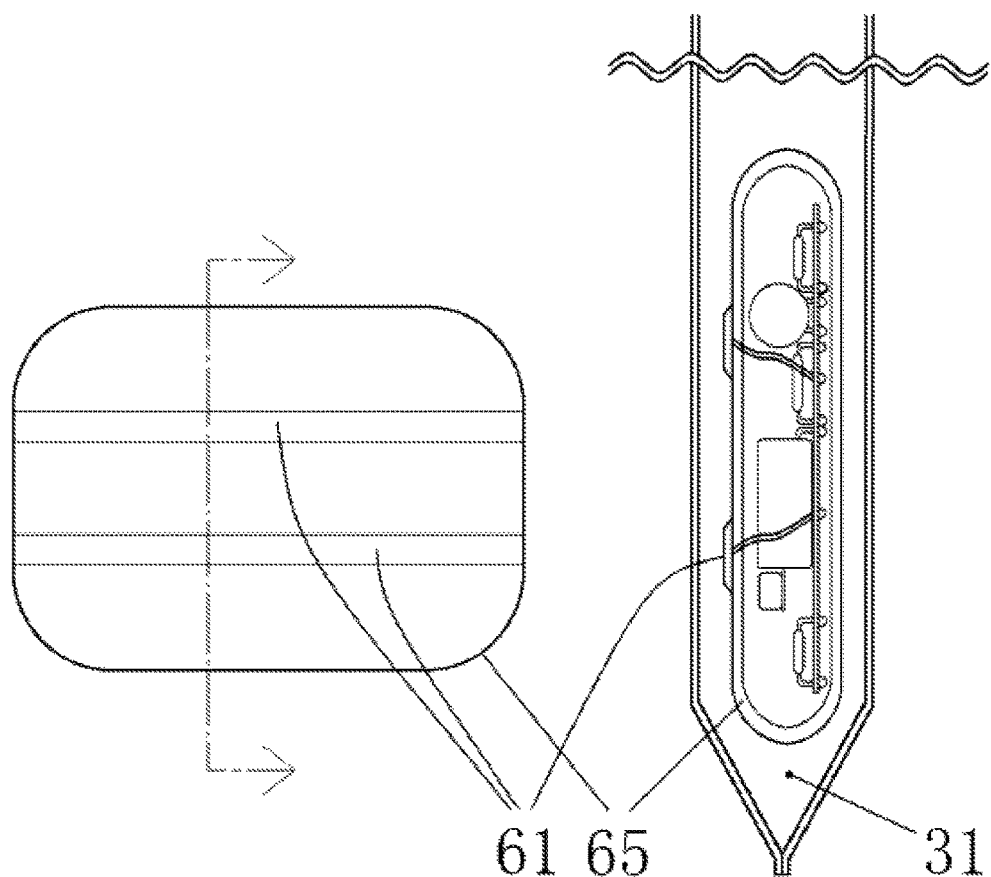
FIG. 30A is a view of a device notifying leakage according to the sixteenth example embodiment.
FIG. 30B is another view of a device notifying leakage according to the sixteenth example embodiment.

Next, FIGS. 30A-B depict the third state. Components configuring the leakage alarming device are accommodated in the package 65 and the sensor is provided in the outside of the package in an exposed state. For usage, this package is entered in the auxiliary storage bag. In this embodiment, the package is disadvantageously polluted by the stored excrement. Thus, it is necessary to be disposed or reused after washed completely. In this embodiment, it is recommended not to install the power switch to avoid the convex and/or concave feature on the surface of the package and the necessity of exchanging the battery cells, i.e. the completely airtight package for factory shipment. Since the standby electricity is little, the lifetime lasts several years and the disposal is recommended after that. As set forth, at least a sensor among components configuring the leakage alarming device must be arranged inside the auxiliary storage bag.

By using the leakage alarming device, when the excrement is stored in the auxiliary storage bag, the communication unit is driven. By exchanging the ostomy appliance in an early stage, the skin disorder is prevented from diffusing. The leakage alarming device may be provided in any one of: the auxiliary storage bag for the ostomy appliance; and the one-piece or two-piece ostomy system having the auxiliary storage bag.

As listed above in this embodiment, the excrement entering under the faceplate that reaches the receiving hole is stored in the auxiliary storage bag through the receiving hole, so as to be prevented from external spreadout. Further, the exchange of the ostomy appliance in an early stage becomes possible, reducing the risk of the skin disorder occurrence. The big and difficult problems from which many ostomates are suffering for a long time is surely solved by this embodiment.

What is claimed is:

1. An ostomy appliance comprising:
   a faceplate having a faceplate opening that captures excrement from a stoma into a storage bag;
   an adhesion unit configured to form a receiving hole around a circumference of the faceplate; and
   an auxiliary storage bag configured to store the excrement leaking between the faceplate and skin of an ostomate, wherein,
   at least an edge of the auxiliary storage bag is coupled to the adhesion unit, and the auxiliary storage bag envelops the caption receiving hole,
   the auxiliary storage bag is provided with a first opening and a second opening,
   the first opening is coupled to the adhesion unit,
   the second opening is coupled to the faceplate, the storage bag and/or a member installed to the faceplate, and
   the auxiliary storage bag envelops the receiving hole.

2. The ostomy appliance according to claim 1, wherein the adhesion unit is arranged on an upper side of the faceplate, and wherein the adhesion unit is not arranged on a lower side of the faceplate.

3. The ostomy appliance according to claim 1, wherein the faceplate is partially coupled with the adhesion unit.

4. The ostomy appliance according to claim 1, wherein, a positional fixation member is installed at least partially across the receiving hole, the positional fixation member being weakened in strength, melt down or released by contacting the excrement leaking between the faceplate and the skin of the ostomate.

5. The ostomy appliance according to claim 1, wherein, the auxiliary storage bag is provided with a first opening and a second opening,
the first opening is coupled to the adhesion unit,
the second opening is coupled to the faceplate and/or a member installed to the faceplate,
the auxiliary storage bag envelops the receiving hole, and
a coupling member configured to detach the storage bag is coupled to the faceplate, the auxiliary storage bag and/or the member installed to the faceplate.

6. The ostomy appliance according to claim 1, wherein, the auxiliary storage bag is provided with a first opening and a second opening,
the first opening is coupled to the adhesion unit,
the second opening is coupled to the faceplate, the storage bag and/or a member installed to the faceplate,
the auxiliary storage bag envelops the receiving hole,
the storage bag is coupled to the faceplate, the auxiliary storage bag and/or the member installed to the faceplate, and
the storage bag envelops the opening of the faceplate.

7. The ostomy appliance according to claim 1, further comprising:
a leakage alarming device including,
a sensor having at least more than two electrodes,
an analysis circuit that analyzes an electric signal from the sensor so as to detect the excrement,
a driver activated by an analysis signal output from the analysis circuit,
a transmission unit activated by the driver, and
a power source that activates the sensor, the analysis circuit, the driver and the transmission unit, wherein the sensor is enclosed in the auxiliary storage bag.

8. An ostomy appliance, comprising:
a faceplate having a faceplate opening that captures excrement from a stoma; and
an auxiliary storage bag that surrounds the faceplate opening and being configured to directly mount to or directly detach from the faceplate, the auxiliary storage bag including,
an adhesion unit configured to form a receiving hole around a circumference of the faceplate, wherein the auxiliary storage bag is configured to store the excrement leaking between the faceplate and skin of an ostomate, wherein at least an edge of the auxiliary storage bag is coupled to the adhesion unit, and wherein the auxiliary storage bag envelops the receiving hole.

9. The auxiliary storage bag for the ostomy appliance according to claim 8, wherein the auxiliary storage bag is provided with a first opening and a second opening, and the first opening is coupled to the adhesion unit and the auxiliary storage bag envelops the ostomy appliance, so that an outlet installed in the storage bag is capable of detachable from the second opening.

10. The auxiliary storage bag for the ostomy appliance according to claim 8, wherein,
the auxiliary storage bag is provided with a first opening and a second opening,
the first opening is coupled to the adhesion unit,
the second opening is sandwiched by the faceplate and the storage bag, and
the auxiliary storage bag is attached to envelop the receiving hole.

11. The auxiliary storage bag for the ostomy appliance according to claim 8, wherein,
the auxiliary storage bag is provided with a first opening and a second opening,
the first opening is coupled to the adhesion unit,
a coupling unit is coupled to the second opening, and mounted to or detached from the faceplate, the storage bag and/or the member installed to the faceplate, and
the auxiliary storage bag is mounted to envelop the receiving hole.

12. The auxiliary storage bag for the ostomy appliance according to claim 8, wherein the adhesion unit is at least arranged on an upper side of the faceplate, and the adhesion unit is not at least arranged on a lower side of the faceplate.

13. The auxiliary storage bag for the ostomy appliance according to claim 8, further comprising:
a leakage alarming device including,
a sensor having at least more than two electrodes,
an analysis circuit that analyzes an electric signal from the sensor so as to detect the excrement,
a driver activated by an analysis signal output from the analysis circuit,
a transmission unit activated by the driver,
a power source that activates the sensor, the analysis circuit, the driver and the transmission unit, wherein the sensor is enclosed in the auxiliary storage bag.

* * * * *